(12) United States Patent
Wijmans et al.

(10) Patent No.: US 6,572,678 B1
(45) Date of Patent: Jun. 3, 2003

(54) NATURAL GAS SEPARATION USING NITROGEN-SELECTIVE MEMBRANES OF MODEST SELECTIVITY

(75) Inventors: Johannes Gerard Wijmans, Menlo Park, CA (US); Richard W. Baker, Palo Alto, CA (US); Zhenjie He, Fremont, CA (US); Ingo Pinnau, Palo Alto, CA (US)

(73) Assignee: Membrane Technology and Research, Inc., Menlo Park, CA (US)

( * ) Notice: Subject to any disclaimer, the term of this patent is extended or adjusted under 35 U.S.C. 154(b) by 0 days.

(21) Appl. No.: 10/033,680

(22) Filed: Dec. 28, 2001

(51) Int. Cl.[7] .............................................. B01D 53/22
(52) U.S. Cl. ........................ 95/47; 95/49; 95/51; 95/52
(58) Field of Search ........................... 95/39, 45, 47–55

(56) References Cited

U.S. PATENT DOCUMENTS

| | | | |
|---|---|---|---|
| 3,534,528 A | * 10/1970 | Porter | 55/16 |
| 3,616,607 A | 11/1971 | Klass et al. | 55/16 |
| 4,119,417 A | 10/1978 | Heki et al. | 55/158 |
| 4,130,403 A | * 12/1978 | Cooley et al. | 55/16 |
| 4,180,388 A | 12/1979 | Graham et al. | 55/16 |
| 4,180,552 A | 12/1979 | Graham et al. | 423/359 |

(List continued on next page.)

FOREIGN PATENT DOCUMENTS

JP 1043329 2/1989

OTHER PUBLICATIONS

D. Gottschlich et al., "Energy Minimization of Separation Processes using Conventional/Membrane Hybrid Systems," Final Report under DOE Contract No. DE91–004710 (1990).

D. Roberts, "The Behavior of a Membrane–Membrane Hybrid," presented at the Sixth Annual Mtg of the North American Membrane Society, Breckenridge, CO, May 1994.

K. Tanaka et al., "Permeability and Permselectivity of Gases in Fluorinated and Non–Fluorinated Polyimides," *Polymer 33*, 585 (1992).

T. Kim et al., "Relationship Between Gas Separation Properties and Chemical Structures in a Series of Aromatic Polyimides," *J. Memb. Sci. 37*, 45 (1988).

S. Stern et al., "Structure Permeability Relationships in Silicone Polymers," *J. Polymer Sci: Polymer Physics Ed. 25*, 1263, (1987).

*Primary Examiner*—Robert H. Spitzer
(74) *Attorney, Agent, or Firm*—J. Farrant

(57) ABSTRACT

A process for treating natural gas or other methane-rich gas to remove excess nitrogen and optionally excess carbon dioxide, water vapor or hydrogen sulfide. The invention relies on gas separation by membranes, using nitrogen/methane selective membranes. The membranes are characterized by having the capability to exhibit a nitrogen/methane selectivity between about 2 and 5 at a temperature higher than about −25° C. The gas may be brought to pipeline specification for nitrogen, and acid gases if present, without requiring the use of amine scrubbing or other acid gas removal technique.

43 Claims, 14 Drawing Sheets

U.S. PATENT DOCUMENTS

| | | | |
|---|---|---|---|
| 4,264,338 A | | 4/1981 | Null .............................. 55/16 |
| 4,386,944 A | * | 6/1983 | Kimura ......................... 55/16 |
| 4,435,191 A | * | 3/1984 | Graham ......................... 55/16 |
| 4,518,399 A | * | 5/1985 | Croskell et al. ............... 55/16 |
| 4,597,777 A | | 7/1986 | Graham ......................... 55/16 |
| 4,639,257 A | * | 1/1987 | Duckett et al. ................ 55/16 |
| 4,701,187 A | | 10/1987 | Choe et al. .................... 55/16 |
| 4,894,068 A | | 1/1990 | Rice .............................. 55/16 |
| 4,931,070 A | | 6/1990 | Prasad ........................... 55/16 |
| 4,963,165 A | | 10/1990 | Blume et al. .................. 55/16 |
| 5,071,451 A | | 12/1991 | Wijmans ....................... 55/16 |
| 5,089,033 A | * | 2/1992 | Wijmans ....................... 55/16 |
| 5,102,432 A | | 4/1992 | Prasad ........................... 55/16 |
| 5,199,962 A | * | 4/1993 | Wijmans ....................... 55/16 |
| 5,282,969 A | | 2/1994 | Xu ............................. 210/640 |
| 5,314,528 A | | 5/1994 | Monereau ...................... 95/55 |
| 5,401,300 A | * | 3/1995 | Lokhandwala et al. ........ 95/49 |
| 5,407,466 A | * | 4/1995 | Lokhandwala et al. ........ 95/49 |
| 5,407,467 A | * | 4/1995 | Lokhandwala et al. ........ 95/49 |
| 5,556,449 A | * | 9/1996 | Baker et al. .................... 95/49 |
| 5,558,698 A | * | 9/1996 | Baker et al. .................... 95/49 |
| 5,647,227 A | | 7/1997 | Lokhandwala ............... 62/624 |
| 5,669,958 A | | 9/1997 | Baker et al. .................... 95/50 |
| 5,762,685 A | * | 6/1998 | Baker et al. .................... 95/39 |
| 6,053,965 A | * | 4/2000 | Lokhandwala ................. 95/49 |
| 6,168,649 B1 | * | 1/2001 | Jensvold et al. ............... 95/47 |
| 6,361,582 B1 | * | 3/2002 | Pinnau et al. .................. 95/45 |
| 6,361,583 B1 | * | 3/2002 | Pinnau et al. .................. 95/45 |
| 6,425,267 B1 | * | 7/2002 | Baker et al. .................. 62/624 |

* cited by examiner

NATURAL GAS SEPARATION USING NITROGEN-SELECTIVE MEMBRANES OF MODEST SELECTIVITY

FIELD OF THE INVENTION

The invention relates to the treatment of natural gas that is out of specification with respect to nitrogen. More particularly, the invention relates to the removal of nitrogen from such natural gas by means of gas-separation membranes.

BACKGROUND OF THE INVENTION

Fourteen percent of known U.S. natural gas reserves contain more than 4% nitrogen. The gas in as many as a third or more of these reserves also contains more than 2% carbon dioxide, making it sub-quality with regard to both gases. Significant amounts of gas are also contaminated by hydrogen sulfide, for which pipeline specification is lower than 4 ppm. Many of these reserves cannot be exploited because no economical technology for removing the nitrogen exists.

Cryogenic distillation is the only process that has been used to date on any scale to remove nitrogen from natural gas. The gas streams that have been treated by cryogenic distillation, for example streams from enhanced oil recovery, have large flow rates and high nitrogen concentration, such as more than 10 vol %. Cryogenic plants can be cost-effective in these applications because all the separated products have value. The propane, butane and heavier hydrocarbons can be recovered as natural gas liquids (NGL), the methane/ethane stream can be delivered to the gas pipeline and the nitrogen can be reinjected into the formation.

Cryogenic plants are not used more widely because they are costly and complicated. A particular complication is the need for significant pretreatment to remove water vapor, carbon dioxide and $C_{3+}$ hydrocarbons and aromatics to avoid freezing of these components in the cryogenic section of the plant, which typically operates at temperatures down to $-150°$ C. The degree of pretreatment is often far more elaborate and the demands placed upon it are far more stringent than would be required to render the gas acceptable in the pipeline absent the excess nitrogen content.

For example, pipeline specification for water vapor is generally below about 120 or 140 ppm; to be fit to enter a cryogenic plant, the gas must contain no more than 1–2 ppm of water vapor at most. Similarly, 2% carbon dioxide content may pass muster in the pipeline, whereas carbon dioxide must be present at levels no higher than about 100 ppm for cryogenic separation. For streams of flow rates less than about 50–100 MMscfd, therefore, cryogenic technology is simply too expensive and impractical for use.

Other processes that have been considered for performing this separation include pressure swing adsorption and lean oil absorption; none is believed to be in regular industrial use.

The potential production of gas containing 10 to 30% nitrogen is about 8,500 MMscfd. At present, approximately 4,500 MMscfd of this gas is treated by cryogenic processes, leaving about 4,000 MMscfd of gas unused because it is unsuitable for cryogenic treatment. Much of this gas is in small fields and is contaminated with carbon dioxide or/and hydrogen sulfide.

Gas separation by means of membranes is known. For example, numerous patents describe membranes and membrane processes for separating oxygen or nitrogen from air, hydrogen from various gas streams and carbon dioxide from natural gas. Such processes are in industrial use, using glassy polymeric membranes. Rubbery polymeric membranes are used to separate organic components from air or other gas mixtures.

A report by SRI to the U.S. Department of Energy ('Energy Minimization of Separation Processes using Conventional Membrane/Hybrid Systems", D. E. Gottschlich et al., final report under contract number DE 91-004710, 1990) suggests that separation of nitrogen from methane might be achieved by a hybrid membrane/pressure swing adsorption system. The report shows and considers several designs, assuming that a hypothetical nitrogen-selective membrane, with a selectivity for nitrogen over methane of between 5 and 15 and a transmembrane pressure-normalized methane flux of $1 \times 10^{31\ 6}$ $cm^3(STP)/cm^2 \cdot s \cdot cmHg$, were to become available, which to date it has not.

In fact, both glassy and rubbery membranes have poor selectivities for nitrogen over methane or methane over nitrogen. Table 1 lists some representative values for glassy materials.

TABLE 1

| Polymer | Permeability (Barrer) | | Selectivity (−) | | Ref. |
| --- | --- | --- | --- | --- | --- |
| | $N_2$ | $CH_4$ | $N_2/CH_4$ | $CH_4/N_2$ | |
| Polyimide (6FDA-mp'ODA) | 0.26 | 0.13 | 2.1 | 0.5 | 1 |
| Polyimide (6FDA-BAHF) | 3.10 | 1.34 | 2.3 | 0.4 | 1 |
| Polyimide (6FDA-IPDA) | 1.34 | 0.70 | 1.9 | 0.5 | 2 |
| Polyimide (6FDA-MDT) | 0.40 | 0.20 | 2.0 | 0.5 | 4 |
| Polyimide (6FDA-CDM) | 0.27 | 0.12 | 2.3 | 0.4 | 4 |
| Polyimide (6FDA-HAB) | 0.17 | 0.056 | 3.0 | 0.3 | 4 |
| Polyimide (6FDA-MDA) | 0.20 | 0.10 | 2.0 | 0.5 | 2 |
| Polyimide (BPDA-MDT) | 0.048 | 0.028 | 1.7 | 0.6 | 4 |
| Polyimide (BPDA-HAB) | 0.001 | 0.0004 | 2.4 | 0.4 | 4 |
| Cellulose acetate | 0.35 | 0.43 | 0.8 | 1.2 | 3 |
| Polycarbonate | 0.37 | 0.45 | 0.8 | 1.2 | 3 |
| Polysulfone | 0.14 | 0.23 | 0.6 | 1.7 | 3 |
| Hyflon ® AD60 | 20 | 8–9 | 2.3 | | 5 |
| Hyflon ® AD80 | 30–40 | 14–19 | 2.1 | | 5 |
| Cytop ® | 5 | 1–2 | 2.7 | | 5 |

1. K. Tanaka et al., "Permeability and Permselectivity of Gases in Fluorinated and Non-Fluorinated Polyimides", Polymer 33, 585 (1992).
2. T. H. Kim et al., "Relationship Between Gas Separation Properties and Chemical Structures in a Series of Aromatic Polyimides", J. Memb. Sci., 37, 45 (1988).
3. J. G. Wijmans, "Membrane Processes and Apparatus for Removing Vapors from Gas Streams", U.S. Pat. No. 5,071,451 (December 1991).
4. S. A. Stern et al., "Structure Permeability Relationships in Silicone Polymers", J. Polymer Sci: Polymer Physics Ed. 25, 1263 (1987).
5. Inventors' estimate.

The problem of separating gas mixtures containing methane and nitrogen into a methane-rich stream and a nitrogen-rich stream is, therefore, a very difficult one, owing to the low selectivity of essentially all membrane materials to these gases. In addition, many materials that are somewhat selective for one gas over the other have very low permeability.

U.S. Pat. No. 3,616,607 to Northern Natural Gas Company, discloses membrane-based separation of nitrogen from methane for natural gas treatment. The patent reports extraordinarily high nitrogen/methane selectivities up to 15 and 16. These numbers are believed to be erroneous and have not been confirmed elsewhere in the literature. Also, the membranes with these alleged selectivities were made from polyacrylonitrile, a material with extremely low gas permeability of the order $10^{-4}$ Barrer (ten thousandths of a Barrer) that would be impossible to use for a real process.

It was discovered a few years ago that operating silicone rubber membranes at low temperatures can increase the methane/nitrogen selectivity to as high as 5 or above. U.S. Pat. Nos. 5,669,958 and 5,647,227 make use of this discovery and disclose low-temperature methane/nitrogen separation processes using silicone rubber or similar membranes to preferentially permeate methane and reject nitrogen. However, such a selectivity is obtained only at very low temperatures, typically −60° C., for example. Temperatures this low generally cannot be reached by relying on the Joule-Thomson effect to cool the membrane permeate and residue streams, but necessitate additional chilling by means of external refrigeration. While such processes may be workable in industrial facilities with ready access to refrigeration plants, they are impractical in many gas fields, where equipment must be simple, robust and able to function for long periods without operator attention.

Another problem of operating membranes at very low temperature operation is that, just as in conventional cryogenic plants, significant pretreatment is required to avoid system blockages and damage caused by methane hydrate formation or freezing of higher boiling point stream components individually.

A significant problem when rubbery, methane-selective membranes are used is co-permeation of carbon dioxide, hydrogen sulfide, and water that may also be present in the gas. These components permeate the first set of membrane modules and are concentrated in the natural gas product that is to be sent to the pipeline. Since more than one third of the unexploited high-nitrogen gas reserves are also out of specification for carbon dioxide or hydrogen sulfide, this is potentially a common problem. Gas treated in this way also needs dehydration and acid gas removal before delivery to the pipeline. The additional cost and complexity of these additional steps can make the process uneconomical.

Further concerns that hamper membrane process design for methane/nitrogen separation are that vacuum pumps generally must not be used anywhere in the system as they may permit air to leak into lines carrying hydrocarbon mixtures, representing an unacceptable safety hazard. Indeed, for safety, reliability and cost-containment, the number of pieces of rotating or moving equipment of any kind should be kept to a minimum.

In view of these multiple difficulties, there remains an unsatisfied need for economical means of exploiting nitrogen-rich natural gas reserves, especially those contained in gas fields with smaller flow rates.

SUMMARY OF THE INVENTION

The invention is a process for treating natural gas or other methane-rich gas to remove excess nitrogen. The gas to be treated usually contains at least about 4% nitrogen and can contain large amounts, such as 20% nitrogen or above.

The invention relies on membrane separation using a two-step membrane system design. The membranes used in both steps are permeable to nitrogen, carbon dioxide, water vapor and hydrogen sulfide, but relatively impermeable to methane.

A particular feature of the invention, unlike prior art membrane processes disclosed in the literature, specifically the SRI report mentioned above and U.S. Pat. Nos. 5,669,958 and 5,647,227, is that a membrane selectivity between methane and nitrogen of at least 5 is not required.

In fact, the process is characterized by the use of membranes that are capable of providing a selectivity in favor of nitrogen over methane of between about 2 and 5 at a temperature above about −25° C. Unexpectedly, and contrary to previous analysis of the problem in the art, we have discovered that operating within this selectivity range and adopting the process schemes based on a two-step membrane configuration taught in detail below results in an economically practical process for gas treatment.

The process often requires operation at sub-ambient temperatures to provide selectivity within the right range. However, as is well known, the permeability of most polymer materials decreases with decreasing temperature. Therefore, the process relies on a balance between a temperature low enough to provide a useful selectivity and not so low that the permeability of the selective layer material, and hence the flux of the membranes during operation, has dropped to an impractical level.

This balance is achieved by feeding the gas to be treated into the membrane units at a temperature above about −25° C., wherever possible. By operating according to these constraints, the transmembrane pressure-normalized nitrogen flux can generally be maintained above about 1 gpu, and frequently higher, such as above 10 or 20 gpu. This means that the process can be carried out using reasonable amounts of membrane area.

If higher selectivity than can be achieved at room temperature is desired, it can be provided in most cases without the need for any external source of refrigeration, simply by taking advantage of the cooling by Joule-Thomson effect of both permeate and residue streams that takes place in membrane separation processes. This effect is discussed at greater length in copending application Ser. No. 10/035,404, entitled "Natural Gas Separation using Nitrogen-Selective Membranes" and in U.S. Pat. No. 5,762,685, both of which are incorporated herein by reference.

In general, the processes of the invention should be operated at temperatures above about −25° C., and can frequently be operated at above about −10° C. or even around 0° C., 10° C. or above. The ability to function at these comparatively high temperatures and without external cooling in many instances is a particular advantage of the present invention, as it greatly simplifies the process compared with prior art technologies.

For example, metal components of the equipment can be made from carbon steel rather than stainless steel, with considerable cost savings.

In a basic aspect, the process of the invention includes the following steps for treating a feed gas stream:

(a) providing a first membrane unit containing a first membrane having a first feed side and a first permeate side, the first membrane being characterized by having the capability to exhibit a first nitrogen/methane selectivity in the range about 2–5 at a first temperature higher than about −25° C.;

(b) providing a second membrane unit containing a second membrane having a second feed side and a second permeate side, the second membrane being characterized by having the capability to exhibit a second nitrogen/methane selectivity in the range about 2–5 at a second temperature higher than about −25° C., the second membrane unit being connected in series with the first membrane unit such that gas leaving the first feed side can enter the second membrane unit on the second feed side;

(c) passing the gas stream at a feed temperature above about −25° C. into the first membrane unit and across the first feed side;

(d) withdrawing from the first feed side a first residue stream enriched in methane compared with the gas stream;

(e) withdrawing from the first permeate side a first permeate stream depleted in methane compared with the gas stream;

(f) passing the first residue stream into the second membrane unit and across the second feed side;

(g) withdrawing from the second feed side as a product stream a second residue stream enriched in methane compared with the first residue stream, and containing no more than about 6% nitrogen;

(h) withdrawing from the second permeate side a second permeate stream depleted in methane compared with the first residue stream.

Defined from the perspective of balancing selectivity and flux, the basic process of the invention includes the following steps:

(a) providing a first membrane unit containing a first membrane having a first feed side and a first permeate side,
   the first membrane being characterized by having the capability to exhibit a first nitrogen/methane selectivity in the range about 2–5 at a first temperature higher than about −25° C.;

(b) providing a second membrane unit containing a second membrane having a second feed side and a second permeate side,
   the second membrane being characterized by having the capability to exhibit a second nitrogen/methane selectivity in the range about 2–5 at a second temperature higher than about −25° C.,
   the second membrane unit being connected in series with the first membrane unit such that gas leaving the first feed side can enter the second membrane unit on the second feed side;

(c) passing the gas stream into the first membrane unit, at a feed temperature sufficient to provide a nitrogen/methane selectivity between about 2 and 5 and a pressure-normalized nitrogen flux of at least about 1 gpu, into the first membrane unit and across the first feed side;

(d) withdrawing from the first feed side a first residue stream enriched in methane compared with the gas stream;

(e) withdrawing from the first permeate side a first permeate stream depleted in methane compared with the gas stream;

(f) passing the first residue stream into the second membrane unit and across the second feed side;

(g) withdrawing from the second feed side as a product stream a second residue stream enriched in methane compared with the first residue stream, and containing no more than about 6% nitrogen;

(h) withdrawing from the second permeate side a second permeate stream depleted in methane compared with the first residue stream.

The first membrane unit produces a permeate gas rich in nitrogen compared with the feed gas, and containing most of the carbon dioxide, hydrogen sulfide and water vapor, if these components are present in the original feed.

The first permeate stream can be flared or used as fuel, for example. As a preferred alternative, it is possible to include a third membrane unit to treat the first permeate stream by fractionating it into a comparatively methane-rich residue stream, which may be recirculated within the process for additional methane recovery, and a comparatively nitrogen-rich third permeate stream, which may be flared, used as fuel, reinjected, or sent to any other destination as desired.

The high-pressure residue gas from the first membrane unit, now reduced in contaminants, is sent to the second membrane unit, which removes the remaining excess nitrogen. The residue gas from the second membrane step typically contains methane and ethane, as well as other light hydrocarbons, if present in the original feed. This gas has been reduced to the chosen target specification for nitrogen, and is substantially free of carbon dioxide, hydrogen sulfide and water vapor. The gas is at high pressure and may be delivered to the pipeline, if appropriate, without further treatment.

The permeate from the second membrane separation step frequently contains too much methane for the stream to be discharged to waste. Preferred embodiments of the invention include recirculating this permeate stream from the second membrane separation step to the front of the process to increase methane recovery.

By adopting one of these preferred embodiments, the fuel to run any compressor needed for the process can usually be generated as a discrete product stream by the process itself. This is very beneficial as gas-fired compressors can operate in remote locations where an electrical power supply is unavailable.

The process of the invention offers a number of additional features and advantages. Importantly, it enables natural gas containing relatively large amounts of nitrogen, such as 10%, 20% or higher, to be brought close to or within pipeline specification of no more than 4% nitrogen. As an added feature, natural gas that is out of specification not just with respect to nitrogen, but also with respect to carbon dioxide, can be brought within specification for both of these components simultaneously by a single treatment.

Likewise gas that contains either excess hydrogen sulfide or water vapor, or both, in addition to being out of specification with respect to nitrogen and carbon dioxide, can be brought within specification for all components simultaneously.

This ability to meet the "total inerts", hydrogen sulfide and water requirements of pipeline gas in one operation avoids a multitude of potential problems and additional processing requirements downstream of the membrane separation operations.

Furthermore, for small gas streams or remote gas fields, these beneficial results can be achieved more simply, reliably and cheaply than could be done with prior art technology.

In comparison, conventional technology to treat such streams would be to use an amine absorption plant to remove the carbon dioxide and hydrogen sulfide, followed by a glycol absorption unit to remove water and a cryogenic plant to remove the nitrogen. The complexity and combined cost of these multiple operations is excessive, and for operators of smaller field and wells, such as those with gas flows lower than about 50 MMscfd or lower than about 100 MMscfd, can be completely prohibitive.

Even if the other benefits of membrane separation were achieved by using methane-selective membranes, as described in U.S. Pat. Nos. 5,669,958 and 5,647,227 or copending application Ser. No. 09/917,478, now U.S. Pat. No. 6,425,267, pretreatment or post-treatment of gas to remove acid gases and water vapor would often be necessary.

Thus the process of the invention provides an opportunity to open up for production a very large amount, in the billions of scfd, of currently shut-in gas.

Another important advantage of the process of the invention, in many embodiments, is that only one compressor is needed to operate the entirety of the process, that is, to produce dry, low-nitrogen, low-carbon dioxide, pipeline-quality gas at high pressure. The membrane separation units themselves are completely passive pieces of equipment, with no moving parts, no consumable supplies, such as sorbents or catalysts, and no operating fluids that require periodic changing or regeneration.

Thus the simplicity and reliability of the process is in sharp contrast to conventional processes that typically require multiple pumps to adjust gas conditions for different unit operations and to move gas from one unit operation to the next, as well as needing skilled operators and regular maintenance.

The most important product of the process is the methane-rich second residue stream. This product gas is provided from the high-pressure side of the membrane separation system. This is a particular advantage when compared with the prior art processes using methane-selective membranes, where the product natural gas is withdrawn at comparatively low pressure, and results in a beneficial savings in recompression costs.

The process in its most basic embodiment as described above results in a methane product stream of good quality, typically able to meet pipeline specification, and two methane-depleted, contaminant-enriched permeate streams. As mentioned above, the permeate from the second membrane separation step can advantageously be recirculated to the front of the process to increase methane recovery. In this case, it is preferred if the operating parameters of the process are adjusted as described in more detail below to achieve a nitrogen content in the second permeate stream that is similar to the nitrogen content in the feed gas stream. This avoids the inefficiencies associated with mixing streams of unlike compositions.

The permeate from the first membrane separation step is the most nitrogen-rich stream produced by the basic process of the invention. If the feed gas has a very high nitrogen content, such as more than 20% nitrogen, this permeate stream may contain as much as about 40% nitrogen or more. In this case, this stream has value as a potential source of nitrogen, such as for reinjection into the formation producing the raw gas.

More usually, the first permeate stream contains about 20% or 30% nitrogen, and still contains about 50% methane or more. Gas of this composition generally has a Btu value of at least about 500 Btu/scf, high enough to be a good source of compressor fuel gas.

As mentioned above, a particularly preferred embodiment of the invention uses a third membrane separation unit as a second membrane separation stage to further treat this permeate stream. As with the two membrane separation steps of the first stage, the second membrane separation stage uses membranes that are capable of providing a selectivity in favor of nitrogen over methane of between about 2 and 5 at a temperature above about −25° C.

In that case, the process of the invention, expressed in terms of a feed temperature limitation, typically includes the following steps:

(a) providing a first membrane unit containing a first membrane having a first feed side and a first permeate side,
   the first membrane being characterized by having the capability to exhibit a first nitrogen/methane selectivity in the range about 2–5 at a first temperature higher than about −25° C.;

(b) providing a second membrane unit containing a second membrane having a second feed side and a second permeate side,
   the second membrane being characterized by having the capability to exhibit a second nitrogen/methane selectivity in the range about 2–5 at a second temperature higher than about −25° C.,
   the second membrane unit being connected in series with the first membrane unit such that gas leaving the first feed side can enter the second membrane unit on the second feed side;

(c) providing a third membrane unit containing a third membrane having a third feed side and a third permeate side,
   the third membrane being characterized by having the capability to exhibit a third nitrogen/methane selectivity in the range about 2–5 at a third temperature higher than about −25 ° C.,
   the third membrane unit being connected in series with the first membrane unit such that gas leaving the first permeate side can enter the third membrane unit on the third feed side;

(d) passing the gas stream at a feed temperature above about −25° C. into the first membrane unit and across the first feed side;

(e) withdrawing from the first feed side a first residue stream enriched in methane compared with the gas stream;

(f) withdrawing from the first permeate side a first permeate stream depleted in methane compared with the gas stream;

(g) passing the first residue stream into the second membrane unit and across the second feed side;

(h) withdrawing from the second feed side as a product stream a second residue stream enriched in methane compared with the first residue stream, and containing no more than about 6% nitrogen;

(i) withdrawing from the second permeate side a second permeate stream depleted in methane compared with the first residue stream;

(j) passing the first permeate stream into the third membrane unit and across the third feed side;

(k) withdrawing from the third feed side a third residue stream enriched in methane compared with the first permeate stream;

(l) withdrawing from the third permeate side a third permeate stream depleted in methane compared with the first permeate stream.

Clearly, as with the basic two-step process, the process that uses a second stage could also be expressed from the perspective of a selectivity/flux limitation, as follows:

(a) providing a first membrane unit containing a first membrane having a first feed side and a first permeate side,
   the first membrane being characterized by having the capability to exhibit a first nitrogen/methane selectivity in the range about 2–5 at a first temperature higher than about −25° C.;

(b) providing a second membrane unit containing a second membrane having a second feed side and a second permeate side,
   the second membrane being characterized by having the capability to exhibit a second nitrogen/methane selectivity in the range about 2–5 at a second temperature higher than about −25° C., the second membrane unit being connected in series with the first membrane unit such that gas leaving the first feed side can enter the second membrane unit on the second feed side;

(c) providing a third membrane unit containing a third membrane having a third feed side and a third permeate side, the third membrane being characterized by having the capability to exhibit a third nitrogen/methane selectivity in the range about 2–5 at a third temperature higher than about −25° C., the third membrane unit being connected in series with the first membrane unit such that gas leaving the first permeate side can enter the third membrane unit on the third feed side;

(d) passing the gas stream, at a feed temperature sufficient to provide a nitrogen/methane selectivity between about 2 and 5 and a pressure-normalized nitrogen flux of at least about 1 gpu, into the first membrane unit and across the first feed side;

(e) withdrawing from the first feed side a first residue stream enriched in methane compared with the gas stream;

(f) withdrawing from the first permeate side a first permeate stream depleted in methane compared with the gas stream;

(g) passing the first residue stream into the second membrane unit and across the second feed side;

(h) withdrawing from the second feed side as a product stream a second residue stream enriched in methane compared with the first residue stream, and containing no more than about 6% nitrogen;

(i) withdrawing from the second permeate side a second permeate stream depleted in methane compared with the first residue stream;

(j) passing the first permeate stream into the third membrane unit and across the third feed side;

(k) withdrawing from the third feed side a third residue stream enriched in methane compared with the first permeate stream;

(l) withdrawing from the third permeate side a third permeate stream depleted in methane compared with the first permeate stream.

The processes of the invention are principally directed to treating various types of natural gas streams, such as those arising from gas wells, oil wells or landfills. However, the processes are applicable, and are expected to be of value, in treating any gas streams that contain a mix of methane and nitrogen with acid gas and/or water vapor. Representative, non-limiting examples of such streams are streams produced during coal gasification, syngas manufacture and related gas-to-liquids technologies.

It is an object of the invention to provide a process for removing excess nitrogen from methane-containing gas mixtures.

It is an object of the invention to provide a practical membrane-based process for removing nitrogen from natural gas that operates at modest nitrogen/methane selectivity.

It is an object of the invention to provide a process for bringing raw natural gas into specification for nitrogen in a simple manner.

It is an object of the invention to provide a simple, reliable and cost-effective method for processing nitrogen-contaminated natural gas from small or remote fields.

It is an object of the invention to provide a membrane-based process for processing nitrogen-contaminated natural gas that also generates combustion fuel to drive the process.

Other objects and advantages will be apparent from the description of the invention to those skilled in the gas separation arts.

DETAILED DESCRIPTION OF THE INVENTION

Figure 1:
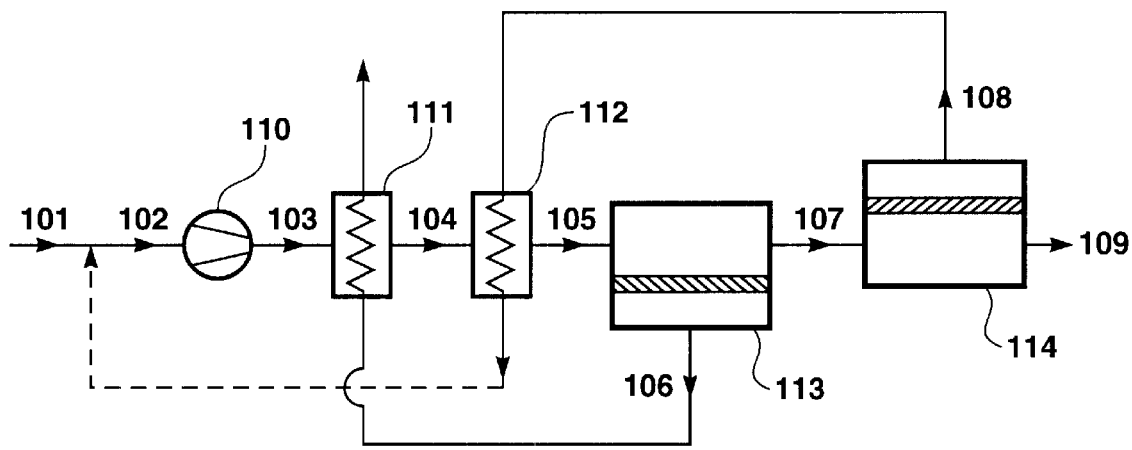
FIG. 1 is a schematic drawing of a basic embodiment of the invention, and including compression and cooling by heat exchange of the feed stream.

The terms gas and vapor are used interchangeably herein.

The term $C_{2+}$ hydrocarbon means a hydrocarbon having at least two carbon atoms; the term $C_{3+}$ hydrocarbon means a hydrocarbon having at least three carbon atoms, and so on.

The term heavier hydrocarbons means $C_{3+}$ hydrocarbons.

The term light hydrocarbons means $C_1$–$C_6$ hydrocarbons.

The terms two-step and multistep as used herein with regard to a membrane separation unit mean an arrangement of membrane modules or banks of membrane modules connected together such that the residue stream from one module or bank of modules becomes the feedstream for the next.

The terms two-stage and multistage as used herein with regard to a membrane separation unit mean an arrangement of membrane modules or banks of membrane modules connected together such that the permeate stream from one module or bank of modules becomes the feedstream for the next.

The term stage-cut means the ratio of permeate flow to feed flow for a membrane unit, in other words the volume fraction of the feed gas that permeates the membrane.

Percentages herein are by volume unless otherwise stated.

The invention is a membrane separation process for treating a gas stream containing methane and nitrogen, so as to bring the gas stream within pipeline specification or other desired specification for nitrogen.

The process may be used for gas streams such as those that arise from gas wells, oil wells, including wells employing nitrogen for enhanced oil recovery, landfills and the like.

In its most basic aspect, the invention involves running a natural gas stream that is out of specification, with respect to at least nitrogen, across at least two membrane separation steps in series. The membrane separation steps are equipped with membranes that are selective in favor of all of nitrogen over methane.

If the raw gas to be treated is not at a pressure high enough to provide adequate transmembrane driving force for an efficient process, it may be compressed before it enters the membrane separation steps.

A product residue stream enriched in methane and depleted in nitrogen is withdrawn, at high pressure, from the feed side of the second membrane separation step. Permeate streams depleted in methane and enriched in nitrogen are withdrawn from the permeate sides of the two membrane separation steps. For a practical and economically attractive process, the compositions of all three of these streams are significant.

On the one hand, the amount of nitrogen that is acceptable in a methane-rich natural gas product stream depends on the destination of the methane. Natural gas pipeline specification is typically no more than 4% total inerts, so, depending on the other constituents of the gas, this means no more than about 4% nitrogen, but perhaps no more than about 2% or 3% nitrogen, for example, if carbon dioxide, helium, argon or other constituents are present. If the gas stream can be diluted with a supply of low-nitrogen content gas, higher nitrogen levels may be acceptable, for example up to about 6% or even 8% or more nitrogen.

If the product residue gas is not destined for a natural gas pipeline, but is being produced for some other purpose, then the acceptable nitrogen content may obviously be different from the above.

On the other hand, loss of methane is an important factor in natural gas processing. Pipeline grade natural gas is typically at least about 85–95% methane, so methane is usually the desired product, and substantial losses of product tend to have an adverse effect on process economics. In addition, substantial quantities of methane in the non-product stream may make disposal or further treatment of this stream difficult. Therefore, methane loss should be kept as low as possible. In the present context, methane loss is defined as (lbmol methane in the feed gas to the process)–(lbmol methane in the product residue stream)/(lbmol methane in the feed gas to the process) expressed as a percentage.

As a general guideline, a loss of greater than about 40% of the methane content of the raw gas is undesirable, and much lower losses, such as no more than about 30%, 20%, 10% or 5%, depending on circumstances, are desirable and preferred.

As mentioned in the Summary section above, one of the attractive features of the process is that it can produce multiple streams of value. If the first permeate stream is used as an injectant gas for oil or gas recovery, a greater methane loss into this stream can be tolerated, because of the overall cost savings brought about by reusing the nitrogen rather than relying entirely on fresh injectant gas. In this case methane losses of more than 40% may be acceptable.

A basic representative process of the invention in the configuration is shown in schematic form in FIG. 1. The flow scheme is an example of the case in which the raw gas to be treated is at comparatively low pressure, so the design includes a raw gas compression step.

The process as shown may be carried out at individual wellheads or on pooled gas at intermediate stations or central gas-processing facilities. It will be appreciated by those of skill in the art that this and the other figures are very simple schematic diagrams, intended to make clear the key aspects of the invention, and that an actual process train will usually include many additional components of a standard type, such as heaters, chillers, condensers, pumps, blowers, other types of separation and/or fractionation equipment, valves, switches, controllers, pressure-, temperature-level- and flow-measuring devices and the like.

Turning specifically to FIG. 1, raw natural gas stream, 101, is optionally mixed with stream 108, described below, to form stream 102, and passes into compression step, 110, emerging as compressed stream, 103. Stream 101 may be any natural gas, or indeed any methane-containing gas, from which it is desired to remove nitrogen, and optionally to remove carbon dioxide, hydrogen sulfide or water vapor, if present. The gas may be from a natural gas well, may be associated gas produced in conjunction with oil, either spontaneously or as a result of nitrogen injection for enhanced oil recovery, may be gas gathered from a landfill, or may arise from any other source.

Stream 101 may be as-extracted from the ground or may have been subjected to pretreatment of any kind, including, but not limited to, filtration to remove particulates, entrained water or hydrocarbon liquids, separation by any means, including, but not limited to absorption, adsorption, condensation and membrane separation, of gaseous contaminants, such as acid gases, $C_{3+}$ hydrocarbon vapors or water vapor, and other membrane or non-membrane separation of methane and nitrogen. Stream 101 is typically at above atmospheric pressure, such as at a few hundred psia, but is not typically at sufficiently high pressure for the desired process performance.

The standard natural gas pipeline specification for inert gas content is less than 4%, so stream 101 will usually contain at least about 4% nitrogen, and frequently will contain considerably more nitrogen, such as at least about 10% or more. The process of the invention can be applied to streams of any nitrogen concentration in principle, but becomes increasingly expensive and requires additional treatment steps as the nitrogen concentration rises above about 25% or 30% nitrogen. Thus, it is most preferred that the nitrogen content of stream 101 be no more than about 30%.

Frequently, stream 101 may also be out of specification with respect to carbon dioxide. Pipeline specification for carbon dioxide is usually no more than 2%. Thus, stream 101 may contain at least 2% carbon dioxide, and frequently contains considerably more, such as at least 5%, 10% or more.

Raw natural gas always contains at least a little water vapor. The typical water content is up to about 1,200 ppm (0.12%); pipeline specification is generally below about 140 ppm or 120 ppm. Therefore, essentially all raw natural gas requires treatment to lower the water dewpoint, and stream 101 is likely in most cases to be out of specification with respect to water vapor also. The process of the invention is usable to treat a stream containing any amount of water vapor, up to saturation.

Since contamination with hydrogen sulfide is common, stream 101 may further contain hydrogen sulfide as a component to be removed. Pipeline specification for hydrogen sulfide is generally no higher than about 4 ppm.

The other most significant component of the stream is methane, usually the major component, and the stream may typically contain a number of other components in minor or trace amounts, most commonly ethane, $C_{3+}$ hydrocarbons and other inert gases such as helium and argon.

The compressor used in compression step 110 may be of any convenient type, such as centrifugal, screw or reciprocating, based on considerations of outlet pressure needed, gas flow rate and composition, and like issues familiar to those of skill in the art. Screw compressors are relatively inexpensive and are widely used to reach pressures up to about 300 or 400 psia; for higher pressures, piston compressors are more commonly used. Typically, but not necessarily, the compression step raises the pressure of the gas stream between about 3-fold and 10-fold. This may be done in a single-stage or multiple-stage compressor, as is well known in the art.

For most applications of the process, it is neither necessary nor desirable to compress the feed gas to very high pressures. Preferred pressures are in the range about 200 psia to 2000 psia, and pressures between about 800 psia and 1,500 psia are most preferred.

It is convenient, desirable, and generally possible to use one or other of the nitrogen-rich permeate streams, or part thereof, to power a gas engine to drive the compressor. This provides a cost advantage that is one of the attractive features of the process.

After compression, stream 103 is introduced into the feed side of first membrane separation step 113. This may be done directly, or as shown in FIG. 1, after the stream has been cooled by heat exchange. In this case, stream 103 passes through first heat exchange step 111, where it is cooled by running in heat exchanging relationship against stream 106, forming partially cooled stream 104. Since $C_{3+}$ hydrocarbons are always likely to be present in stream 103 to some extent, cooling will frequently result in the condensation of a portion of these hydrocarbons, which may be removed in a knock-out pot, not shown, as is well known in the industry. Stream 104 passes through second heat exchange step 112, where it is cooled by running in heat exchanging relationship against second permeate stream 108, to form cooled stream 105. Again, any condensed material may be removed by running through a knock-out pot.

Stream 105 is passed on the feed side into membrane separation step 113. The goal of this step is to reduce the level of nitrogen and, if present, carbon dioxide, water vapor and hydrogen sulfide, in the stream. To meet this goal, the first membrane separation step relies on a membrane that is selective in favor of nitrogen over methane, carbon dioxide over methane, hydrogen sulfide over methane, and water vapor over methane.

A synthetic polymer membrane separates the components of a gas or vapor mixture because the components permeate the membrane at different rates. The permeability, P [$cm^3$ (STP)·cm/$cm^2$·s·cmHg], of a polymer membrane material for a gas is defined as the rate at which that gas moves through a standard thickness [1 cm] of the material under a standard driving force [a pressure difference of 1 cmhg].

A measure of the ability of a membrane to separate two gases is the selectivity, $\alpha$, defined as the ratio of the gas permeabilities, $P_1/P_2$. Selectivity can also be expressed as:

$$\alpha = D_1/D_2 \cdot k_1/k_2$$

where D is the diffusion coefficient of the gas in the membrane [$cm^2$/s], which is a measure of the gas mobility, and k is the Henry's law sorption coefficient, which links the concentration of the gas in the membrane material to the pressure in the adjacent gas [$cm^3$(STP)/$cm^3$·cmHg].

The intrinsic selectivity of a polymer material is established by measuring the permeabilities with pure gas or vapor samples, then calculating the ratio. The actual selectivity obtained in a real separation process is established by making permeation measurements with gas mixtures.

The ratio $D_1/D_2$ is the ratio of the diffusion coefficients of the two gases and can be viewed as the mobility selectivity, reflecting the different sizes of the two molecules. The ratio $k_1/k_2$ is the ratio of the Henry's law solubility coefficients of the two gases and can be viewed as the solubility selectivity, reflecting the relative condensabilities of the two gases.

In all polymer materials, the diffusion coefficient decreases with increasing molecular size. Hence, the mobility component of the selectivity always favors the passage of small molecules over large ones. The solubility component of the selectivity, on the other hand, is a measure of the energy required for sorption and normally increases with molecular diameter, because larger molecules are normally more condensable than smaller ones. The combined effect of these two factors determines the selectivity of the membrane.

Depending on the nature of the polymer, either the diffusion or the sorption component of the permeability may dominate. In rigid, glassy polymer materials, the diffusion coefficient tends to be the controlling factor and the ability of molecules to permeate is very size dependent. As a result, glassy membranes tend to permeate small, low-boiling molecules, such as hydrogen and methane, faster than larger, more condensable molecules, such as $C_{2+}$ organic molecules. For rubbery or elastomeric polymers, the difference in size is much less critical, because the polymer chains can be flexed, and sorption effects generally dominate the permeability. Elastomeric materials, therefore, tend to permeate large, condensable hydrocarbon molecules faster than small, low-boiling molecules. Thus, most rubbery materials are selective in favor of all $C_{3+}$ hydrocarbons over methane.

The molecular kinetic diameters of nitrogen (3.64 Å) and methane (3.8 Å) are similar, and methane has a critical temperature of −82.6° C., so is only moderately more soluble than nitrogen in most polymer materials. The slightly smaller molecular size of nitrogen means that glassy materials slightly favor the passage of nitrogen over methane. The relative condensability of methane means that rubbery materials slightly favor the passage of methane over nitrogen. As a result of the similar molecular sizes and the poor condensability of both components, however, both glassy and rubbery membrane materials have poor selectivity for this gas pair.

However, by using the processes of the invention, these apparently poor materials can be used to remove nitrogen from natural gas well enough to meet pipeline specification, and to do this in an economically practical manner. To achieve this goal, the membrane layer responsible for the separation properties should be capable of exhibiting a nitrogen/methane selectivity, as measured with a gas mixture containing at least nitrogen and methane, of at least about 2, and preferably in the range about 2–5, at a temperature higher than about −25° C.

Examples of polymers that can be used to make such membranes are the most nitrogen-selective materials listed in Table 1, particularly 6FDA-based polyimides, where 6FDA is the structure:

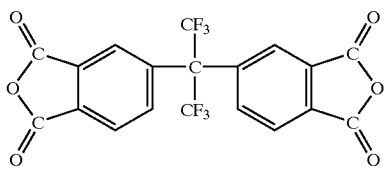

Representative 6FDA polyimides that may be considered for use in the invention include 6FDA-IPDA and 6FDA-BAHF, for example.

Another polyimide class that is believed to contain useful selective layer materials is the perfluorinated polyimides. Such materials have been investigated for use as optical waveguides, and their preparation is described, for example, in S. Ando et al.,*"Perfluorinated polymers for optical waveguides"*, CHEMTECH, December, 1994. To be usable as membrane materials, the polyimides have to be capable of being formed into continuous films. Thus, polyimides that incorporate ether or other linkages that give some flexibility to the molecular structure are preferred. Particular examples are polymers comprising repeat units prepared from the perfluorinated dianhydride 1,4-bis(3,4-dicarboxytrifluorophenoxy) tetrafluorobenzene (10FEDA), which has the structure:

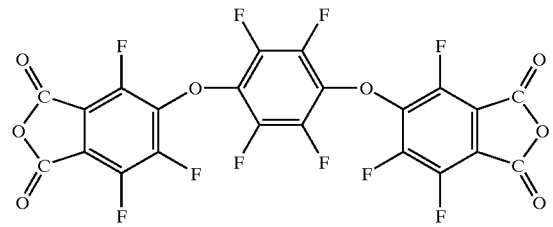

Diamines with which 10FEDA can be reacted to form polyamic acids and hence polyimides include 4FMPD, which has the structure:

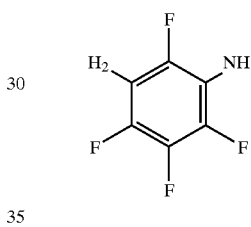

The resulting 10FEDA/4FMPD polyimide has the repeat unit structure:

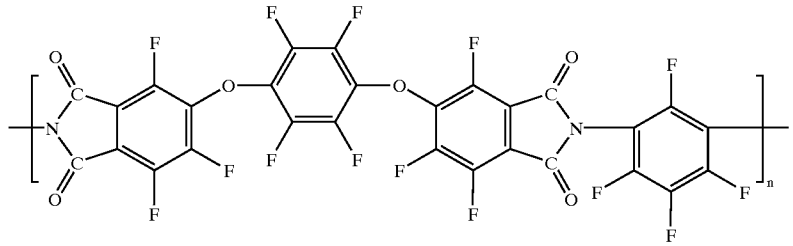

where n is a positive integer.

Yet another group of polymers that includes materials suitable for use in the invention is glassy polymers characterized by having repeating units of a fluorinated, non-aromatic cyclic structure, the ring having at least five members, and further characterized by a fractional free volume no greater than about 0.3. Preferred polymers in this group are formed from fluorinated monomers of (i) dioxoles, which are five-member rings of the form

that polymerize by opening of the double bond, or (ii) dioxolanes, similar five-member rings but without the double bond in the main ring, or (iii) aliphatic structures having an alkyl ether group, polymerizable into cyclic ether repeat units with five or six members in the ring. The polymers may take the form of homopolymers or copolymers. Such materials are discussed at length in copending patent application Ser. No. 09/574,420, now U.S. Pat. 6,361,583, entitled "Gas Separation Using Organic-Vapor-Resistant Membranes", which is incorporated herein by reference as it relates to nitrogen/hydrocarbon separations.

Specific preferred materials in this group are copolymers of tetrafluoroethylene with 2,2,4-trifluoro-5-trifluoromethoxy-1,3-dioxole having the structure:

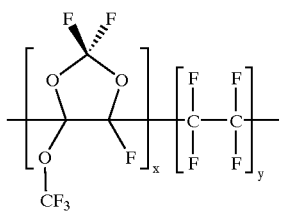

here x and y represent the relative proportions of the dioxole and the tetrafluoroethylene blocks, such that x+y=1.

Such materials are available commercially from Ausimont S.p.A., of Milan, Italy under the trade name Hyflon® AD. Different grades are available varying in proportions of the dioxole and tetrafluoroethylene units.

A second preferred material of this type has the structure:

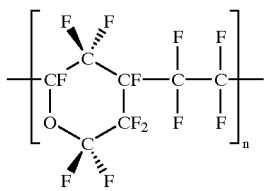

where n is a positive integer.

This material is available commercially from Asahi Glass Company, of Tokyo, Japan under the trade name Cytop®.

As yet another alternative, membranes suitable for use in the invention are characterized in terms of their selectivity before and after exposure to liquid hydrocarbons. In this case, the polymer need not incorporate a cyclic structure. The selective layer is again made from an amorphous glassy polymer or copolymer with a fractional free volume no greater than about 0.3, and has a glass transition temperature, Tg, of at least about 100° C. The polymer is fluorinated, generally heavily fluorinated, by which we mean having a fluorine:carbon ratio of atoms in the polymer of at least about 1:1. Such materials are discussed at length in copending patent application Ser. No. 09/574,303, now U.S. Pat. No. 6,361,582, entitled "Gas Separation Using $C_{3+}$ Hydrocarbon-Resistant Membranes", which is incorporated herein by reference in its entirety.

Typically, the selectivity of polymeric materials increases as the temperature declines, but the lower temperature also results in lower permeability. Therefore, since the glassy materials that are used to make membranes for the present process are neither very selective nor (when compared to the rubbery materials taught in U.S. Pat. Nos. 5,669,958 and 5,647,227) very permeable, a careful balance between selectivity and permeability is required for a cost-effective process.

Depending on the specific polymer material used, it is possible that nitrogen/methane selectivity could be pushed to above 5, by operating at a temperature well below −60° C., for example. Beside the many practical disadvantages of operating at such a low temperature (freezing or condensation of high-boiling gas components, hydrate formation, hydrocarbon condensation within the membrane modules, need for stainless steel rather than carbon steel, provision of external refrigerants, need for insulation, and so on), the permeability under such conditions may drop to such a degree that adequate transmembrane flux cannot be obtained. Most of the gas streams to be treated by the process of the invention are large, in excess of 1 MMscfd, so a reasonably high flux is required lest the amount of membrane area needed to perform the separation become impossibly large.

For any component gas, the flux of that gas through the membrane J (in $cm^3(STP)/cm^2 \cdot s$) is given by:

$$J = \frac{P\Delta p}{l}$$

where P (in $cm^3(STP) \cdot cm/cm^2 \cdot s \cdot cmHg$) is the permeability of the selective layer to that component, Δp is the partial pressure difference (in cmHg) across the membrane for that component, and l (in cm) is the thickness of the selective layer. Thus, the flux across the membrane can be increased by using a thinner selective layer and/or a higher transmembrane driving force. However, a number of factors limit how thin the selective layer can be in practice, and cost limits how high a pressure difference may be provided.

Thus, we believe that, as a general guideline, feed gas stream 105 should preferably be provided to the beginning of the membrane separation train at a temperature that can provide a permeability of the selective layer material for nitrogen of at least about 1 Barrer. If very thin membranes are available and suitable, and/or the feed gas can be provided at very high pressures, such as above about 1,000 psia, then a lower permeability may be acceptable.

Expressed from the point of view of pressure-normalized flux, which is easier to measure in a real process, we prefer that stream 105 be provided at a temperature that can provide a transmembrane nitrogen flux of at least about 1 gpu (1 gpu=1×10$^{-6}$ $cm^3(STP)/cm^2 \cdot s \cdot cmHg$), more preferably at least about 10 gpu, yet more preferably at least about 20 gpu, and most preferably at least about 50 gpu.

Weighing the factors above, in conjunction with process modeling calculations of the type represented in the Examples section below, has led us to the conclusion that the preferred operating temperature for step 113 should be much higher than has previously been supposed. Specifically, we believe that stream 105 should preferably be provided to step 113 at above about −25° C., and more preferably above about −10° C. or even above 0° C. or 10° C. or higher.

In terms of ranges, the preferred feed temperature of stream 105 is between about 25° C. and −25° C., and most preferably between about 10° C. and −10° C.

With these considerations in mind, the perfluorinated, cyclic polymers typified by the Hyflon® and Cytop® product ranges are most preferred as membrane materials. These materials offer nitrogen/methane selectivity above 2 in many cases, in conjunction with nitrogen permeabilities (such as 5 Barrer, 10 Barrer or above) that are typically much higher than those obtainable from typical polyimides.

Since the Joule-Thomson effect promotes cooling of both the permeate and residue streams as gas travels through the membrane modules, the average temperature within a membrane module in the present separations is typically a few degrees or more lower than the temperature at the inlet of the feed. Feed stream 103 can frequently be brought to an appropriate temperature for introducing into the feed side inlet that is within or a little above the above-specified preferred temperature ranges by heat exchange against one or both membrane permeate streams 106 and 108, as shown. Additional cooling of stream 103 may be provided by heat exchange against stream 109 if desired.

Because all of the preferred polymers are glassy and rigid, an unsupported film of the polymer is usable in principle as a single-layer gas separation membrane. However, such layers are normally far too thick to yield acceptable transmembrane flux, and preferably, the separation membrane comprises a very thin selective layer that forms part of a thicker structure, such as an asymmetric membrane or a composite membrane. The thin skin or coating layer is responsible for the separation properties and the underlying integral or discrete microporous support layer is responsible for mechanical strength. Additional layers can be added if desired, such as to seal the support layer before the selective layer is applied, to protect the surface from abrasion, and so on.

A driving force for transmembrane permeation is provided by a pressure difference between the feed and permeate sides of the membrane. This driving force is provided by compression step 110, from which membrane feed stream 103 emerges at an elevated pressure, typically of about 1,000 psia. The pressure on the permeate side may be set to any desired value to give sufficient pressure difference for adequate flux, and subject to the following considerations of pressure ratio.

The ratio feed pressure/permeate pressure is known as the pressure ratio. The mathematical relationship between pressure ratio and selectivity is a complicated expression. (This expression is derived, for example, in Chapter 8 of *Membrane Technology and Applications*, R. W. Baker, McGraw Hill, 2000) This expression predicts three regions of performance, expressed as the permeate concentration of a permeating component, for a membrane separation process.

If the numerical value of the pressure ratio, $\Phi$, is much larger than the numerical value of the selectivity, $\alpha$, then the process operates in the selectivity-limited region, and the permeate concentration is essentially independent of the pressure ratio and is determined by the selectivity. In this region, a membrane separation process can take advantage of the fill intrinsic separating power of the membrane, and, assuming a given feed composition, the higher the selectivity, the better the separation performance will be.

At the other extreme, if the numerical value of the pressure ratio is much smaller than the selectivity, then the process operates in the pressure-ratio-limited region, and the permeate concentration is essentially independent of the membrane selectivity and is determined by the pressure ratio. In the third region, where the pressure ratio and the selectivity are of about the same order of magnitude, the separation performance is affected by both the pressure ratio and the selectivity. In other words, although the pressure ratio influences performance to some extent, the process is still able to benefit from the selectivity of the membrane.

In the present case, we have devised a process that works adequately when the selectivity of the membrane is numerically low, such as 2 or 3. Therefore, the process inclines toward the selectivity-limited region so long as the pressure ratio is at least about 3, and is essentially in the selectivity-limited zone so long as the pressure ratio is at least about 8 or 10. Thus, we have recognized that there is no benefit to the separation performance by operating at substantially higher pressure ratios than about 10 or 15, by providing very high pressures on the feed side, or low pressures on the permeate side. Thus the preferred feed and permeate pressure combinations are such as to give a pressure ratio generally in the range between about 3 and 10.

With further respect to the pressure on the permeate side, the preferred value depends to some extent on the destination of the permeate stream 106, discussed in more detail below. As general guideline, however, maintaining this stream at above-atmospheric pressure, by way of representative value such as 25 psia, 50 psia or 200 psia, facilitates further processing or use. Thus, the preferred permeate-side pressure is typically between about 15 psia and 250 psia.

Before leaving the discussion of membrane properties and operating parameters, mention should also be made of the selectivity of the membranes for carbon dioxide over methane, hydrogen sulfide over methane and water vapor over methane. In general, as shown in the Examples section below, the glassy membrane materials used for the selective layer of the membrane are much more permeable to these components than to nitrogen or methane. Thus, a material that offers a selectivity for nitrogen/methane of 2 will frequently offer a carbon dioxide/methane selectivity at least about 5 times higher, and perhaps at least about 10 times higher, even as measured with gas mixtures containing significant amounts of carbon dioxide at high pressure. Selectivity for hydrogen sulfide over methane is usually slightly lower than for carbon dioxide over methane, and for water vapor over methane is usually higher than for carbon dioxide over methane. The membranes will, therefore, remove all of these gases more selectively than they remove nitrogen.

For use in the process, the membranes may be manufactured as flat sheets or as fibers and housed in any convenient module form, including spiral-wound modules, plate-and-frame modules and potted hollow-fiber modules. The making of all these types of membranes and modules is well known in the art. Flat-sheet membranes in spiral-wound modules are our most preferred choice.

Membrane separation step 113 results in a first permeate stream,106, that is enriched in nitrogen and depleted in methane compared with the membrane feed stream, 105. If carbon dioxide, water vapor or hydrogen sulfide is present in stream 105, this component will also be enriched in stream 106.

This permeate stream 106 is typically at least about 5° C. or 10° C. colder than the feed stream, 105. If desired, therefore, it is optionally possible to use this stream to cool the incoming membrane feed stream, by passing stream 106 in heat-exchanging relationship against stream 103, as indicated by heat exchange step 111 in FIG. 1. Stream 106 is then withdrawn from the process.

Permeate stream 106 maybe sent to any appropriate destination. In the embodiment of FIG. 1, permeate stream 106 is simply indicated as leaving the process. Such an embodiment is generally most suitable when the raw gas to be treated is only slightly out of specification for nitrogen, for example, contains no more than about 6–10% nitrogen. In this case, stream 106 typically represents significantly less than 50% by volume of the raw gas, and discharge of this stream does not equate to a substantial loss of methane product. This stream may then simply be flared, used as fuel, or otherwise disposed of as desired.

However, in many typical cases, where the raw gas contains more than 10% nitrogen and perhaps also excess carbon dioxide, stream 106 is a relatively large stream compared with stream 101, such as more than 50% by volume of stream 101, and simply discharging it from the process will result in an unacceptably high methane loss. Thus it is generally preferred to subject stream 106 to further treatment to reduce methane loss, as discussed in more detail below.

Also, a significant amount of gas is required as engine fuel to drive the compressor of compression step 110 and other compressors and equipment used during gas gathering and processing operations in the field. In fields where turbines are operated, such as for electric power generation, turbine fuel is also needed. Such fuel streams could be provided by diverting a portion of the raw feed gas stream 101 or the high-quality product stream 109. If, instead, gas is taken from stream 106 to power field equipment, particularly the process compressor for step 110, fuel is obtained without having to divert any of either the feed gas 101 or the product gas 109 for this purpose.

Natural gas compressors are usually powered by piston engines, which can typically operate with as little as 50% methane or even slightly less in the fuel. Therefore, stream 106, or a portion thereof, can generally be used as compressor engine fuel, so long as the process can be configured such that this stream has a methane content of at least about 45% or 50%. This will tend to be the case unless the raw gas is very heavily contaminated, such as containing more than about 30% or 35% combined carbon dioxide and nitrogen, for example.

In most cases, therefore, stream 106 is a stream of value, and preferably as much fuel gas as required is obtained as a product stream by diverting a portion of stream 106 for this purpose. This may be done simply by withdrawing a portion of stream 106 without further treatment, or by treating all or part of stream 106, for example by one of the processing schemes discussed below.

First membrane separation step 113 also results in a first residue stream, 107, that is enriched in methane and depleted in nitrogen, as well as carbon dioxide, hydrogen sulfide and water vapor, if present, compared with the membrane feed stream 105. Since the membranes of step 113 are typically much more selective for carbon dioxide, hydrogen sulfide and water vapor over methane than for nitrogen over methane, most of the carbon dioxide, hydrogen sulfide and water vapor in the feed will usually be removed in this step. Stream 107 is withdrawn from the outlet of the first membrane separation step feed side and passed as feed to the feed side inlet of the second membrane separation step 114. Stream 107 will normally be at essentially the same pressure as stream 105, subject only to any small pressure drop that occurs along the length of the membrane modules in step 113. In a properly designed gas separation system, this drop should be no more than a few psi. Thus, recompression, though not explicitly excluded from the process, is not generally required before stream 107 enters step 114. The membranes used in this step are also selective for nitrogen over methane, and are typically, although not necessarily, made from the same membrane materials as the membranes of step 113.

Owing to Joule-Thomson cooling effects instep 113, the feed gas cools as it passes down the module and first residue stream 107 is usually slightly cooler than feed stream 105, and can, therefore, normally pass as feed into step 114 without any additional cooling by heat exchange or external cooling. In some cases, it may be desirable to allow stream 107 to warm after leaving the first membrane step and before entering the second membrane step, to keep the operating temperature of step 114 within the preferred range.

The considerations and preferences concerning membrane type, selectivity, pressure ratio, pressure difference, and so on, in step 114 are similar to those for step 113. Thus, the step: (i) requires membranes with a selective layer that can provide a nitrogen/methane selectivity between about 2 and 5 at a temperature above −25° C.; (ii) should preferably operate at a feed temperature for stream 107 to provide a nitrogen permeability of at least 1 Barrer, or a nitrogen pressure-normalized flux of at least 1 gpu; (iii) should preferably operate at a feed temperature for stream 107 of above about −25° C., and more preferably above about −10° C. or even above 0° C.; (iv) should preferably operate at a feed pressure between about 200 psia to 2,000 psia, more preferably about 800 psia to 1,500 psia; (v) should operate at a permeate pressure typically between about 15 psia and 250 psia.; and (vi) preferably should provide a pressure ratio no higher than about 15, and most preferably in the range about 3–10.

By selectively removing nitrogen, and most of the residual carbon dioxide, hydrogen sulfide and water vapor, if any, into second permeate stream, 108, membrane separation step 114 results in a second residue stream,109, that is further enriched in methane. This stream is the primary product stream of the process, and meets the pipeline or other desired specifications for nitrogen, carbon dioxide, hydrogen sulfide and water vapor. Although pipeline specification is 4% total inerts, it may not always be necessary to reduce the nitrogen content of stream 109 to 4% or below. This is because it may be possible to pool stream 109 with other gas that has a low inerts content before the stream is passed to the pipeline. Thus, in some cases, a nitrogen concentration of, for example, 6%, or even 8% or more, may be acceptable, even if the gas is ultimately destined for a gas pipeline.

The invention is addressed specifically to gas streams that contain excess amounts of nitrogen and makes use of membranes that will tend to have a much higher selectivity in favor of carbon dioxide over methane than nitrogen over methane. If the gas composition is reduced, say, from about 12% to about 4% nitrogen, this means that the carbon dioxide content is reduced proportionately to much lower levels, typically in the ppm range. For pipeline gas, therefore, the gas is brought simultaneously within specification for both inerts without the need for further carbon-dioxide-specific removal treatment.

Even if the nitrogen content of product stream 109 is chosen to be higher than 4%, such as 6% or above, and the raw gas stream contains acid gases and water vapor, stream 109 is generally close to or within pipeline specification for carbon dioxide, hydrogen sulfide and water vapor, because of the much higher selectivity of the membranes for these components over methane. In fact, the carbon dioxide will typically be reduced to ppm levels, even if the raw stream contained as much as 10% carbon dioxide or above, and the water vapor and hydrogen sulfide content will typically be just a few ppm. This is advantageous, as it facilitates blending of this stream with other streams that are more contaminated with these components.

With respect to carbon dioxide, pipeline specification is typically no more than 2%. As just mentioned, the product gas, stream 109, often has a much, much lower carbon dioxide content than this. However, if the raw gas to be treated is only slightly out of specification for nitrogen, say, for example, contains 7% nitrogen, and is heavily contaminated with carbon dioxide, say, for example, contains 30% carbon dioxide, it is possible that reducing the nitrogen content of stream 109 to about 4% leaves enough carbon dioxide in the gas that it fails to meet the 4% total inerts requirement, or that it fails to meet the 2% carbon dioxide requirement.

If the stream is only slightly out of the pipeline or other desired specification for carbon dioxide, such as containing no more than about 3% carbon dioxide, or no more than about 4% or 5% carbon dioxide, for example, it may be possible to pool stream 109 with other gas that has a lower carbon dioxide content before the stream is passed to the pipeline. Thus, in some cases, a carbon dioxide concentration of, for example, about 3%, or even 5% or more, may be acceptable, even if the gas is ultimately destined for a gas pipeline.

Otherwise the process may be operated to produce a stream 109 that meets the total inerts requirement by containing less than 4% nitrogen, such as 3% or 3.5% nitrogen, for example, and carbon dioxide to make up the balance of allowed inerts.

Besides meeting the target composition, stream 109 should preferably contain at least about 70%, more preferably at least about 80%, of the methane content of the feed stream. Stream 109 is withdrawn from the process and passed to the gas pipeline or to any other desired destination.

As mentioned above, the second permeate stream, 108, is enriched in nitrogen and depleted in methane compared with the membrane feed stream, 107. Because the second membrane separation step is relied upon to bring the nitrogen concentration of the product stream down to the target value, the stage-cut needed to accomplish this is typically quite large, such as more than 50% or 60%, so stream 108 may be comparable in volume flow to stream 101. Although stream 108 may be sent to any appropriate destination, simply discharging it from the process is not preferred, since this is likely to result in loss of significant quantities of methane from the product stream.

More preferably, as indicated by the dashed line in FIG. 1, stream 108 is recirculated within the process to increase methane recovery. If this is done, it is most preferred to adjust the membrane areas of steps 113 and 114 as far as possible so that, consistent with the other targets of the process, stream 108 has a nitrogen content roughly the same as that of raw stream 101. This avoids the process inefficiencies associated with contaminating stream 101 with a stream of much higher nitrogen content.

If the feed stream needs to be cooled, it is also optionally possible, and preferred, as shown in the embodiment of FIG. 1, to use stream 108 to cool the incoming membrane feed stream, by passing stream 108 in heat-exchanging relationship against stream 104, as indicated by heat exchange step 112 in FIG. 1.

Figure 2:
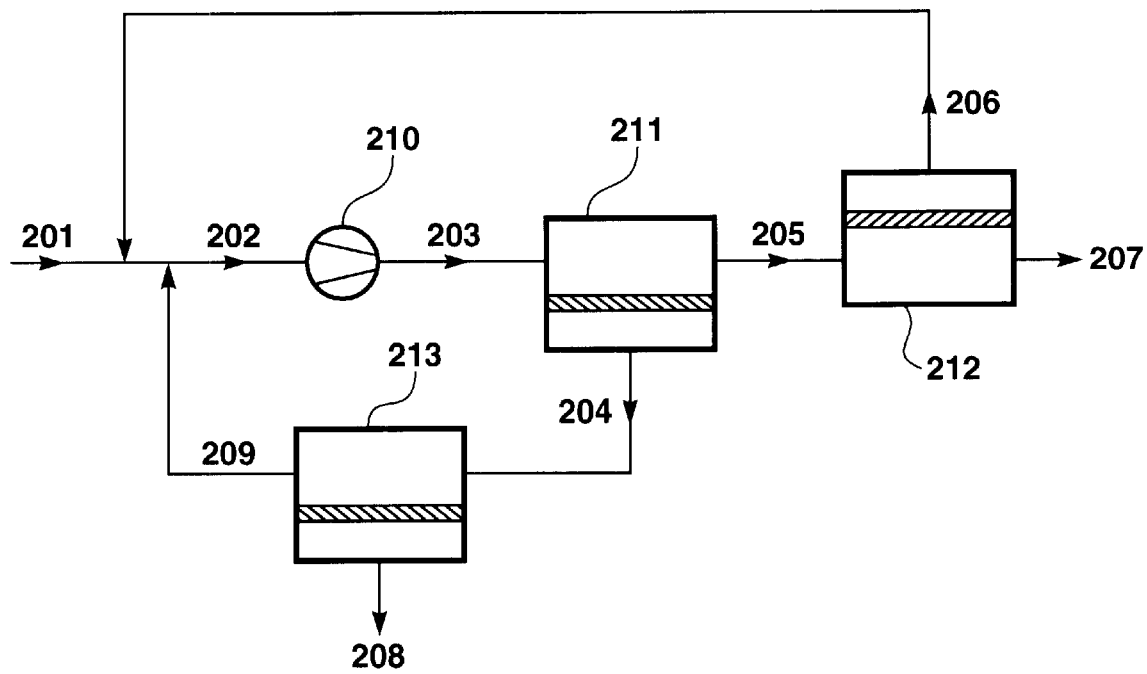
FIG. 2 is a schematic drawing of a preferred embodiment of the invention, including a second membrane stage to treat the permeate stream from the first membrane separation step.

Turning to FIG. 2, this shows a preferred embodiment of the invention in which the permeate stream from the first membrane separation step is subjected to additional treatment, thereby providing the opportunity for increased methane recovery. For simplicity, no heat exchange steps are shown in this figure, although it will be appreciated that they could be incorporated, using, for example, streams 206 and 208 to cool membrane feed stream 203. In FIG. 2, it is again assumed that the raw gas stream in this example requires compression before it can be processed in the membrane separation steps.

Unless otherwise indicated, parameter preferences and comments, such as those relating to membrane type and performance, gas temperatures at the inlets of the individual membrane separation steps, feed and permeate pressures and pressure ratio, and permeate product stream composition, for FIG. 2 are the same as those for FIG. 1.

As before, raw feed stream, 201, maybe any methane-containing gas from which it is desired to remove nitrogen. The raw gas may be as-extracted from the ground or may have been subjected to pretreatment of any kind. Stream 201 usually contains at least about 4% nitrogen, frequently much more. Carbon dioxide, water vapor, hydrogen sulfide and other light hydrocarbons may also be present.

Stream 201 is combined with recirculation streams 206 and 209, described below, to form combined stream, 202. Combined stream 202 passes into compression step, 210, and emerges as compressed stream, 203. Stream 203 is passed on the feed side into membrane separation step, 211. Membrane separation step 211 results in a first residue stream, 205, that is enriched in methane and depleted in nitrogen compared with the membrane feed stream, 203, and a first permeate stream, 204, that is enriched in nitrogen and depleted in methane compared with the membrane feed stream 203. As with the embodiment of FIG. 1, if carbon dioxide, water vapor or hydrogen sulfide are present in the gas, they will pass preferentially into the permeate stream with the nitrogen.

In this case, it is desired to treat stream 204 further to reduce loss of product methane from the process or to recover other components of value from the stream. It is assumed that this additional treatment is carried out by means of a second membrane separation stage, 213. Therefore, first permeate stream 204 is passed as feed to this stage.

FIG. 2 shows no recompression of stream 204 before it is passed into membrane separation stage 213. This is preferred, as the overall process can then operate with only one compression step, 210, as shown. To facilitate operation of the second membrane stage, it is preferred, therefore, to maintain the pressure on the permeate side of first membrane separation step 211 at a relatively high value, such as at least about 100 psia, and more preferably at least about 200 psia, 250 psia or more. Most preferably, the pressure on the permeate side of step 211 is maintained just a few pounds higher than the pressure of the raw stream 201, so that residue stream, 209, discussed below, can be recirculated and mixed with stream 201 without pressure adjustment.

Alternatively, stream 204 may be compressed to any desired pressure before it is passed into membrane separation stage 213. This stage again contains membranes capable of exhibiting a nitrogen/methane selectivity, as measured with a gas mixture containing at least nitrogen and methane, of at least about 2, and preferably in the range about 2–5, at a temperature higher than about −25° C. Other operating parameter preferences and comments, such as those relating to membrane type and performance, temperature, pressure drop and ratio and the like for this stage are similar to those for the membrane separation steps 211 and 212 of the first stage, and the membrane steps 113 and 114 of FIG. 1.

This second stage separates stream 204 into third permeate stream, 208, and third residue stream 209. Stream 208 is enriched in nitrogen compared with stream 204, and thus twice-enriched in this component compared with stream 203. If carbon dioxide, water vapor or hydrogen sulfide is present in the process feed gas, these will also be twice-enriched in stream 208. Typically, therefore, this stream is relatively lean in methane, such as containing no more than about 50% methane, or most preferably no more than about 40% methane.

Because of its high nitrogen and low methane content, in some embodiments of the process third permeate stream 208 is a waste stream, and is simply withdrawn and flared or otherwise disposed of.

In other cases, stream 208 may meet the compositional or Btu requirements for a fuel product and may be used, in whole or in part, to power field equipment as discussed above.

In yet other cases, the nitrogen or carbon dioxide content may be high enough that the gas can be recompressed and injected as a substitute for, or a supplement to, fresh nitrogen or carbon dioxide in fields where nitrogen injection or carbon dioxide injection is being practiced for any reason.

As yet another preferred alternative, stream 208 may be passed to additional treatment, such as to be fractionated into a fuel gas stream and a nitrogen-rich stream.

Membrane separation stage 213 also results in third residue stream, 209, which is enriched in methane and depleted in nitrogen compared with stream 204. This stream is preferably recirculated as shown to the front of the process to improve methane recovery.

Alternatively, stream 209, which is upgraded in methane content compared with stream 208, may be used in whole or in part as fuel gas.

First residue stream 205 is passed as feed to second membrane separation step 212, where it is separated into second permeate stream, 206, and second residue stream, 207. Second residue stream 207, which is further enriched in methane compared with stream 205, is the primary product stream of the process. As with stream 109 in the FIG. 1 embodiment, stream 207 meets the pipeline or other desired specifications for nitrogen, carbon dioxide and water vapor.

Also, as with the embodiment of FIG. 1, stream 207 should preferably contain at least about 70%, more preferably at least about 80%, of the methane content of the feed stream.

Stream 207 is withdrawn from the process and passed to the gas pipeline or to any other desired destination.

Second permeate stream, 206, is withdrawn from step 212 and is recirculated as shown to the front of the process to increase methane recovery.

An important parameter in the FIG. 2 process configuration is the size of the second stage membrane unit. Changing the membrane area of this unit changes the amount of nitrogen in recycle stream 209, which in turn changes the overall methane recovery. For greater efficiency in terms of overall membrane area and compressor horsepower used in the process, it is preferred to adjust the membrane area of unit 213 so that the nitrogen content of stream 209 is very roughly the same as that of stream 201.

On the other hand, if maximum methane recovery is the paramount concern, it is preferred to use a smaller membrane area in unit 213 so that the stage cut for that unit decreases, thereby retaining more methane in the process loop. This trade-off is illustrated in more detail in the Examples section below.

The process scheme of FIG. 2 appears more complicated than that of FIG. 1. However the three membrane units are completely passive devices, and the process as shown uses only one piece of rotating equipment, the main gas compressor.

When challenged with a feed stream of the same composition, the process of FIG. 2 is generally able to achieve relatively high methane recovery compared with the process of FIG. 1, such as at least about 80% and frequently higher, such as at least about 50%. This recovery is achieved by using more membrane area and compressor horsepower than the design of FIG. 1. However, the fuel gas to drive the compressor can generally be obtained without any additional cost from what would otherwise be a waste gas stream of the process.

If a second compressor is acceptable in the process, it is possible, of course, to compress the first permeate stream to a higher pressure before carrying out the second stage separation. If a slightly more complicated membrane configuration and a second compressor are acceptable, recovery results comparable with those of the FIG. 2 embodiment, but using less membrane area and compressor horsepower, can be achieved using an embodiment such as that shown in FIG. 4.

Figure 4:
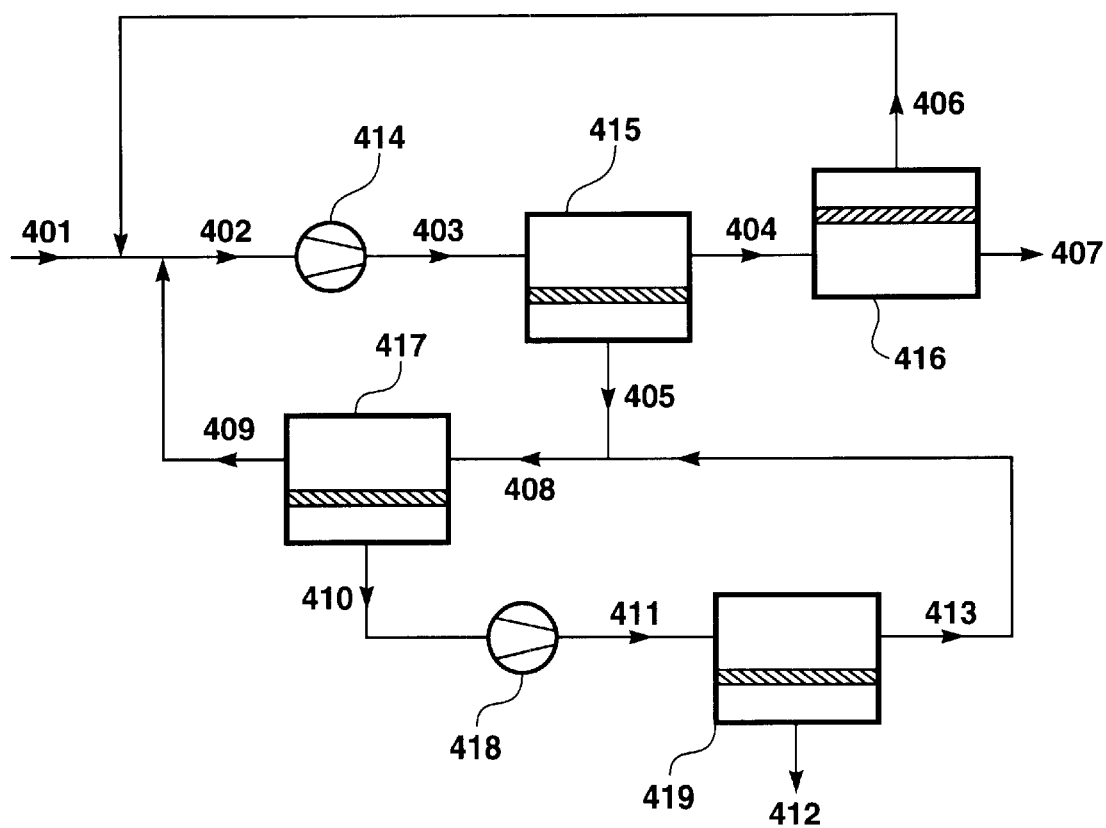
FIG. 4 is a schematic drawing of a second preferred embodiment of the invention, including second and third membrane stages to treat the permeate stream from the first membrane separation step.

Turning now to FIG. 4, this embodiment uses a third membrane separation stage, so that the overall process design involves the use of two membrane separation steps, 415 and 416, in the first stage, and two subsequent stages, 417 and 419, to achieve the desired separation.

Unless otherwise indicated, parameter preferences and comments, such as those relating to membrane type and performance, gas temperatures at the inlets of the individual membrane separation steps, feed and permeate pressures and pressure ratio, and permeate product stream composition, for FIG. 4 are the same as those for FIG. 2.

As before, raw feed stream, 401, may be any methane-containing gas from which it is desired to remove nitrogen, and optionally carbon dioxide, hydrogen sulfide and/or water vapor, and may be as-extracted from the ground or may have been subjected to pretreatment of any kind. Stream 401 usually contains at least about 4% nitrogen, frequently much more, and may contain more than about 2% carbon dioxide, as well as small amounts of water vapor or hydrogen sulfide.

Stream 401 is combined with recirculation streams 406 and 409, described below, to form combined stream, 402. Combined stream 402 passes into compression step, 414, and emerges as compressed stream, 403. Stream 403 is passed on the feed side into first membrane separation step, 415. Membrane separation step 415 results in a first residue stream, 404, that is enriched in methane and depleted in nitrogen compared with the membrane feed stream, 403, and a first permeate stream, 405, that is enriched in nitrogen and depleted in methane compared with the membrane feed stream 403.

First residue stream 404 is passed as feed to second membrane separation step 416, where it is separated into second permeate stream 406 and second residue stream 407. For improved methane recovery, second permeate stream 406 is recirculated to the front of the process to form part of the feed 402 to compression step 414. As discussed above, stream 406 may, optionally, also be used to cool the incoming membrane feed streams as desired.

Second residue stream 407 is the primary product of the process, and typically meets pipeline specification or other target process specification for all of nitrogen, carbon dioxide, hydrogen sulfide and water vapor.

First permeate stream 405 is passed as feed to second membrane separation stage, 417. As with FIG. 2, FIG. 4 shows no recompression of stream 405 before it is passed into membrane separation stage 417. In other words, as with the embodiment of FIG. 2, it is preferred to maintain the pressure on the permeate side of membrane separation step 415 at a relatively high value, such as at least about 100 psia, 200 psia or more, and most preferably at about the same, or slightly higher, pressure as raw stream 401.

Stream 405 is mixed with recycle stream 413, described below, to form the feed, 408, to second membrane separation stage 417. In this stage, stream 408 is separated into third permeate stream, 410, and third residue stream 409.

Stream 410 is enriched in nitrogen compared with stream 408, and thus twice-enriched in this component compared with stream 403. If carbon dioxide, water vapor or hydrogen sulfide is present in the process feed gas, these will also be twice-enriched in stream 410. Typically, therefore, this stream is relatively lean in methane, such as containing between about 40% methane and 55% methane. In this case, this stream may still contain sufficient methane to provide a high enough Btu value for fuel, and a portion of the stream may optionally be withdrawn before it is passed on to the next membrane stage to provide engine fuel to run the compressors.

To provide adequate driving force and pressure ratio across second membrane separation stage 417, the permeate side of this stage is typically maintained at a pressure no higher than about 50 psia. Therefore, before stream 410 is passed into third membrane separation stage, 419, it passes through compression step, 418, where the pressure is raised to an appropriate feed pressure. Most preferably this pressure is about the same as the pressure of stream 405, so that the residue stream can be easily recirculated as shown.

Compressed stream, 411, passes as feed to third membrane separation stage, 419. This stage again contains membranes selective in favor of nitrogen over methane. The operating parameter preferences and comments, such as those relating to membrane type and performance, temperature, pressure drop and ratio and the like for this stage are similar to those for the first and second membrane separation stages.

Stream 411 is separated into fourth permeate stream, 412, and fourth residue stream, 413. The residue stream typically contains at least about 60% methane, and is recirculated and mixed with stream 405 to form the feed stream, 408, to second membrane separation stage 417.

Permeate stream 412 is the process stream most heavily contaminated with nitrogen, and carbon dioxide if present, and typically contains at least about 50% combined nitrogen/carbon dioxide. Thus, this stream typically contains relatively little methane, such as no more than about 50%, and more preferably no more than about 40%, 35% or lower. In this case, the loss of methane associated with discharging stream 412 is relatively small, and the stream is typically directed as a waste stream from the process to flare or other disposal as convenient.

Although the configuration of FIG. 4 is more complicated than that of FIG. 2, it is relatively easy to achieve very high levels of methane recovery, such as 50% or higher, with this process design.

In embodiments such as those of FIGS. 1, 2 and 4, the second permeate stream is recirculated to the compression step. In that case, the pressure on the permeate side of the second membrane separation step is determined by the intake suction pressure of the compression step. Thus, the pressure ratio of the second membrane separation step is determined by the pressure ratio exhaust:intake of the compression step.

If the raw gas stream to be treated by the process is already at comparatively high pressure, such as above about 600 psia, and the compression step raises the gas pressure to only 1,000 psia or 1,200 psia, for example, this results in a pressure ratio of only 2 or less across the second membrane separation step. If a higher pressure ratio is required, the compression step can be split into two compression stages, so that gas can enter the compression step either on the suction side of the lowest stage, or at a point of intermediate pressure.

In this case, the second permeate stream, can be recirculated to the suction side of the lowest compression stage, and is compressed to form a partially compressed gas stream at about the same pressure as the raw gas. The raw gas enters the process and is mixed with this recirculated gas at a pressure-compatible intermediate stage in the compression train. Such a design is discussed in detail in copending application Ser. No. 09/917,478, now U.S. Pat. No. 6,425,267, which is incorporated herein by reference in its entirety.

If the raw gas stream to be treated by the process is at sufficiently high pressure to operate the process satisfactorily without any compression of the raw gas, the initial compression steps 110, 210 or 414 are omitted, and recirculation of the second permeate stream can be accomplished by simply recompressing this stream to a pressure compatible with the incoming raw gas. Thus, designs of this type can also be configured to operate with a single compressor. Such a configuration is also discussed in detail in copending application Ser. No. 09/917,478, now U.S. Pat. No. 6,425,267.

If the raw gas stream to be treated by the processes of the invention contains significant amounts of $C_{3+}$ hydrocarbons, these will be knocked out to some extent if the gas stream is cooled by heat exchange, such as according to the process design of FIG. 1, before the gas enters the membrane modules. The hydrocarbon concentration of the membrane feed gas will also be reduced by recirculation of the hydrocarbon lean permeate stream or streams. Nevertheless, remaining hydrocarbons will tend to be retained on the feed side of the membrane steps with the methane. As a result, the dewpoint temperature along the membrane module train may rise above the operating temperature of the membrane units, and there may be potential for condensation of liquid hydrocarbons within the membrane modules.

As is well known in the art, such a problem can be addressed by heating the gas above the highest dewpoint that is anticipated in the train. Thus, in embodiments where cooling by heat exchange is used, it may be desirable to allow the gas to warm slightly between the heat exchangers and the membrane modules. Substantial heating of the gas, for example above about 30° C., however, has the effect of reducing the nitrogen/methane selectivity of the membranes to an undesirably low level.

Thus, it is preferred, if a problem with hydrocarbon condensation is anticipated, to pretreat the gas to remove the $C_{3+}$ hydrocarbon components to an appropriately low level. This can be done by any convenient technique, such as cooling/condensation. In many cases, it is most economic, and therefore preferred, to use a hydrocarbon-selective membrane separation, optionally in conjunction with condensation. A suitable process is that described in U.S. Pat. Nos. 5,089,033 and 5,199,962, for example.

The invention is now further described by the following examples, which are intended to be illustrative of the invention, but are not intended to limit the scope or underlying principles in any way.

EXAMPLES

Set 1

Basic Embodiment of FIG. 1

A series of computer calculations were performed with a modeling program, ChemCad V (ChemStations, Inc., Houston, Tex.), to illustrate a basic two-step membrane separation process for producing a pipeline-quality gas product from a nitrogen-contaminated gas stream.

Example 1

A calculation was performed to illustrate a basic two-step membrane separation process. The process was assumed to be carried out as shown in FIG. 1. It was assumed that second membrane permeate stream 108 is used as coolant in heat exchanger 112, then is recycled to the front of the process for further methane recovery. Second membrane residue stream 109 is withdrawn at pressure as the methane product.

The flow rate of the raw gas was assumed to be 10 MMscfd, and the gas was assumed to contain 75% methane, 15% nitrogen, 9.9% carbon dioxide, 0.1% water vapor, and 100 ppm (parts per million) hydrogen sulfide. The raw gas was assumed to be at 200 psia and 20° C., and to be compressed to 1,200 psia in compressor 110. The permeate sides of both membrane steps were assumed to be maintained at 200 psia.

The process was assumed to be carried out using in both membrane separation steps a membrane providing a selectivity for nitrogen over methane of 2.5, for carbon dioxide over methane of 20, for hydrogen sulfide over methane of 20, and for water vapor over methane of 25. The stream numbers correspond to FIG. 1. The results of the calculations are summarized in Table 2.

TABLE 2

| Stream | 101 | 102 | 103 | 105 | 106 | 107 | 108 | 109 |
|---|---|---|---|---|---|---|---|---|
| Mass flow (lb/h) | 2,392 | 4,295 | 4,295 | 4,295 | 1,683 | 2,612 | 1,903 | 709 |
| Flow (MMscfd) | 10.0 | 18.9 | 18.9 | 18.9 | 6.3 | 12.6 | 8.9 | 3.7 |
| Temp. (° C.) | 20 | 18 | 25 | 9 | 3 | −3 | −16 | −28 |
| Pressure (psia) | 200 | 200 | 1,200 | 1,200 | 200 | 1,200 | 200 | 1,200 |
| Component (mol %): | | | | | | | | |
| Nitrogen | 15.0 | 15.0 | 15.0 | 15.0 | 21.4 | 11.8 | 15.0 | 4.0 |
| Methane | 75.0 | 78.7 | 78.7 | 78.7 | 62.7 | 86.7 | 82.8 | 96.0 |
| Carbon Dioxide | 9.9 | 6.2 | 6.2 | 6.2 | 15.7 | 1.5 | 2.2 | 137 ppm |
| Water | 0.1 | 0.1 | 0.1 | 0.1 | 0.2 | 15 ppm | 22 ppm | 1 ppm |
| Hydrogen Sulfide | 100 ppm | 63 ppm | 63 ppm | 63 ppm | 159 ppm | 15 ppm | 22 ppm | 0 ppm |

Membrane area = 990 m² (360 + 630)
Theoretical horsepower = 1,940 hp

The process yielded 3.7 MMscfd of gas as second residue product stream 109, containing 4% nitrogen, 137 ppm carbon dioxide, and 1 ppm water vapor. Thus, the gas meets pipeline specification for all components. However, the methane recovery is poor, at only 47%.

Example 2

Another calculation was performed based on the process configuration of FIG. 1. In this case, the gas was assumed to contain 64% methane, 6% nitrogen, and 30% carbon dioxide. The flow rate of the raw gas was assumed to be 10 MMscfd. The raw gas was assumed to be at 200 psia and 50° C., and to be compressed to 1,200psia in compressor 110. The permeate side of membrane unit 113 was assumed to be maintained at 50 psia, and membrane unit 114 at 200 psia. For simplicity of the calculation, heat exchange was eliminated.

The process was assumed to be carried out using in both membrane separation steps a membrane providing a selectivity for nitrogen over methane of 2.5 and for carbon dioxide over methane of 20. The stream numbers correspond to FIG. 1. The results of the calculations are summarized in Table 3.

TABLE 3

| Stream | 101 | 102 | 105 | 106 | 107 | 108 | 109 |
|---|---|---|---|---|---|---|---|
| Flow (MMscfd) | 10.0 | 14.4 | 14.4 | 5.3 | 9.1 | 4.3 | 4.7 |
| Temp. (° C.) | 50 | 34 | 25 | 15 | 6 | −4 | −13 |
| Pressure (psia) | 200 | 200 | 1,200 | 50 | 1,200 | 200 | 1,200 |
| Component (mol %): | | | | | | | |
| Nitrogen | 6.0 | 7.4 | 7.4 | 7.8 | 7.1 | 10.5 | 3.9 |
| Methane | 64.0 | 70.6 | 70.6 | 35.4 | 91.1 | 85.9 | 96.0 |
| Carbon Dioxide | 30.0 | 22.0 | 22.0 | 56.8 | 1.8 | 3.7 | 0.1 |

Membrane area = 461 m² (150 + 311)
Theoretical horsepower = 1,541 hp

The process yielded 4.7 MMscfd of gas as second residue product stream 109, containing 3.9% nitrogen and 0.1% carbon dioxide, which meets specification for pipeline quality gas. The methane recovery is good, at 71%.

Example 3

The calculation of Example 2 was repeated, this time assuming the gas to contain 72% methane, 8% nitrogen, and 20% carbon dioxide. All other process parameters were assumed to be as in Example 2. The stream numbers correspond to FIG. 1. The results of the calculations are summarized in Table 4.

TABLE 4

| Stream | 101 | 102 | 105 | 106 | 107 | 108 | 109 |
|---|---|---|---|---|---|---|---|
| Flow (MMscfd) | 10.0 | 19.3 | 19.3 | 4.6 | 14.8 | 9.3 | 5.4 |
| Temp. (° C.) | 50 | 28 | 25 | 19 | 13 | 4 | −6 |
| Pressure (psia) | 200 | 200 | 1,200 | 50 | 1,200 | 200 | 1,200 |
| Component (mol %): | | | | | | | |
| Nitrogen | 8.0 | 10.3 | 10.3 | 12.7 | 9.6 | 12.9 | 4.0 |
| Methane | 72.0 | 77.7 | 77.7 | 43.5 | 88.3 | 83.8 | 96.0 |
| Carbon Dioxide | 20.0 | 12.0 | 12.0 | 43.7 | 2.1 | 3.3 | 462 ppm |

Membrane area = 819 m² (160 + 659)
Theoretical horsepower = 2,047 hp

The process yielded 5.4 MMscfd of gas as second residue product stream 109, containing 4% nitrogen and 462 ppm carbon dioxide, which meets pipeline specification. The methane recovery is good, at over 72%.

Examples 1–3 show that the very simple two-step process of FIG. 1 is able to produce pipeline quality gas from raw streams of diverse compositions, even those that contain large quantities of carbon dioxide. If the nitrogen content is high, however, it is more difficult to obtain good methane recovery.

Set 2

Embodiment of FIG. 2

Example 4

A series of calculations were performed with a modeling program, ChemCad V to illustrate the ability of the process configuration of FIG. 2 to provide increased methane recovery for streams with relatively heavy levels of contaminants.

The flow rate of the raw gas was assumed to be 10 MMscfd, and the gas was assumed to contain 75% methane, 15% nitrogen, 9.9% carbon dioxide, 0.1% water vapor, and 100 ppm hydrogen sulfide, as in Example 1. The raw gas was assumed to be at 200 psia and 20° C., and to be compressed to 1,200 psia in compressor 210. The membrane selectivity for all membrane units was assumed to be as follows:

nitrogen/methane: 2.5
carbon dioxide/methane: 20
hydrogen sulfide/methane: 20
water vapor/methane: 25

The stream numbers correspond to FIG. 2. The results of the calculations are summarized in Table 5.

pipeline specification for all components. However, in this process, the product stream is 6.6 MMscfd, and the methane recovery is 84%.

Example 5

The calculation of Example 4 was repeated, except with a larger membrane area in the second-stage unit, 213, that is, a larger stage-cut in the second-stage membrane unit. All other process parameters were assumed to be as in Example 4. The stream numbers correspond to FIG. 2. The results of the calculations are summarized in Table 6.

TABLE 6

| Stream | 201 | 202 | 203 | 204 | 205 | 206 | 207 | 208 | 209 |
|---|---|---|---|---|---|---|---|---|---|
| Flow (MMscfd) | 10.0 | 32.3 | 32.3 | 8.2 | 24.2 | 18.3 | 6.0 | 4.1 | 4.1 |
| Temp. (° C.) | 20 | 11 | 25 | 21 | 17 | 5 | −8 | 19 | 17 |
| Pressure (psia) | 200 | 200 | 1,200 | 200 | 1,200 | 200 | 1,200 | 20 | 200 |
| Component (mol %): | | | | | | | | | |
| Nitrogen | 15.0 | 16.4 | 16.4 | 24.4 | 13.7 | 16.8 | 4.0 | 30.8 | 18.0 |
| Methane | 75.0 | 79.3 | 79.3 | 63.2 | 84.8 | 81.2 | 96.0 | 44.9 | 81.6 |
| Carbon Dioxide | 9.9 | 4.3 | 4.3 | 12.3 | 1.5 | 2.0 | 67 ppm | 24.0 | 0.5 |
| Water | 0.1 | 417 ppm | 417 ppm | 0.1 | 140 ppm | 185 ppm | 0 | 0.2 | 33 ppm |
| Hydrogen Sulfide | 100 ppm | 43 ppm | 43 ppm | 124 ppm | 15 ppm | 20 ppm | 0 | 243 ppm | 5 ppm |

Membrane area = 2,810 m² (480 + 1,270 + 1,060)
Theoretical horsepower = 3,260 hp

TABLE 5

| Stream | 201 | 202 | 203 | 204 | 205 | 206 | 207 | 208 | 209 |
|---|---|---|---|---|---|---|---|---|---|
| Flow (MMscfd) | 10.0 | 48.0 | 48.0 | 8.6 | 39.4 | 32.9 | 6.6 | 3.5 | 5.2 |
| Temp. (° C.) | 20 | 12 | 25 | 23 | 20 | 8 | −5 | 21 | 20 |
| Pressure (psia) | 200 | 200 | 1,200 | 200 | 1,200 | 200 | 1,200 | 20 | 200 |
| Component (mol %): | | | | | | | | | |
| Nitrogen | 15.0 | 20.4 | 20.4 | 30.2 | 18.3 | 21.2 | 4.0 | 36.0 | 26.4 |
| Methane | 75.0 | 75.7 | 75.7 | 57.4 | 79.8 | 76.5 | 96.0 | 35.1 | 72.2 |
| Carbon Dioxide | 9.9 | 3.8 | 3.8 | 12.2 | 1.9 | 2.3 | 19 ppm | 28.6 | 1.3 |
| Water | 0.1 | 362 ppm | 362 ppm | 0.1 | 175 ppm | 210 ppm | 0 | 0.3 | 100 ppm |
| Hydrogen Sulfide | 100 ppm | 38 ppm | 38 ppm | 124 ppm | 19 ppm | 23 ppm | 0 | 289 ppm | 13 ppm |

Membrane area = 3,460 m² (480 + 2,210 + 770)
Theoretical horsepower = 4,860 hp

As with the two-step process of Example 1, this process yielded a second residue product stream, 207, containing only 4% nitrogen and 19 ppm carbon dioxide, which meets With the larger second-stage membrane area, the process yielded slightly less product, only 6.0 MMscfd (stream 207), again containing 4% nitrogen and 67 ppm carbon dioxide.

The methane recovery was reduced to 76%. The compressor horsepower requirement and the total membrane area requirement were less than in Example 4.

Example 6

The calculation of Example 4 was repeated, except with a still-larger membrane area in the second-stage unit, 213. All other process parameters were assumed to be as in Example 4. The stream numbers correspond to FIG. 2. The results of the calculations are summarized in Table 7.

TABLE 7

| Stream | 201 | 202 | 203 | 204 | 205 | 206 | 207 | 208 | 209 |
|---|---|---|---|---|---|---|---|---|---|
| Flow (MMscfd) | 10.0 | 24.4 | 24.4 | 8.0 | 16.4 | 11.2 | 5.2 | 4.8 | 3.2 |
| Temp. (° C.) | 20 | 11 | 25 | 20 | 15 | 2 | −10 | 17 | 14 |
| Pressure (psia) | 200 | 200 | 1,200 | 200 | 1,200 | 200 | 1,200 | 20 | 200 |
| Component (mol %): | | | | | | | | | |
| Nitrogen | 15.0 | 14.4 | 14.4 | 21.1 | 11.1 | 14.4 | 4.0 | 26.9 | 12.4 |
| Methane | 75.0 | 80.7 | 80.7 | 66.4 | 87.7 | 83.9 | 96.0 | 52.4 | 87.5 |
| Carbon Dioxide | 9.9 | 4.9 | 4.9 | 12.4 | 1.2 | 1.7 | 144 ppm | 20.5 | 0.1 |
| Water | 0.1 | 483 ppm | 483 ppm | 0.1 | 108 ppm | 157 ppm | 1 ppm | 0.2 | 8 ppm |
| Hydrogen Sulfide | 100 ppm | 49 ppm | 49 ppm | 125 ppm | 12 ppm | 18 ppm | 0 | 208 ppm | 1 ppm |

Membrane area = 2,640 m$^2$ (480 + 800 + 1,360)
Theoretical horsepower = 2,440 hp With the still-larger second-stage membrane area, the process again yielded slightly less product, only 5.2 MMscfd (stream 207), containing 4% nitrogen, 144 ppm carbon dioxide, and 1 ppm water vapor. The methane recovery was down to 66%. The compressor horsepower requirement and the total membrane area requirement were less than in Examples 4 and 5.

Example 7

The calculation of Example 4 was repeated, except with a smaller membrane area in the second-stage unit, 213, that is, the calculation was done at a smaller stage-cut in the second-stage membrane unit than in Example 4. All other process parameters were assumed to be as in Example 4. The stream numbers correspond to FIG. 2. The results of the calculations are summarized in Table 8.

Example 8

The calculation of Example 4 was repeated. In this case, however, it was assumed that a second compressor was used to recompress first permeate stream 204 to 1,200 psia before passing it to second membrane separation stage 213. The pressure on the permeate side of membrane separation unit 211 could then be at a lower pressure than the 200 psia of the previous examples. For this calculation, the permeate pressure was assumed to be 100 psia, doubling the pressure ratio across membrane separation unit 211, and providing a much higher pressure ratio across second membrane separation stage 213. Since residue stream 209 is now at high pressure, it was assumed to be recirculated to rejoin the incoming feed after compression step 210, rather than before, reducing the compression capacity needed in this step. The stream numbers correspond to FIG. 2. The results of the calculations are summarized in Table 9.

TABLE 8

| Stream | 201 | 202 | 203 | 204 | 205 | 206 | 207 | 208 | 209 |
|---|---|---|---|---|---|---|---|---|---|
| Flow (MMscfd) | 10.0 | 85.5 | 85.5 | 9.5 | 75.9 | 68.8 | 7.1 | 2.8 | 6.7 |
| Temp. (° C.) | 20 | 12 | 25 | 24 | 22 | 10 | −3 | 22 | 21 |
| Pressure (psia) | 200 | 200 | 1,200 | 200 | 1,200 | 200 | 1,200 | 20 | 200 |
| Component (mol %): | | | | | | | | | |
| Nitrogen | 15.0 | 28.5 | 28.5 | 40.3 | 27.0 | 29.4 | 4.0 | 41.9 | 39.6 |
| Methane | 75.0 | 67.9 | 67.9 | 46.9 | 70.5 | 67.9 | 96.0 | 23.1 | 57.1 |
| Carbon Dioxide | 9.9 | 3.5 | 3.5 | 12.6 | 2.4 | 2.6 | 2 ppm | 34.6 | 3.2 |
| Water | 0.1 | 328 ppm | 328 ppm | 0.1 | 215 ppm | 238 ppm | 0 | 0.4 | 257 ppm |
| Hydrogen Sulfide | 100 ppm | 36 ppm | 36 ppm | 128 ppm | 24 ppm | 27 ppm | 0 | 350 ppm | 33 ppm |

Membrane area = 5,350 m$^2$ (480 + 4,350 + 520)
Theoretical horsepower = 8,730 hp With the smaller second-stage membrane area (smaller stage-cut) than in Example 4, the process yielded 7.1 MMscfd (stream 207), containing 4% nitrogen and only 2 ppm carbon dioxide. The methane recovery was nearly 91%. However, the compressor horsepower requirement and the total membrane area requirement were approximately 1.8 and 1.6 times those in Example 4, respectively.

TABLE 9

| Stream | 201 | 203 | 204 | compressed 204 | 205 | 206 | 207 | 208 | 209 |
|---|---|---|---|---|---|---|---|---|---|
| Flow (MMscfd) | 10.0 | 40.0 | 11.3 | 11.3 | 28.8 | 22.2 | 6.5 | 3.5 | 7.8 |
| Temp. (° C.) | 25 | 25 | 21 | 30 | 17 | 4 | −8 | 24 | 17 |
| Pressure (psia) | 200 | 1,200 | 100 | 1,200 | 1,200 | 200 | 1,200 | 20 | 1,200 |
| Component (mol %): | | | | | | | | | |
| Nitrogen | 15.0 | 18.7 | 29.0 | 29.0 | 14.7 | 17.9 | 4.0 | 35.8 | 26.0 |
| Methane | 75.0 | 78.3 | 61.7 | 61.7 | 84.9 | 81.6 | 96.0 | 35.3 | 73.3 |
| Carbon Dioxide | 9.9 | 2.8 | 9.1 | 9.1 | 0.4 | 0.5 | 13 ppm | 28.6 | 0.5 |
| Water | 0.1 | 0.1 | 0.2 | 0.2 | 82 ppm | 105 ppm | 0 | 0.3 | 0.2 |
| Hydrogen Sulfide | 100 ppm | 29 ppm | 92 ppm | 92 ppm | 4 ppm | 5 ppm | 0 | 289 ppm | 5 ppm |

Membrane area = 2,281 m² (600 + 1,562 + 119)
Theoretical horsepower = 5,051 hp (3,242 + 1,809)

The process yielded 6.5 MMscfd, containing 4% nitrogen and 13 ppm carbon dioxide. The methane recovery was 84%.

Example 9

The results of the calculations of Examples 1 and 4–8 are summarized in Table 10.

TABLE 10

| | Parameter | | | | |
|---|---|---|---|---|---|
| | Second-Stage Stage-Cut | Methane Recovery | Methane Recovery | Membrane Area (m²) | | Theoretical Compressor |
| Example # | (%) | (%) | (MMscfd) | Second-Stage | Total | Horsepower |
| Example 1 | — | 47.0 | 3.7 | — | 990 | 1,940 |
| Example 4 | 40 | 84 | 6.6 | 770 | 3,460 | 4,860 |
| Example 5 | 50 | 76 | 6.0 | 1,060 | 2,810 | 3,260 |
| Example 6 | 60 | 66 | 5.2 | 1,360 | 2,640 | 2,440 |
| Example 7 | 30 | 91 | 7.1 | 520 | 5,350 | 8,730 |
| Example 8 | 30 | 84 | 6.5 | 119 | 2,281 | 5,051 |

Figure 3:
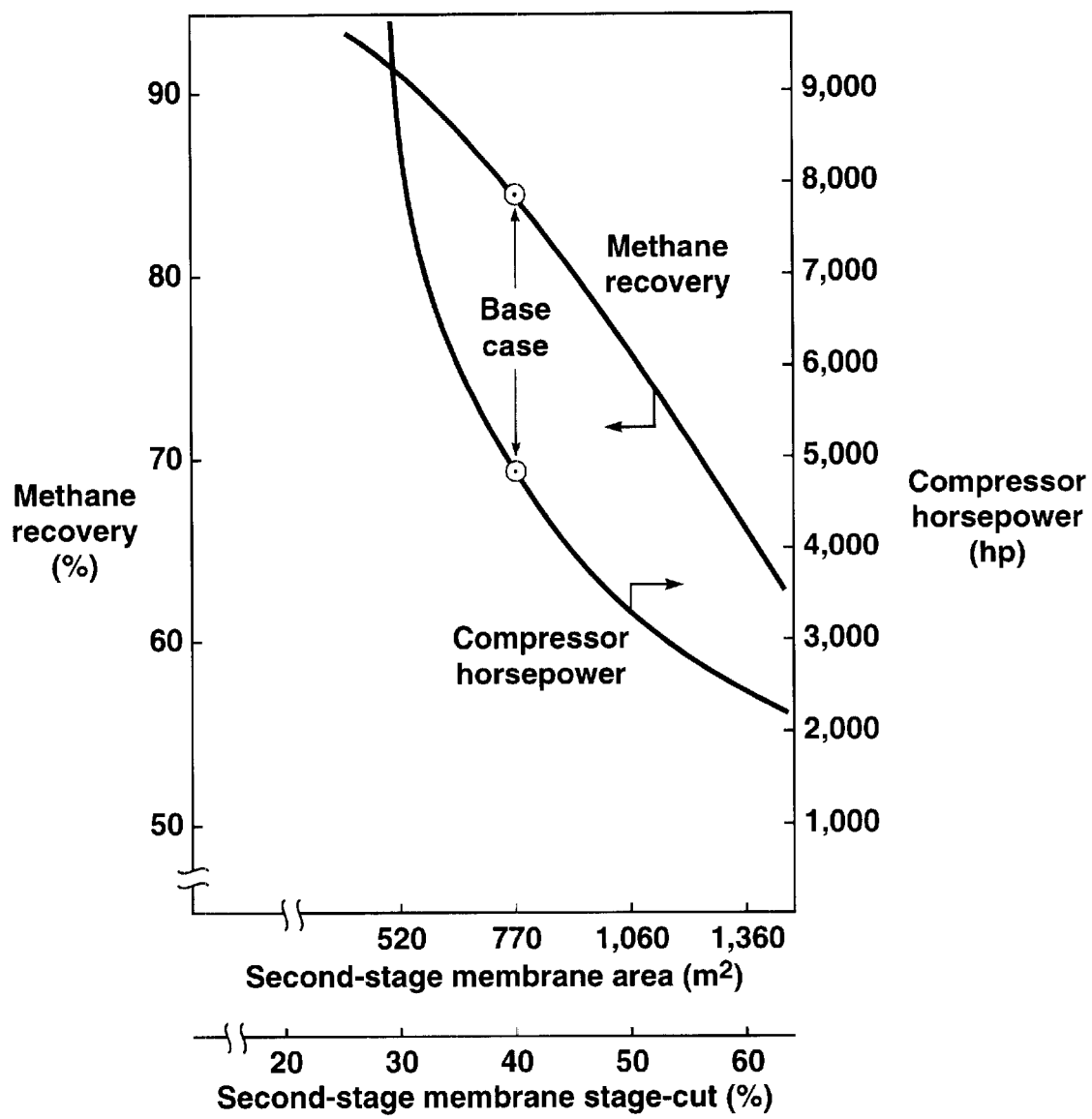
FIG. 3 is a graph of performance calculations for the embodiment of FIG. 2.

This same information is presented graphically in FIG. 3, which shows the relationship between the stage-cut (or membrane area) of the second-stage membrane, and the compressor horsepower requirement and the methane recovery of the overall process. As can be seen, the smaller is the membrane area, and hence stage-cut, in the second membrane separation stage, the more gas is held back and recirculated in the process loop, increasing methane recovery, but also leading to an increase in overall membrane area and horsepower needed to achieve the separation.

Also, comparing the results of Examples 4 and 8, it can be seen that the process of Example 8 uses the same amount of compressor horsepower, but 35% less membrane area to achieve the same methane recovery. The process of Example 8 has the significant disadvantage of requiring a second compressor, however.

Set 3

Embodiment of FIG. 4

Example 10

A series of calculations were performed with a modeling program, ChemCad V, to illustrate the ability of the process configuration of FIG. 4 to achieve very high levels of methane recovery.

The flow rate of the raw gas was assumed to be 10 MMscfd, and the gas was assumed to contain 75% methane, 15% nitrogen, 9.9% carbon dioxide, 0.1% water vapor, and 100 ppm hydrogen sulfide. The raw gas was assumed to be at 200 psia and 25° C., and to be compressed to 1,200 psia in compressor 414. The permeate sides of membrane units 415 and 416 were assumed to be maintained at 200 psia, and the permeate sides of membrane units 417 and 419 at 20 psia. The membrane selectivity for all membrane units was assumed to be as follows:

nitrogen/methane: 2.5 carbon dioxide/methane: 20 hydrogen sulfide/methane: 20 water vapor/methane: 25

The stream numbers correspond to FIG. 4. The results of the calculations are summarized in Table 11.

TABLE 11

| Stream | 401 | 402 | 403 | 404 | 405 | 406 | 407 | 408 | 409 | 410 | 412 | 413 |
|---|---|---|---|---|---|---|---|---|---|---|---|---|
| Flow (MMscfd) | 10.0 | 34.8 | 34.8 | 26.3 | 8.5 | 19.8 | 6.5 | 10.4 | 5.1 | 5.4 | 3.4 | 1.9 |
| Temp. (° C.) | 20 | 13 | 25 | 18 | 22 | 6 | −6 | 21 | 17 | 19 | 22 | 20 |
| Pressure (psia) | 200 | 200 | 1,200 | 1,200 | 200 | 200 | 1,200 | 200 | 200 | 20 | 20 | 200 |
| Component (mol %): | | | | | | | | | | | | |
| Nitrogen | 15.0 | 16.0 | 16.0 | 13.5 | 11.8 | 16.6 | 4.0 | 23.7 | 16.0 | 31.0 | 35.9 | 22.2 |
| Methane | 75.0 | 79.9 | 79.9 | 85.0 | 64.0 | 81.4 | 96.0 | 66.5 | 83.7 | 50.3 | 35.1 | 77.6 |
| Carbon Dioxide | 9.9 | 4.0 | 4.0 | 1.5 | 24.1 | 2.0 | 71 ppm | 9.7 | 0.3 | 18.5 | 28.7 | 0.2 |
| Water | 0.1 | 394 ppm | 394 ppm | 138 ppm | 0.1 | 184 ppm | 0 | 0.1 | 18 ppm | 0.2 | 0.3 | 11 ppm |
| Hydrogen Sulfide | 100 ppm | 41 ppm | 41 ppm | 15 ppm | 119 ppm | 20 ppm | 0 | 98 ppm | 3 ppm | 187 ppm | 290 ppm | 2 ppm |

Membrane area = 4,150 m² (500 + 1,380 + 1,500 + 770)
Theoretical horsepower = 4,350 hp (3,570 + 780)

As with the other processes described above with respect to FIGS. 1 and 2, this process yielded a second residue product stream, 407, containing only 4% nitrogen and 71 ppm carbon dioxide, which meets pipeline specification. In this process, the product stream is 6.5 MMscfd, and the methane recovery is nearly 84%, comparable to the results obtained in Example 2. Although the compressor horsepower requirement is about 10% less than in Example 2, the total membrane area requirement is about 20% more.

Example 11

The calculation of Example 10 was repeated, except with a smaller membrane area in the third-st age unit, 419. All other process parameters were assumed to be as in Example 10. The stream numbers correspond to FIG. 4. The results of the calculations are summarized in Table 12.

TABLE 12

| Stream | 401 | 402 | 403 | 404 | 405 | 406 | 407 | 408 | 409 | 410 | 412 | 413 |
|---|---|---|---|---|---|---|---|---|---|---|---|---|
| Flow (MMscfd) | 10.0 | 39.6 | 39.6 | 31.0 | 8.6 | 24.2 | 6.8 | 10.9 | 5.4 | 5.5 | 3.2 | 2.3 |
| Temp. (° C.) | 20 | 13 | 25 | 19 | 22 | 7 | −6 | 22 | 19 | 20 | 23 | 20 |
| Pressure (psia) | 200 | 200 | 1,200 | 1,200 | 200 | 200 | 1,200 | 200 | 200 | 20 | 20 | 200 |
| Component (mol %): | | | | | | | | | | | | |
| Nitrogen | 15.0 | 17.3 | 17.3 | 14.8 | 25.9 | 17.9 | 4.0 | 26.4 | 18.5 | 34.2 | 38.5 | 28.4 |
| Methane | 75.0 | 78.9 | 78.9 | 83.5 | 62.3 | 80.0 | 96.0 | 64.2 | 81.2 | 47.4 | 30.0 | 71.1 |
| Carbon Dioxide | 9.9 | 3.8 | 3.8 | 1.6 | 11.7 | 2.1 | 47 ppm | 9.3 | 0.3 | 18.2 | 31.1 | 0.5 |
| Water | 0.1 | 372 ppm | 372 ppm | 149 ppm | 0.1 | 191 ppm | 0 | 0.1 | 21 ppm | 0.2 | 0.3 | 31 ppm |
| Hydrogen Sulfide | 100 ppm | 38 ppm | 38 ppm | 16 ppm | 118 ppm | 21 ppm | 0 | 94 ppm | 3 ppm | 184 ppm | 315 ppm | 5 ppm |

Membrane area = 4,330 m² (500 + 1,670 + 1,500 + 660)
Theoretical horsepower = 4,870 hp (4,070 + 800)

As in Example 10, the process yielded a second residue product stream, 407, containing only 4% nitrogen and 47 ppm carbon dioxide. The product stream is 6.8 MMscfd, and the methane recovery is over 87%, a better overall result than in Example 10. However, this improvement requires about 5% more membrane area and about 12% more compressor horsepower than in Example 10.

Example 12

The calculation of Example 10 was repeated, except with a still smaller membrane area in the third-stage unit, 419. All other process parameters were assumed to be as in Example 10. The stream numbers correspond to FIG. 4. The results of the calculations are summarized in Table 13.

TABLE 13

| Stream | 401 | 402 | 403 | 404 | 405 | 406 | 407 | 408 | 409 | 410 | 412 | 413 |
|---|---|---|---|---|---|---|---|---|---|---|---|---|
| Flow (MMscfd) | 10.0 | 46.0 | 46.0 | 37.2 | 8.8 | 30.2 | 7.0 | 11.5 | 5.8 | 5.7 | 2.9 | 2.7 |
| Temp. (° C.) | 20 | 13 | 25 | 20 | 23 | 8 | −5 | 22 | 19 | 21 | 23 | 21 |
| Pressure (psia) | 200 | 200 | 1,200 | 1,200 | 200 | 200 | 1,200 | 200 | 200 | 20 | 20 | 200 |
| Component (mol %): | | | | | | | | | | | | |
| Nitrogen | 15.0 | 18.9 | 18.9 | 16.7 | 28.3 | 19.6 | 4.0 | 29.9 | 21.8 | 38.2 | 41.1 | 35.1 |
| Methane | 75.0 | 77.5 | 77.5 | 81.6 | 60.1 | 78.2 | 96.0 | 61.0 | 77.8 | 43.7 | 25.0 | 63.9 |
| Carbon Dioxide | 9.9 | 3.6 | 3.6 | 1.7 | 11.5 | 2.1 | 28 ppm | 9.0 | 0.3 | 17.9 | 33.5 | 1.0 |
| Water | 0.1 | 349 ppm | 349 ppm | 160 ppm | 0.01 | 197 ppm | 0 | 0.1 | 24 ppm | 0.2 | 0.3 | 66 ppm |
| Hydrogen Sulfide | 100 ppm | 36 ppm | 36 ppm | 17 ppm | 116 ppm | 21 ppm | 0 | 91 ppm | 3 ppm | 181 ppm | 339 ppm | 10 ppm |

Membrane area = 4,620 m² (500 + 2,060 + 1,500 + 560)
Theoretical horsepower = 5,560 hp (4,730 + 830)

As in Example 10, the process yielded a second residue product stream, 407, containing only 4% nitrogen and 28 ppm carbon dioxide. The product stream is 7.0 MMscfd, and the methane recovery is 90%, a better overall result than in Examples 10 and 11. However, this improvement requires about 12% more membrane area and nearly 30% more compressor horsepower than are required in Example 10.

Example 13

The calculation of Example 10 was repeated, except with a still smaller membrane area in the third-stage unit, 419. All other process parameters were assumed to be as in Example 10. The streams numbers correspond to FIG. 4. The results of the calculations are summarized in Table 14.

TABLE 14

| Stream | 401 | 402 | 403 | 404 | 405 | 406 | 407 | 408 | 409 | 410 | 412 | 413 |
|---|---|---|---|---|---|---|---|---|---|---|---|---|
| Flow (MMscfd) | 10.0 | 55.4 | 55.4 | 46.4 | 9.0 | 39.1 | 7.2 | 12.2 | 6.2 | 6.0 | 2.8 | 3.2 |
| Temp. (° C.) | 20 | 13 | 25 | 21 | 23 | 9 | −4 | 23 | 20 | 21 | 23 | 21 |
| Pressure (psia) | 200 | 200 | 1,200 | 1,200 | 200 | 200 | 1,200 | 200 | 200 | 20 | 20 | 200 |
| Component (mol %): | | | | | | | | | | | | |
| Nitrogen | 15.0 | 21.3 | 21.3 | 19.3 | 31.6 | 22.1 | 4.0 | 34.5 | 26.3 | 43.1 | 43.7 | 42.7 |
| Methane | 75.0 | 75.3 | 75.3 | 78.9 | 57.0 | 75.7 | 96.0 | 56.6 | 73.3 | 39.1 | 20.0 | 55.5 |
| Carbon Dioxide | 9.9 | 3.4 | 3.4 | 1.8 | 11.2 | 2.2 | 14 ppm | 8.8 | 0.4 | 17.5 | 35.9 | 1.8 |
| Water | 0.1 | 326 ppm | 326 ppm | 170 ppm | 0.1 | 201 ppm | 0 | 0.1 | 26 ppm | 0.2 | 0.4 | 124 ppm |
| Hydrogen Sulfide | 100 ppm | 34 ppm | 34 ppm | 18 ppm | 114 ppm | 22 ppm | 0 | 89 ppm | 4 ppm | 177 ppm | 363 ppm | 18 ppm |

Membrane area = 5,100 m² (500 + 2,630 + 1,500 + 480)
Theoretical horsepower = 6,580 hp (5,700 + 880)

As in Example 10, the process yielded a second residue product stream, 407, containing only 4% nitrogen and 14 ppm carbon dioxide. The product stream is 7.2 MMscfd, and the methane recovery is over 92%, a better overall result than in Examples 10–12. However, this improvement requires about 23% more membrane area and more than 50% more compressor horsepower than are required in Example 10.

Example 14

The results of the calculations of Examples 7 and 10–13 are summarized in Table 15.

TABLE 15

| Parameter▶<br>Example #▼ | Third-Stage<br>Stage-Cut<br>(%) | Methane<br>Recovery<br>(%) | Methane<br>Recovery<br>(MMscfd) | Membrane Area (m²) | | Theoretical<br>Compressor<br>Horsepower |
|---|---|---|---|---|---|---|
| | | | | Third-Stage | Total | |
| Example 10 | 64 | 84 | 6.5 | 770 | 4,150 | 4,350 |
| Example 11 | 58 | 87 | 6.8 | 660 | 4,330 | 4,870 |
| Example 12 | 52 | 90 | 7.0 | 560 | 4,620 | 5,560 |
| Example 13 | 46 | 92 | 7.2 | 480 | 5,110 | 6,580 |
| Example 7 | — | 91 | 7.1 | — | 5,350 | 8,730 |

Figure 5:
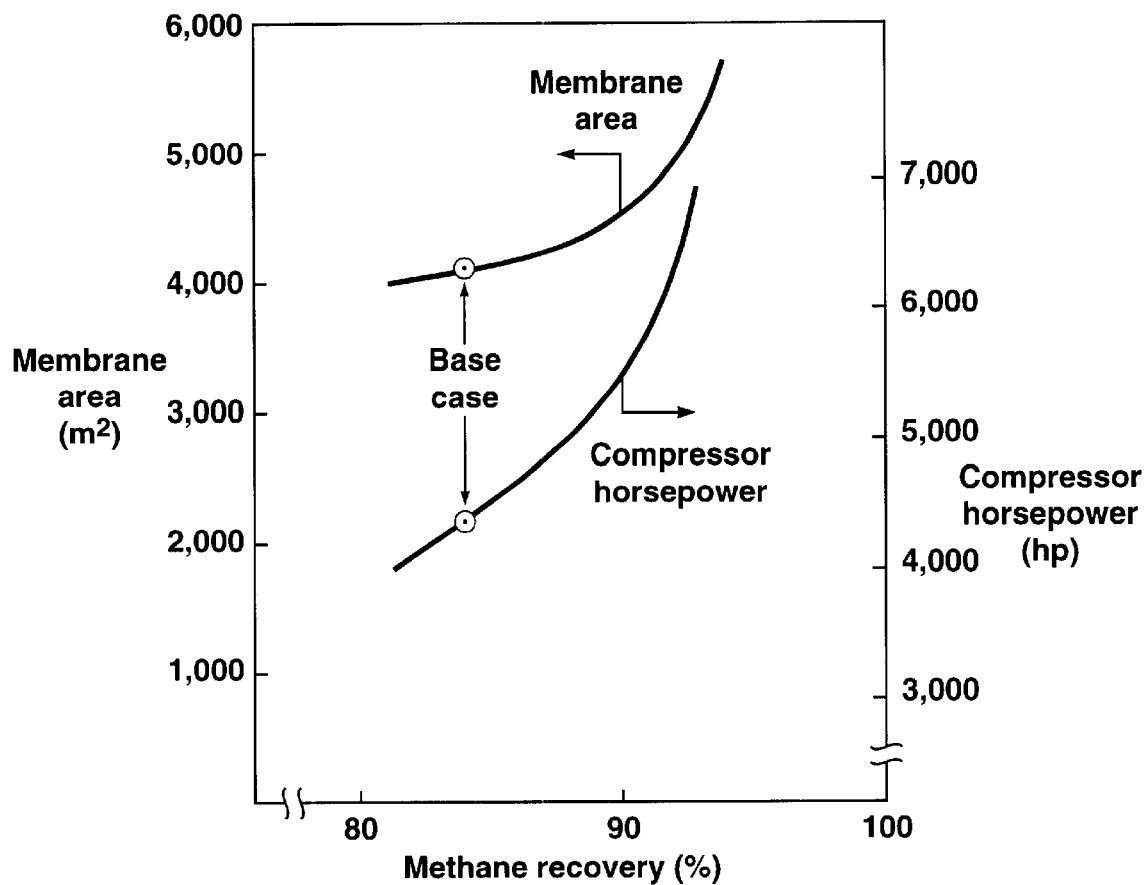
FIG. 5 is a graph of performance calculations for the embodiment of FIG. 4.

This same information is presented graphically in FIG. 5, which shows the relationship between membrane area, compressor horsepower requirement, and methane recovery. By comparing Example 7 with Examples 12 and 13, the savings of horsepower and membrane area that can be achieved by the use of a third membrane stage can be seen. However, the third stage requires a second compressor to be used.

Set 4

Effect of Membrane Selectivity on Methane Recovery in Basic Embodiment

A series of calculations to demonstrate the effect of membrane nitrogen/methane selectivity on methane recovery was performed. The process configuration was assumed to be a basic one-stage, two-step arrangement as in FIG. 1. For simplicity and since the selectivity of the membrane for other components over methane is less critical to the success of the process, other stream components were omitted. The calculations were performed to obtain a product gas containing 4% nitrogen and 96% methane in each case.

The calculations were also performed to produce a second permeate stream, 108, with the same composition, that is, 20% nitrogen, as the raw gas stream, 101, to eliminate loss of productivity caused by mixing streams of unlike composition.

Example 15

A computer calculation was performed assuming a membrane nitrogen/methane selectivity of 5 in both membrane steps. The process was assumed to be carried out as shown in FIG. 1, but, for simplicity of the calculation, without using heat integration. The flow rate of the raw gas was assumed to be 10 MMscfd, and the composition of the raw gas was assumed to be 80% methane and 20% nitrogen. The raw gas was assumed to be at 200 psia and 20° C., and to be compressed to 800 psia in compressor 110. The permeate sides of both membrane steps were assumed to be maintained at 200 psia. The stream numbers correspond to FIG. 1. The results of the calculations are summarized in Table 16.

TABLE 16

| Stream | 101 | 102 | 105 | 106 | 107 | 108 | 109 |
|---|---|---|---|---|---|---|---|
| Mass flow (lb/h) | 21,400 | 36,900 | 36,900 | 11,736 | 25,176 | 15,505 | 9,671 |
| Flow (MMscfd) | 10.0 | 17.2 | 17.2 | 5.0 | 12.3 | 7.2 | 5.0 |
| Temp. (° C.) | 20 | 18 | 25 | 23 | 21 | 15 | 9 |
| Pressure (psia) | 200 | 200 | 800 | 200 | 800 | 200 | 800 |
| Component (mol %): | | | | | | | |
| Nitrogen | 20.0 | 20.0 | 20.0 | 36.3 | 13.4 | 20.0 | 4.0 |
| Methane | 80.0 | 80.0 | 80.0 | 63.7 | 86.6 | 80.0 | 96.0 |

Membrane area = 2,537 m² (930 + 1,607)
Theoretical horsepower = 1,327 hp

The process yielded 5.0 MMscfd of gas as second residue product stream 109, containing 4% nitrogen, which meets pipeline specification. The methane recovery is 61%.

Example 16

The computer calculation of Example 15 was repeated assuming a membrane nitrogen/methane selectivity of 4 in both membrane units. All other process parameters were assumed to be as in Example 15. The stream numbers correspond to FIG. 1. The results of the calculations are summarized in Table 17.

TABLE 17

| Stream | 101 | 102 | 105 | 106 | 107 | 108 | 109 |
|---|---|---|---|---|---|---|---|
| Mass flow (lb/h) | 21,400 | 44,190 | 44,190 | 12,084 | 32,122 | 22,793 | 9,329 |
| Flow (MMscfd) | 10.0 | 20.6 | 20.6 | 5.1 | 15.5 | 10.6 | 4.9 |
| Temp. (° C.) | 20 | 17 | 25 | 23 | 22 | 15 | 8 |
| Pressure (psia) | 200 | 200 | 800 | 200 | 800 | 200 | 800 |
| Component (mol %): | | | | | | | |
| Nitrogen | 20.0 | 20.2 | 20.2 | 35.2 | 15.2 | 20.4 | 4.0 |
| Methane | 80.0 | 79.8 | 79.8 | 64.8 | 84.8 | 79.6 | 96.0 |

Membrane area = 2,702 m² (800 + 1,902)
Theoretical horsepower = 1,584 hp

The process yielded 4.9 MMscfd of gas as second residue product stream 109, containing 4% nitrogen, which meets pipeline specification. The methane recovery is a little lower, at 58%.

Example 17

The computer calculation of Example 15 was repeated assuming a membrane nitrogen/methane selectivity of 3 in both membrane units. All other process parameters were assumed to be as in Example 15. The stream numbers correspond to FIG. 1. The results of the calculations are summarized in Table 18.

TABLE 18

| Stream | 101 | 102 | 105 | 106 | 107 | 108 | 109 |
|---|---|---|---|---|---|---|---|
| Mass flow (lb/h) | 21,400 | 56,904 | 56,904 | 13,135 | 43,743 | 35,507 | 8,236 |
| Flow (MMscfd) | 10.0 | 26.6 | 26.6 | 5.7 | 20.9 | 16.6 | 4.3 |
| Temp. (° C.) | 20 | 17 | 25 | 24 | 22 | 15 | 8 |
| Pressure (psia) | 200 | 200 | 800 | 200 | 800 | 200 | 800 |
| Component (mol %): | | | | | | | |
| Nitrogen | 20.0 | 19.8 | 19.8 | 32.1 | 16.5 | 19.7 | 4.0 |
| Methane | 80.0 | 80.2 | 80.2 | 67.9 | 83.5 | 80.3 | 96.0 |

Membrane area = 3,000 m² (710 + 2,290)
Theoretical horsepower = 2,042 hp

The process yielded 4.3 MMscfd of gas as second residue product stream 109, containing 4% nitrogen, which meets pipeline specification. The methane recovery is 52%.

TABLE 19

| Stream | 101 | 102 | 105 | 106 | 107 | 108 | 109 |
|---|---|---|---|---|---|---|---|
| Mass flow (lb/h) | 21,400 | 80,725 | 80,725 | 13,617 | 67,059 | 59,328 | 7,731 |
| Flow (MMscfd) | 10.0 | 37.7 | 37.7 | 5.9 | 31.7 | 27.7 | 4.0 |
| Temp. (° C.) | 20 | 17 | 25 | 24 | 23 | 16 | 9 |
| Pressure (psia) | 200 | 200 | 800 | 200 | 800 | 200 | 800 |
| Component (mol %): | | | | | | | |
| Nitrogen | 20.0 | 20.0 | 20.0 | 30.8 | 18.0 | 20.1 | 4.0 |
| Methane | 80.0 | 80.0 | 80.0 | 69.2 | 82.0 | 79.9 | 96.0 |

Membrane area = 3,860 m² (640 + 3,200)
Theoretical horsepower = 2,893 hp

Example 18

The computer calculation of Example 15 was repeated assuming a membrane nitrogen/methane selectivity of 2.5 in both membrane units. All other process parameters were assumed to be as in Example 15. The stream numbers correspond to FIG. 1. The results of the calculations are summarized in Table 19.

The process yielded 4.0 MMscfd of gas as second residue product stream 109, containing 4% nitrogen, which meets pipeline specification. The methane recovery is 48%.

Example 19

The computer calculation of Example 15 was repeated assuming a membrane nitrogen/methane selectivity of 2 in both membrane units. All other process parameters were assumed to be as in Example 15. The stream numbers correspond to FIG. 1. The results of the calculations are summarized in Table 20.

TABLE 20

| Stream | 101 | 102 | 105 | 106 | 107 | 108 | 109 |
|---|---|---|---|---|---|---|---|
| Mass flow (lb/h) | 21,400 | 155,187 | 155,187 | 14,737 | 140,551 | 133,790 | 6,761 |
| Flow (MMscfd) | 10.0 | 72.5 | 72.5 | 6.5 | 66.0 | 62.5 | 3.5 |
| Temp. (° C.) | 20 | 15 | 25 | 24 | 24 | 14 | 4 |
| Pressure (psia) | 200 | 200 | 800 | 200 | 800 | 200 | 800 |
| Component (mol %): | | | | | | | |
| Nitrogen | 20.0 | 20.1 | 20.1 | 28.7 | 19.3 | 20.2 | 4.0 |
| Methane | 80.0 | 79.9 | 79.9 | 71.3 | 80.7 | 79.8 | 96.0 |

Membrane area = 6,523 m² (590 + 5,933)
Theoretical horsepower = 5,517 hp

The process yielded 3.5 MMscfd of gas as second residue product stream 109, containing 4% nitrogen, which meets pipeline specification. The methane recovery is 42%.

Example 20

The results of the calculations of Examples 15–19 are summarized in Table 21.

TABLE 21

| Parameter ▶ | $N_2/CH_4$ | Methane Recovery | Methane Recovery | Membrane Area (m²) | | Theoretical Compressor |
|---|---|---|---|---|---|---|
| Example # ▼ | Selectivity | (%) | (MMscfd) | Second-Step | Total | Horsepower |
| Example 15 | 5 | 61 | 5.0 | 1,607 | 2,537 | 1,327 |
| Example 16 | 4 | 58 | 4.9 | 1,902 | 2,702 | 1,584 |
| Example 17 | 3 | 52 | 4.3 | 2,290 | 3,000 | 2,042 |
| Example 18 | 2.5 | 48 | 4.0 | 3,220 | 3,860 | 2,893 |
| Example 19 | 2 | 42 | 3.5 | 5,933 | 6,523 | 5,517 |

Figure 6:
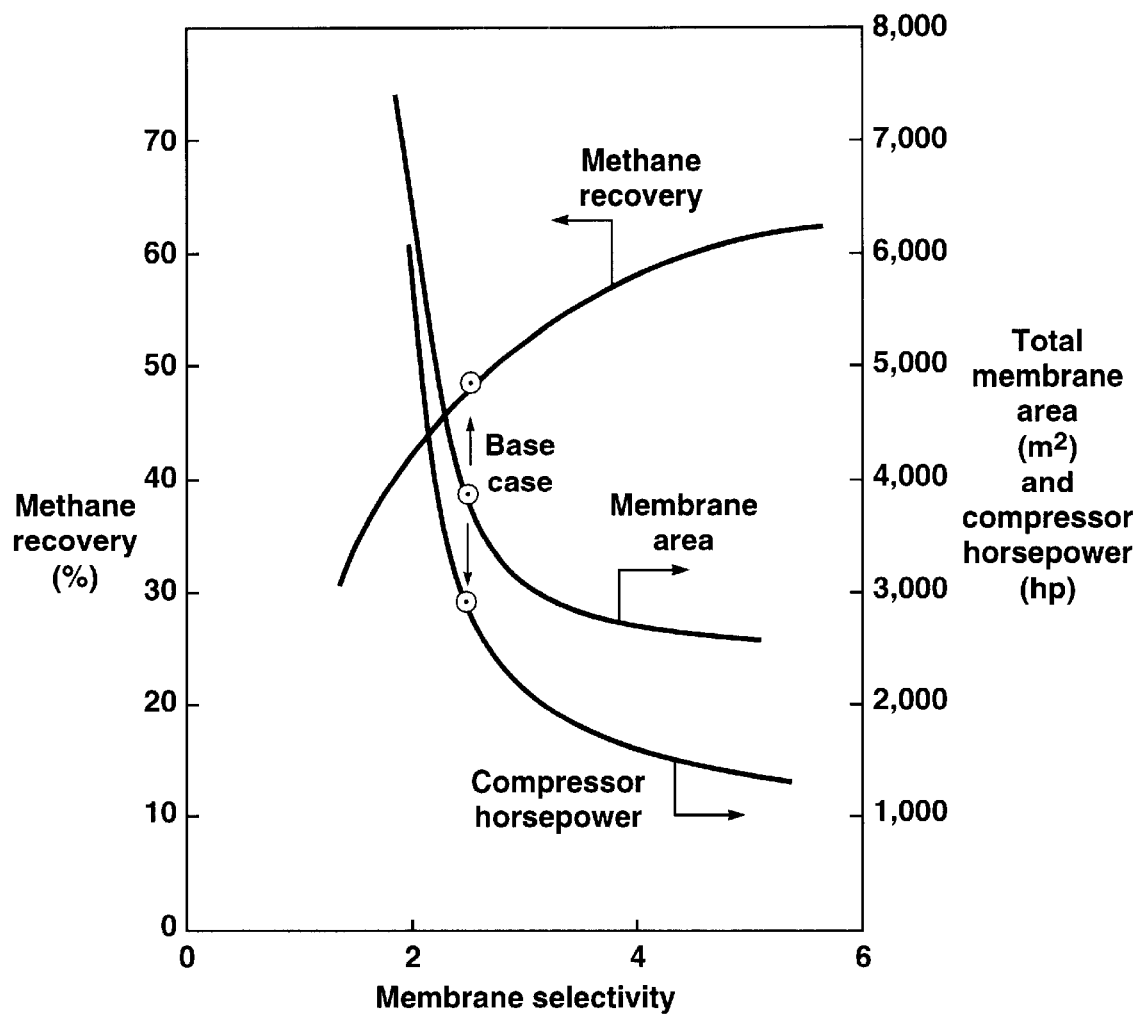
FIG. 6 is a graph of performance calculations as a function of selectivity for the embodiment of FIG. 1.

This same information is presented graphically in FIG. 6. The table and figure show the relationship between selectivity, methane recovery, membrane area required, and compression energy needs.

As can be seen, even with a relatively poor membrane selectivity of only 2 for nitrogen over methane, the process can produce a pipeline-quality product. However, as the selectivity improves, the methane recovery improves substantially, going from 42% to 60%. Likewise, as selectivity improves, the membrane area needed to perform the separation drops, as does the compression energy required. These effects are particularly pronounced as the selectivity increases from 2 to 2.5 to 3, showing the benefit of even very modest improvement in selectivity through cooling or judicious choice of membrane materials.

Set 5

Effect of Membrane Selectivity on Methane Recovery in Two-Step/Two-Stage Design

A set of calculations similar to that of Set 4 was performed. In this case, the process configuration of FIG. 2 was used. The calculations were again performed to obtain a product gas containing 96% methane and 4% nitrogen. Also, the calculations were set to provide that recirculated streams 206 and 209 contain 20% nitrogen to match the composition of raw gas stream 201.

Example 21

A computer calculation was performed assuming a membrane nitrogen/methane selectivity of 5 in all three membrane units. The process was assumed to be carried out as shown in FIG. 2. The flow rate of the raw gas was assumed to be 10 MMscfd, and the composition of the raw gas was assumed to be 80% methane and 20% nitrogen. The raw gas was assumed to be at 200 psia and 20° C., and to be compressed to 800 psia in compressor 210. The permeate sides of both membrane steps in the first stage were assumed to be maintained at 200 psia, and membrane unit 213 at 20 psia. The stream numbers correspond to FIG. 2. The results of the calculations are summarized in Table 22.

TABLE 22

| Stream | 201 | 202 | 203 | 204 | 205 | 206 | 207 | 208 | 209 |
|---|---|---|---|---|---|---|---|---|---|
| Mass Flow (lb/h) | 21,400 | 52,859 | 52,859 | 16,993 | 35,880 | 21,993 | 13,886 | 7,524 | 9,469 |
| Flow (MMscfd) | 10.0 | 24.7 | 24.7 | 7.2 | 17.5 | 10.3 | 7.2 | 2.8 | 4.4 |
| Temp. (° C.) | 20 | 18 | 25 | 23 | 21 | 15 | 9 | 22 | 21 |
| Pressure (psia) | 200 | 200 | 800 | 200 | 800 | 200 | 800 | 20 | 200 |
| Component (mol %): | | | | | | | | | |
| Nitrogen | 20.0 | 20.0 | 20.0 | 36.1 | 13.3 | 19.9 | 4.0 | 62.0 | 20.0 |
| Methane | 80.0 | 80.0 | 80.0 | 63.9 | 86.7 | 80.1 | 96.0 | 38.0 | 80.0 |

Membrane area = 4,861 m$^2$ (1,350 + 2,284 + 1,227)
Theoretical horsepower = 1,903 hp The process yielded 7.2 MMscfd of product gas, containing only 4% nitrogen, which meets pipeline specification. The methane recovery is 87%.

Example 22

The computer calculation of Example 21 was repeated assuming a membrane nitrogen/methane selectivity of 4 in all three membrane units. All other process parameters were assumed to be as in Example 21. The stream numbers correspond to FIG. 2. The results of the calculations are summarized in Table 23.

TABLE 23

| Stream | 201 | 202 | 203 | 204 | 205 | 206 | 207 | 208 | 209 |
|---|---|---|---|---|---|---|---|---|---|
| Mass Flow (lb/h) | 21,400 | 62,556 | 62,556 | 17,717 | 44,866 | 31,534 | 13,332 | 8,082 | 9,625 |
| Flow (MMscfd) | 10.0 | 29.2 | 29.2 | 7.6 | 21.7 | 14.7 | 7.0 | 3.1 | 4.5 |
| Temp. (° C.) | 20 | 17 | 25 | 23 | 21 | 14 | 8 | 22 | 21 |
| Pressure (psia) | 200 | 200 | 800 | 200 | 800 | 200 | 800 | 20 | 200 |
| Component (mol %): | | | | | | | | | |
| Nitrogen | 20.0 | 20.0 | 20.0 | 34.7 | 14.9 | 20.0 | 4.0 | 56.4 | 20.0 |
| Methane | 80.0 | 80.0 | 80.0 | 65.3 | 85.1 | 80.0 | 96.0 | 43.6 | 80.0 |

Membrane area = 5,065 m$^2$ (1,180 + 2,645 + 1,240)
Theoretical horsepower = 2,246 hp The process yielded 7.0 MMscfd of product gas, containing 4% nitrogen. The methane recovery is 83%.

Example 23

The computer calculation of Example 21 was repeated assuming a membrane nitrogen/methane selectivity of 2.5 in all three membrane units. All other process parameters were assumed to be as in Example 21. The stream numbers correspond to FIG. 2. The results of the calculations are summarized in Table 24.

TABLE 24

| Stream | 201 | 202 | 203 | 204 | 205 | 206 | 207 | 208 | 209 |
|---|---|---|---|---|---|---|---|---|---|
| Mass Flow (lb/h) | 21,400 | 120,349 | 120,349 | 20,230 | 100,180 | 88,678 | 11,502 | 9,956 | 10,274 |
| Flow (MMscfd) | 10.0 | 56.2 | 56.2 | 8.8 | 47.4 | 41.4 | 6.0 | 4.0 | 4.8 |
| Temp. (° C.) | 20 | 17 | 25 | 24 | 23 | 16 | 9 | 23 | 21 |
| Pressure (psia) | 200 | 200 | 800 | 200 | 800 | 200 | 800 | 20 | 200 |
| Component (mol %): | | | | | | | | | |
| Nitrogen | 20.0 | 20.1 | 20.1 | 30.9 | 18.1 | 20.1 | 4.0 | 43.9 | 20.0 |
| Methane | 80.0 | 79.9 | 79.9 | 69.1 | 81.9 | 79.9 | 96.0 | 56.1 | 80.0 |

Membrane area = 7.066 m$^2$ (950 + 4,809 + 1,307)
Theoretical horsepower = 4,314 hp The process yielded 6.0 MMscfd of product gas, containing 4% nitrogen. The methane recovery is 72%.

Example 24

The results of the calculations of Examples 21–23 are summarized in Table 25.

TABLE 25

| Parameter ▶<br>Example # ▼ | $N_2/CH_4$<br>Selectivity | Methane<br>Recovery<br>(%) | Methane<br>Recovery<br>(MMscfd) | Membrane Area ($m^2$) | | Theoretical<br>Compressor<br>Horsepower |
|---|---|---|---|---|---|---|
| | | | | Second-Step | Total | |
| Example 21 | 5 | 87 | 7.2 | 1,227 | 4,861 | 1,903 |
| Example 22 | 4 | 83 | 7.0 | 1,240 | 5,065 | 2,246 |
| Example 23 | 2.5 | 72 | 6.0 | 1,307 | 7,066 | 4,314 |

Figure 7:
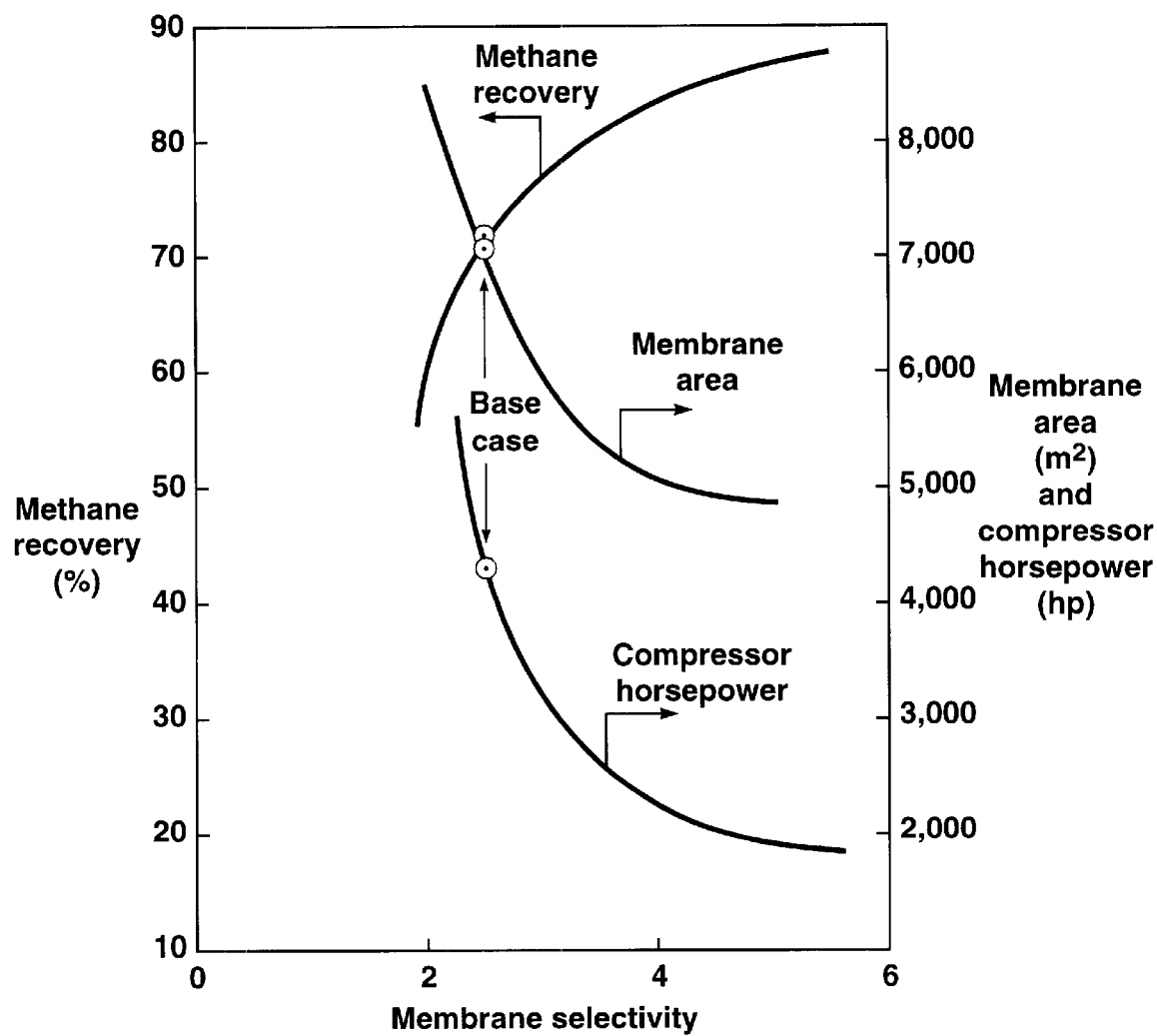
FIG. 7 is a graph of performance calculations as a function of selectivity for the embodiment of FIG. 2.

This same information is presented graphically in FIG. 7. The tables and figure show the relationship between selectivity, methane recovery, membrane area required, and compression energy needs.

As can be seen in FIG. 7, the trends are similar to those seen in the Set 4 calculations. That is, methane recovery improves substantially, from about 60% to 87%, as the selectivity improves from 2 to 5, and there is a large drop in membrane area and compressor horsepower requirements over the same selectivity range. Again, it is seen that the sharpest drop in these requirements occurs as selectivity is raised from 2 to 2.5 to 3, emphasizing the benefit of making every effort to reach a selectivity of slightly greater than 2.

When FIG. 7 is compared with FIG. 6, the improvements brought about by the use of the second membrane stage, 213, can be seen. For example, if a membrane providing a selectivity of 3 is available, the one-stage, two-step arrangement of FIG. 1 can achieve about 50% methane recovery. In contrast, the two-step, two-stage arrangement of FIG. 2 achieved about 75% methane recovery under the same conditions. The two-stage configuration requires significantly more membrane area (typically, roughly double) and compressor horsepower (typically, about 50% more) for the same separation. However, the process design remains simple, with only one moving part. The two-stage configuration is, therefore, attractive where the increased capital and operating costs of compression are balanced or outweighed by the greater gas recovery.

Set 6

Effect of Feed Nitrogen Concentration on Methane Recovery

A series of calculations according to the two-step/two-stage process design of the invention, as shown in FIG. 2, was performed to demonstrate the effect of feed nitrogen concentration on the methane recovery that can be achieved. The calculations assumed a membrane nitrogen/methane selectivity of 2.5 and a carbon dioxide-methane selectivity of 20 in all the membrane units. The calculations were performed to achieve a product gas of about 4% total inerts content to meet pipeline specification.

Example 25

A computer calculation was performed according to the process design shown in FIG. 2. The flow rate of the raw gas was assumed to be 10 MMscfd, and the composition of the raw gas was assumed to be 80% methane, 5% nitrogen, and 15% carbon dioxide. The raw gas was assumed to be at 200 psia and 50° C., and to be compressed to 1,200 psia in compressor 210. The permeate sides of both membrane steps in the first stage were assumed to be maintained at 200 psia, and membrane unit 213 at 20 psia. The stream numbers correspond to FIG. 2. The results of the calculations are summarized in Table 26.

TABLE 26

| Stream | 201 | 202 | 203 | 204 | 205 | 206 | 207 | 208 | 209 |
|---|---|---|---|---|---|---|---|---|---|
| Flow (MMscfd) | 10.0 | 14.2 | 14.2 | 6.2 | 8.0 | 1.2 | 6.8 | 3.2 | 3.0 |
| Temp. (° C.) | 50 | 38 | 25 | 16 | 7 | 4 | 2 | 13 | 10 |
| Pressure (psia) | 200 | 200 | 1,200 | 200 | 1,200 | 200 | 1,200 | 20 | 200 |
| Component (mol %): | | | | | | | | | |
| Nitrogen | 5.0 | 5.3 | 5.3 | 7.4 | 3.7 | 6.5 | 3.2 | 8.8 | 5.8 |
| Methane | 80.0 | 83.5 | 83.5 | 68.9 | 94.8 | 88.2 | 96.0 | 46.0 | 93.2 |
| Carbon Dioxide | 15.0 | 11.2 | 11.2 | 23.8 | 1.5 | 5.3 | 0.8 | 45.2 | 1.0 |

Membrane area = 1,175 $m^2$ (359 + 88 + 728)
Theoretical horsepower = 1,549 hp

The process yielded 6.8 MMscfd of product gas, with 82% methane recovery.

Example 26

The computer calculation of Example 25 was repeated, this time with a raw gas stream more heavily contaminated with nitrogen. The composition of the raw gas was assumed to be 75% methane, 10% nitrogen, and 15% carbon dioxide. All other process parameters were assumed to be as in Example 25. The stream numbers correspond to FIG. 2. The results of the calculations are summarized in Table 27.

TABLE 27

| Stream | 201 | 202 | 203 | 204 | 205 | 206 | 207 | 208 | 209 |
|---|---|---|---|---|---|---|---|---|---|
| Flow (MMscfd) | 10.0 | 20.2 | 20.2 | 9.0 | 11.1 | 5.3 | 5.8 | 4.2 | 4.8 |
| Temp. (° C.) | 50 | 29 | 25 | 18 | 11 | 2 | −7 | 16 | 13 |
| Pressure (psia) | 200 | 200 | 1,200 | 200 | 1,200 | 200 | 1,200 | 20 | 200 |
| Component (mol %): | | | | | | | | | |
| Nitrogen | 10.0 | 10.6 | 10.6 | 14.8 | 7.2 | 10.6 | 4.0 | 18.3 | 11.7 |
| Methane | 75.0 | 81.2 | 81.2 | 68.1 | 91.8 | 87.4 | 95.9 | 46.0 | 87.3 |
| Carbon Dioxide | 15.0 | 8.2 | 8.2 | 17.1 | 1.0 | 2.0 | 0.1 | 35.7 | 1.0 |

Membrane area = 1,937 m² (536 + 386 + 1,015)
Theoretical horsepower = 2,144 hp

The process yielded 5.8 MMscfd of product gas, with 75% methane recovery.

Example 27

The computer calculation of Example 25 was repeated, this time with a raw gas stream more heavily contaminated with nitrogen. The composition of the raw gas was assumed to be 70% methane, 15% nitrogen, and 15% carbon dioxide. All other process parameters were assumed to be as in Example 25. The stream numbers correspond to FIG. 2. The results of the calculations are summarized in Table 28.

TABLE 28

| Stream | 201 | 202 | 203 | 204 | 205 | 206 | 207 | 208 | 209 |
|---|---|---|---|---|---|---|---|---|---|
| Flow (MMscfd) | 10.0 | 26.9 | 26.9 | 11.0 | 15.9 | 10.8 | 5.1 | 4.9 | 6.2 |
| Temp. (° C.) | 50 | 21 | 25 | 18 | 11 | −1 | −14 | 16 | 14 |
| Pressure (psia) | 200 | 200 | 1,200 | 200 | 1,200 | 200 | 1,200 | 20 | 200 |
| Component (mol %): | | | | | | | | | |
| Nitrogen | 15.0 | 15.2 | 15.2 | 21.5 | 10.9 | 14.2 | 4.0 | 26.6 | 17.4 |
| Methane | 70.0 | 78.4 | 78.4 | 64.4 | 88.1 | 84.3 | 96.0 | 42.6 | 81.6 |
| Carbon Dioxide | 15.0 | 6.4 | 6.4 | 14.2 | 1.0 | 1.5 | 0.01 | 30.8 | 1.0 |

Membrane area = 2,584 m² (643 + 768 + 1,173)
Theoretical horsepower = 2,805 hp

The process yielded 5.1 MMscfd of product gas, with 70% methane recovery.

Example 28

The computer calculation of Example 25 was repeated, this time with a raw gas stream still more heavily contaminated with nitrogen. The composition of the raw gas was assumed to be 60% methane, 25% nitrogen, and 15% carbon dioxide. All other process parameters were assumed to be as in Example 25. The stream numbers correspond to FIG. 2. The results of the calculations are summarized in Table 29.

TABLE 29

| Stream | 201 | 202 | 203 | 204 | 205 | 206 | 207 | 208 | 209 |
|---|---|---|---|---|---|---|---|---|---|
| Flow (MMscfd) | 10.0 | 38.3 | 38.3 | 13.9 | 24.4 | 20.3 | 4.1 | 5.9 | 8.1 |
| Temp. (° C.) | 50 | 18 | 25 | 20 | 14 | 2 | −11 | 18 | 17 |
| Pressure (psia) | 200 | 200 | 1,200 | 200 | 1,200 | 200 | 1,200 | 20 | 200 |
| Component (mol %): | | | | | | | | | |
| Nitrogen | 25.0 | 23.7 | 23.7 | 33.0 | 18.4 | 2.14 | 4.0 | 39.6 | 28.1 |
| Methane | 60.0 | 71.5 | 71.5 | 55.7 | 80.6 | 77.4 | 96.0 | 34.9 | 70.9 |
| Carbon Dioxide | 15.0 | 4.8 | 4.8 | 11.3 | 1.0 | 1.2 | 10 ppm | 25.5 | 1.0 |

Membrane area = 3,498 m² (767 + 1,384 + 1,347)
Theoretical horsepower = 3,976 hp The process yielded 4.1 MMscfd of product gas, with 66% methane recovery.

Example 29

The results of the calculations of Examples 25–28 are summarized in Table 30.

TABLE 30

| Parameter ▶<br>Example # ▼ | Feed Nitrogen<br>Concentration<br>(%) | Methane<br>Recovery<br>(%) | Methane<br>Recovery<br>(MMscfd) | Membrane Area<br>($m^2$) | Theoretical<br>Compressor<br>Horsepower |
|---|---|---|---|---|---|
| Example 25 | 5 | 82 | 6.8 | 1,175 | 1,549 |
| Example 26 | 10 | 75 | 5.8 | 1,937 | 2,144 |
| Example 27 | 15 | 70 | 5.1 | 2,584 | 2,805 |
| Example 28 | 25 | 66 | 4.1 | 3,498 | 3,976 |

It can be seen that the process can both meet pipeline specification and provide reasonable methane recovery, even when handling streams with large quantities of contaminants, and with a nitrogen/methane selectivity of only 2.5.

Set 7

Effect of Feed Carbon Dioxide Concentration on Methane Recovery

A set of calculations similar to that of Set 6 was performed, this time to illustrate the effect of feed carbon dioxide concentration on the methane recovery that can be achieved. The two-step/two-stage process design of the invention, as shown in FIG. 2, was assumed to be used. The calculations assumed a membrane nitrogen/methane selectivity of 2.5 and a carbon dioxide/methane selectivity of 20 in all the membrane units. The calculations were again performed to achieve a product gas of about 4% total inerts content to meet pipeline specification.

Example 30

A computer calculation was performed according to the process design shown in FIG. 2. The flow rate of the raw gas was assumed to be 10 MMscfd, and the composition of the raw gas was assumed to be 75% methane, 10% nitrogen, and 15% carbon dioxide. The raw gas was assumed to be at 200 psia and 50° C., and to be compressed to 1,200 psia in compressor 210. The permeate sides of both membrane steps in the first stage were assumed to be maintained at 200 psia, and membrane unit 213 at 20 psia. The stream numbers correspond to FIG. 2. The results of the calculations are summarized in Table 31.

TABLE 31

| Stream | 201 | 202 | 203 | 204 | 205 | 206 | 207 | 208 | 209 |
|---|---|---|---|---|---|---|---|---|---|
| Flow (MMscfd) | 10.0 | 23.8 | 23.8 | 7.7 | 16.0 | 9.9 | 6.2 | 3.8 | 3.9 |
| Temp. (° C.) | 50 | 25 | 25 | 19 | 14 | 4 | −6 | 17 | 14 |
| Pressure (psia) | 200 | 200 | 1,200 | 200 | 1,200 | 200 | 1,200 | 20 | 200 |
| Component (mol %): | | | | | | | | | |
| Nitrogen | 10.0 | 11.6 | 11.6 | 16.6 | 9.2 | 12.5 | 4.0 | 19.7 | 13.5 |
| Methane | 75.0 | 80.6 | 80.6 | 63.5 | 88.8 | 84.2 | 95.9 | 41.2 | 85.5 |
| Carbon Dioxide | 15.0 | 7.8 | 7.8 | 19.9 | 2.0 | 3.2 | 0.05 | 39.1 | 1.0 |

Membrane area = 1,993 $m^2$ (435 + 699 + 859)
Theoretical horsepower = 2,499 hp

The process yielded 6.2 MMscfd of product gas, with 79% methane recovery.

Example 31

The computer calculation of Example 30 was repeated, this time with a raw gas stream more heavily contaminated with carbon dioxide. The composition of the raw gas was assumed to be 70% methane, 10% nitrogen, and 20% carbon dioxide. All other process parameters were assumed to be as in Example 30. The stream numbers correspond to FIG. 2. The results of the calculations are summarized in Table 32.

TABLE 32

| Stream | 201 | 202 | 203 | 204 | 205 | 206 | 207 | 208 | 209 |
|---|---|---|---|---|---|---|---|---|---|
| Flow (MMscfd) | 10.0 | 21.6 | 21.6 | 8.4 | 13.3 | 7.7 | 5.5 | 4.5 | 3.9 |
| Temp. (° C.) | 50 | 26 | 25 | 18 | 11 | 1 | −8 | 15 | 12 |
| Pressure (psia) | 200 | 200 | 1,200 | 200 | 1,200 | 200 | 1,200 | 20 | 200 |
| Component (mol %): | | | | | | | | | |
| Nitrogen | 10.0 | 11.2 | 11.2 | 15.3 | 8.6 | 11.9 | 4.0 | 17.4 | 12.8 |
| Methane | 70.0 | 78.2 | 78.2 | 60.4 | 89.4 | 84.7 | 95.9 | 37.9 | 86.2 |
| Carbon Dioxide | 20.0 | 10.6 | 10.6 | 24.3 | 2.0 | 3.4 | 0.07 | 44.6 | 1.0 |

Membrane area = 1,924 m² (448 + 548 + 928)
Theoretical horsepower = 2,276 hp

The process yielded 5.5 MMscfd of product gas, with 76% methane recovery.

Example 32

The computer calculation of Example 30 was repeated, this time with a raw gas stream more heavily contaminated with carbon dioxide. The composition of the raw gas was assumed to be 60% methane, 10% nitrogen, and 30% carbon dioxide. All other process parameters were assumed to be as in Example 30. The stream numbers correspond to FIG. 2. The results of the calculations are summarized in Table 33.

TABLE 33

| Stream | 201 | 202 | 203 | 204 | 205 | 206 | 207 | 208 | 209 |
|---|---|---|---|---|---|---|---|---|---|
| Flow (MMscfd) | 10.0 | 19.5 | 19.5 | 9.3 | 10.2 | 5.8 | 4.4 | 5.6 | 3.6 |
| Temp. (° C.) | 50 | 26 | 25 | 15 | 5 | −4 | −14 | 11 | 7 |
| Pressure (psia) | 200 | 200 | 1,200 | 200 | 1,200 | 200 | 1,200 | 20 | 200 |
| Component (mol %): | | | | | | | | | |
| Nitrogen | 10.0 | 11.0 | 11.0 | 13.9 | 8.4 | 11.7 | 4.0 | 14.8 | 12.7 |
| Methane | 60.0 | 72.4 | 72.4 | 53.3 | 89.6 | 84.9 | 95.9 | 31.5 | 86.3 |
| Carbon Dioxide | 30.0 | 16.6 | 16.6 | 32.8 | 2.0 | 3.4 | 0.08 | 53.7 | 1.0 |

Membrane area = 1,841 m² (444 + 411 + 986)
Theoretical horsepower = 2,045 hp

The process yielded 4.4 MMscfd of product gas, with 71% methane recovery.

Example 33

The computer calculation of Example 30 was repeated, this time with a raw gas stream still more heavily contaminated with carbon dioxide. The composition of the raw gas was assumed to be 50% methane, 10% nitrogen, and 40% carbon dioxide. All other process parameters were assumed to be as in Example 30. The stream numbers correspond to FIG. 2. The results of the calculations are summarized in Table 34.

TABLE 34

| Stream | 201 | 202 | 203 | 204 | 205 | 206 | 207 | 208 | 209 |
|---|---|---|---|---|---|---|---|---|---|
| Flow (MMscfd) | 10.0 | 18.3 | 18.3 | 9.9 | 8.3 | 4.9 | 3.4 | 6.6 | 3.4 |
| Temp. (° C.) | 50 | 26 | 25 | 13 | 0 | −10 | −19 | 8 | 4 |
| Pressure (psia) | 200 | 200 | 1,200 | 200 | 1,200 | 200 | 1,200 | 20 | 200 |
| Component (mol %): | | | | | | | | | |
| Nitrogen | 10.0 | 11.2 | 11.2 | 13.2 | 8.7 | 12.0 | 4.0 | 13.2 | 13.3 |
| Methane | 50.0 | 65.9 | 65.9 | 46.2 | 89.3 | 84.6 | 95.9 | 25.9 | 85.7 |
| Carbon Dioxide | 40.0 | 23.0 | 23.0 | 40.6 | 2.0 | 3.4 | 0.06 | 61.0 | 1.0 |

Membrane area = 1,756 m$^2$ (421 + 348 + 987)
Theoretical horsepower = 1,914 hp

The process yielded 3.4 MMscfd of product gas, with 66% methane recovery.

Example 34

The results of the calculations of Examples 30–33 are summarized in Table 35.

TABLE 35

| Parameter ▶<br>Example # ▼ | Feed Carbon<br>Dioxide<br>Concentration (%) | Methane<br>Recovery<br>(%) | Methane<br>Recovery<br>(MMscfd) | Membrane Area<br>(m$^2$) | Theoretical<br>Compressor<br>Horsepower |
|---|---|---|---|---|---|
| Example 30 | 10 | 79 | 6.2 | 1,993 | 2,499 |
| Example 31 | 20 | 76 | 5.5 | 1,924 | 2,276 |
| Example 32 | 30 | 71 | 4.4 | 1,841 | 2,045 |
| Example 33 | 40 | 66 | 3.4 | 1,756 | 1,914 |

It can be seen that the process can yet again provide pipeline quality gas and a reasonable recovery of methane.

Set 8

Effect of Membrane Feed Pressure on Membrane Performance

A series of calculations was performed to illustrate the effect of membrane feed pressure on the process performance. The calculations were performed using the process configuration of FIG. 2, to obtain a product gas containing 4% nitrogen. The calculations were carried out using a nitrogen/methane selectivity of 2.5 and a carbon dioxide/methane selectivity of 20 for all membrane units.

Example 35

A computer calculation was performed according to the process design of FIG. 2, assuming a raw gas flow rate of 10 MMscfd, and a composition of 72.8% methane, 12% nitrogen, 15% carbon dioxide, and 0.2% water vapor. The raw gas was assumed to be at 200 psia and 50° C., and to be compressed to 800 psia in compressor 210. The permeate sides of both membrane steps were assumed to be maintained at 200 psia, providing a pressure ratio across these units of 4. The permeate side of membrane unit 213 was assumed to be maintained at 20 psia, providing a pressure ratio across this unit of 10. The stream numbers correspond to FIG. 2. The results of the calculations are summarized in Table 36.

TABLE 36

| Stream | 201 | 202 | 203 | 204 | 205 | 206 | 207 | 208 | 209 |
|---|---|---|---|---|---|---|---|---|---|
| Flow (MMscfd) | 10.0 | 33.1 | 33.1 | 14.6 | 18.6 | 12.9 | 5.7 | 4.3 | 10.3 |
| Temp. (° C.) | 50 | 25 | 25 | 21 | 17 | 10 | 3 | 20 | 18 |
| Pressure (psia) | 200 | 200 | 800 | 200 | 800 | 200 | 800 | 20 | 200 |
| Component (mol %): | | | | | | | | | |
| Nitrogen | 12.0 | 13.4 | 13.4 | 18.3 | 9.6 | 12.1 | 4.0 | 22.6 | 16.5 |
| Methane | 72.8 | 80.3 | 80.3 | 69.5 | 88.8 | 85.7 | 95.9 | 42.1 | 80.9 |
| Carbon Dioxide | 15.0 | 6.2 | 6.2 | 12.1 | 1.6 | 2.2 | 0.1 | 34.8 | 2.6 |
| Water | 0.2 | 0.1 | 0.1 | 0.2 | 0.02 | 0.03 | 9 ppm | 0.5 | 0.03 |

Membrane area = 4,030 m$^2$ (1,490 + 1,540 + 1,000)
Theoretical horsepower = 2,566 hp As can be seen, the process yielded 5.7 MMscfd of gas as second residue product stream 207. The gas contains 4% nitrogen, 0.1% carbon dioxide, and 9 ppm water vapor. The methane recovery is 75%.

Example 36

The calculation of Example 35 was repeated, with the raw gas assumed to be compressed to 1,000 psia in compressor 210, providing a pressure ratio across membrane units 211 and 212 of 5. All other process parameters are as in Example 35. The stream numbers correspond to FIG. 2. The results of the calculations are summarized in Table 37.

TABLE 37

| Stream | 201 | 202 | 203 | 204 | 205 | 206 | 207 | 208 | 209 |
|---|---|---|---|---|---|---|---|---|---|
| Flow (MMscfd) | 10.0 | 28.1 | 28.1 | 13.2 | 14.9 | 9.2 | 5.7 | 4.3 | 8.9 |
| Temp. (° C.) | 50 | 23 | 25 | 18 | 11 | 1 | 8 | 17 | 15 |
| Pressure (psia) | 200 | 200 | 1,000 | 200 | 1,000 | 200 | 1,000 | 20 | 200 |
| Component (mol %): | | | | | | | | | |
| Nitrogen | 12.0 | 13.4 | 13.4 | 18.4 | 8.9 | 12.0 | 4.0 | 22.6 | 16.3 |
| Methane | 72.8 | 80.0 | 80.0 | 68.6 | 90.1 | 86.4 | 96.0 | 42.1 | 81.4 |
| Carbon Dioxide | 15.0 | 6.6 | 6.6 | 12.9 | 1.0 | 1.6 | 0.05 | 34.9 | 2.2 |
| Water | 0.2 | 0.1 | 0.1 | 0.2 | 0.01 | 0.02 | 5 ppm | 0.5 | 0.02 |

Membrane area = 2,833 m$^2$ (1,000 + 833 + 1,000)
Theoretical horsepower = 2,582 hp The process again yielded 5.7 MMscfd of product gas, containing 4% nitrogen, 0.05% carbon dioxide, and 5 ppm water vapor. The methane recovery in this case is 78%.

Example 37

The calculation of Example 35 was repeated, with the raw gas assumed to be compressed to 1,200 psia in compressor 210, providing a pressure ratio across membrane units 211 and 212 of 6. All other process parameters are as in Example 35. The stream numbers correspond to FIG. 2. The results of the calculations are summarized in Table 38.

Figure 8:
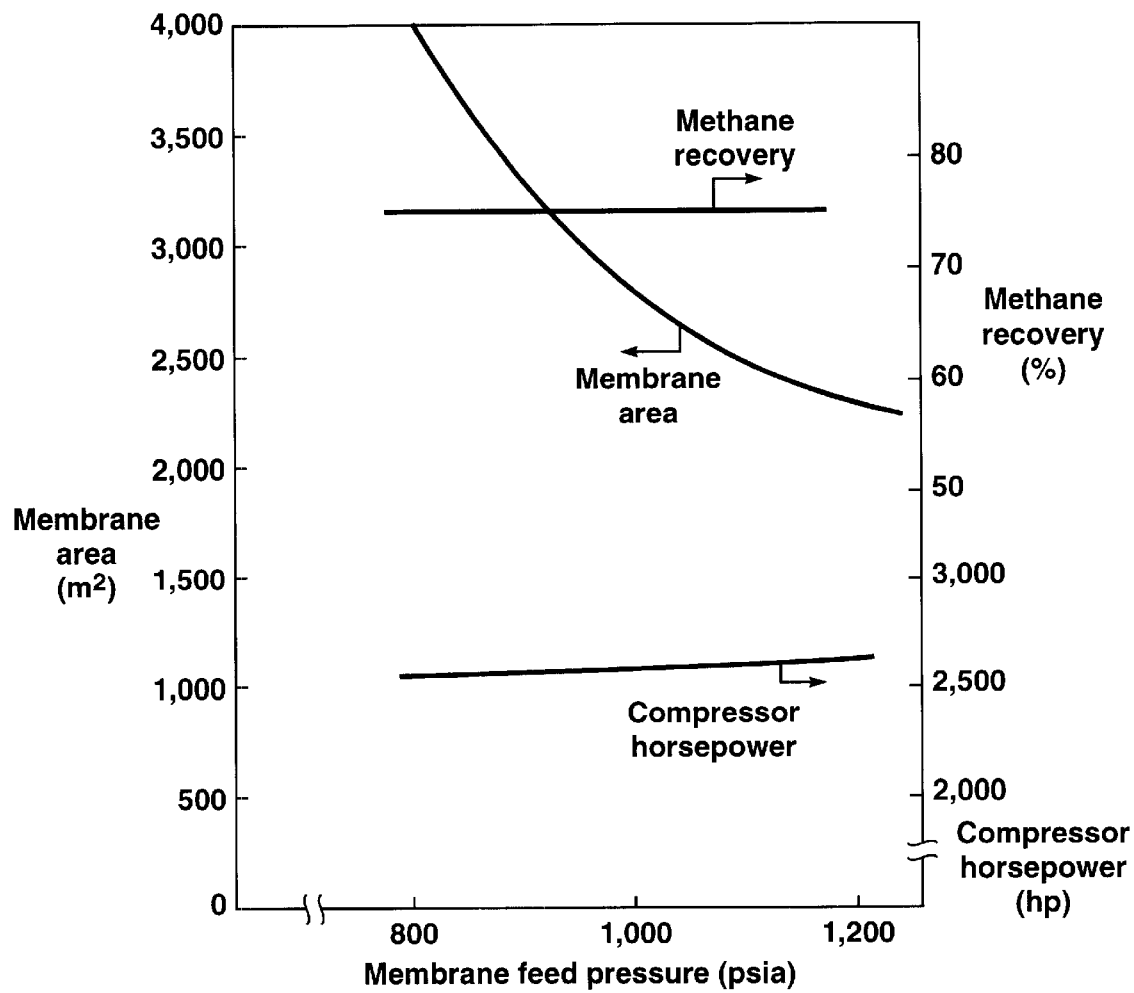
FIG. 8 is a graph of performance calculations as a function of pressure of the feed gas to the membrane for the embodiment of FIG. 2.

This same information is presented graphically in FIG. 8. As can be seen, the pressure ratio increase has essentially no impact on the methane recovery, because the separation is limited by the membrane selectivity of 2.5. On the other hand, the increased driving force provided by the increased pressure difference across the membranes increases the flux and reduces the amount of membrane area required to process the 10 MMscfd of gas. Although the gas is raised to higher pressure in Examples 36 and 37, the volume of stream 203 to be compressed is smaller in these examples, so the compressor horsepower requirement remains essentially unchanged.

TABLE 38

| Stream | 201 | 202 | 203 | 204 | 205 | 206 | 207 | 208 | 209 |
|---|---|---|---|---|---|---|---|---|---|
| Flow (MMscfd) | 10.0 | 25.5 | 25.5 | 12.3 | 13.2 | 7.5 | 5.7 | 4.3 | 8.0 |
| Temp. (° C.) | 50 | 23 | 25 | 16 | 7 | −3 | −12 | 14 | 12 |
| Pressure (psia) | 200 | 200 | 1,200 | 200 | 1,200 | 200 | 1,200 | 20 | 200 |
| Component (mol %): | | | | | | | | | |
| Nitrogen | 12.0 | 13.3 | 13.3 | 18.4 | 8.5 | 12.0 | 4.0 | 22.6 | 16.1 |
| Methane | 72.8 | 79.8 | 79.8 | 67.9 | 90.8 | 86.9 | 96.0 | 42.1 | 81.8 |
| Carbon Dioxide | 15.0 | 6.9 | 6.9 | 13.5 | 0.7 | 1.1 | 0.03 | 34.9 | 2.0 |
| Water | 0.2 | 0.1 | 0.1 | 0.2 | 0.01 | 0.01 | 3 ppm | 0.5 | 0.02 |

Membrane area = 2,283 m$^2$ (740 + 543 + 1,000)
Theoretical horsepower = 2,662 hp The process again yielded 5.7 MMscfd of product gas, containing 4% nitrogen, 0.03% carbon dioxide and 3 ppm water vapor, which meets pipeline specification. The methane recovery is 75%.

Example 38

The results of Examples 35–37 are summarized in Table 39.

Set 9

Effect of Membrane Feed Temperature on Methane Recovery

Two calculations were performed to show the benefits of operating with cooled feed streams to each membrane separation unit. The calculations were performed using the process configuration of FIG. 2 to obtain a product gas

TABLE 39

| Parameter ▶<br>Example # ▼ | Membrane<br>Feed Pressure<br>(psia) | Pressure Ratio<br>of First Step | Methane<br>Recovery<br>(%) | Methane<br>Recovery<br>(MMscfd) | Membrane<br>Area<br>(m$^2$) | Theoretical<br>Compressor<br>Horsepower |
|---|---|---|---|---|---|---|
| Example 35 | 800 | 4 | 75.2 | 5.7 | 4,030 | 2,566 |
| Example 36 | 1,000 | 5 | 78.2 | 5.7 | 2,833 | 2,582 |
| Example 37 | 1,200 | 6 | 75.1 | 5.7 | 2,283 | 2,662 | containing 4% nitrogen. The software calculates the residue and permeate stream temperatures, but does not adjust the membrane selectivity automatically. Therefore, for the first calculation, we simply assumed a nitrogen/methane selectivity of 2.5 for all membrane separation units, and for the second calculation, we assumed a nitrogen/methane selectivity of 3.0 for streams around 10° C. and of 3.5 for streams around −5° C. For all units in both calculations, the carbon dioxide/methane selectivity was assumed for simplicity to be 20, irrespective of temperature.

Example 39

A computer calculation was performed according to the process design of FIG. 2, and assuming a membrane nitrogen/methane selectivity of 2.5 in all three membrane units. The flow rate of the raw gas was assumed to be 10 MMscfd, and the gas was assumed to contain 72.8% methane, 12% nitrogen, 15% carbon dioxide, and 0.2% water vapor. The raw gas was assumed to be at 200 psia and 50° C., and to be compressed to 1,200 psia in compressor 210. The permeate sides of both membrane steps were assumed to be maintained at 200 psia, and membrane unit 213 at 20 psia. The stream numbers correspond to FIG. 2. The results of the calculations are summarized in Table 40.

As can be seen, the process yielded 5.7 MMscfd of gas as second residue product stream 207, containing 4% nitrogen, which meets pipeline specification. The methane recovery is 75%.

Example 40

The calculation of Example 39 was repeated. In this case, however, it was assumed that stream 207 was used to cool feed stream 203 to about 14° C. by heat exchange, resulting in a nitrogen/methane selectivity in step 211 of 3.0. The residue and permeate streams from this step were assumed to be fed to membrane separation step 212 and membrane separation stage 213 at their reduced temperatures, resulting in a nitrogen/methane selectivity of 3.5 in each of these separations.

All other process parameters were assumed to be as in Example 39. The stream numbers correspond to FIG. 2. The results of the calculations are summarized in Table 41.

TABLE 40

| Stream | 201 | 202 | 203 | 204 | 205 | 206 | 207 | 208 | 209 |
|---|---|---|---|---|---|---|---|---|---|
| Flow (MMscfd) | 10.0 | 25.6 | 25.6 | 12.4 | 13.1 | 7.4 | 5.7 | 4.3 | 8.1 |
| Temp. (° C.) | 50 | 16 | 14 | 5 | −5 | −14 | 20 | 3 | 0 |
| Pressure (psia) | 200 | 200 | 1,200 | 200 | 1,200 | 200 | 1,200 | 20 | 200 |
| Component (mol %): | | | | | | | | | |
| Nitrogen | 12.0 | 13.3 | 13.3 | 18.4 | 8.5 | 12.0 | 4.0 | 22.6 | 16.2 |
| Methane | 72.8 | 79.7 | 79.7 | 68.0 | 90.9 | 86.9 | 96.0 | 42.0 | 81.7 |
| Carbon Dioxide | 15.0 | 6.8 | 6.8 | 13.4 | 0.6 | 1.1 | 0.03 | 34.9 | 2.0 |
| Water | 0.2 | 0.1 | 0.1 | 0.2 | 0.01 | 0.01 | 2 ppm | 0.5 | 0.02 |

Membrane area = 2,290 m$^2$ (750 + 540 + 1,000)
Theoretical horsepower = 2,608 hp

TABLE 41

| Stream | 201 | 202 | 203 | 204 | 205 | 206 | 207 | 208 | 209 |
|---|---|---|---|---|---|---|---|---|---|
| Flow (MMscfd) | 10.0 | 21.0 | 21.0 | 12.2 | 8.9 | 2.6 | 6.3 | 3.7 | 8.4 |
| Temp. (° C.) | 50 | 23 | 14 | 4 | −5 | −10 | 20 | 2 | 0 |
| Pressure (psia) | 200 | 200 | 1,200 | 200 | 1,200 | 200 | 1,200 | 20 | 200 |
| Component (mol %): | | | | | | | | | |
| Nitrogen | 12.0 | 13.5 | 13.5 | 18.8 | 6.4 | 12.1 | 4.0 | 25.4 | 15.8 |
| Methane | 72.8 | 77.7 | 77.7 | 66.4 | 93.2 | 86.8 | 95.9 | 34.1 | 80.7 |
| Carbon Dioxide | 15.0 | 8.7 | 8.7 | 14.7 | 0.4 | 1.1 | 0.10 | 40.0 | 3.5 |
| Water | 0.2 | 0.1 | 0.1 | 0.2 | 35 ppm | 0.01 | 8 ppm | 0.5 | 0.03 |

Membrane area = 2,110 m$^2$ (850 + 260 + 1,000)
Theoretical horsepower = 2,197 hp Under these conditions, the process yielded 6.3 MMscfd of product gas meeting pipeline specification. The methane recovery is 83%. As can be seen, the improved membrane selectivity means that a much smaller membrane area (260 m$^2$ versus 540 m$^2$) is required in step 212 to bring the product gas to 4% nitrogen. This in turn leads to a much smaller recycle stream, 206, and cuts the horsepower requirements from 2,608 hp to 2,197 hp. The better selectivity also raised the methane recovery from 75% to 83%.

Set 10

Heavily Contaminated Stream

Example 41

A calculation was performed to show typical process performance with a gas stream heavily contaminated with both nitrogen and carbon dioxide. The flow rate of the raw gas was assumed to be 10 MMscfd, and the gas was assumed to contain 35% methane, 25% nitrogen, and 40% carbon dioxide. A membrane nitrogen/methane selectivity of 2.5 and a carbon dioxide/methane selectivity of 20 were assumed for all three membrane units. The raw gas was assumed to be at 200 psia and 50° C., and to be compressed to 1,200 psia in compressor 210. The permeate sides of both membrane steps were assumed to be maintained at 200 psia, and membrane unit 213 at 20 psia. The stream numbers correspond to FIG. 2. The results of the calculations are summarized in Table 42.

TABLE 42

| Stream | 201 | 202 | 203 | 204 | 205 | 206 | 207 | 208 | 209 |
|---|---|---|---|---|---|---|---|---|---|
| Flow (MMscfd) | 10.0 | 56.0 | 56.0 | 13.5 | 42.5 | 39.8 | 2.7 | 7.3 | 6.2 |
| Temp. (° C.) | 50 | 12 | 25 | 21 | 17 | 2 | −14 | 18 | 14 |
| Pressure (psia) | 200 | 200 | 1,200 | 200 | 1,200 | 200 | 1,200 | 20 | 200 |
| Component (mol %): | | | | | | | | | |
| Nitrogen | 25.0 | 34.4 | 34.4 | 38.9 | 33.0 | 35.0 | 4.0 | 32.8 | 46.1 |
| Methane | 35.0 | 54.3 | 54.3 | 30.1 | 62.0 | 59.7 | 96.0 | 12.6 | 50.9 |
| Carbon Dioxide | 40.0 | 11.3 | 11.3 | 31.0 | 5.0 | 5.3 | 1 ppm | 54.6 | 3.0 |

Membrane area = 3,754 m$^2$ (505 + 2,330 + 919)
Theroetical horsepower = 5,733 hp As can be seen, the process yielded 2.7 MMscfd of gas as second residue product stream 207, containing 4% nitrogen and 1 ppm carbon dioxide, which meets pipeline specification. The methane recovery is 74%.

Set 11

Pure Gas Permeation Experiments with Glassy Membrane Materials

Example 42

Pure Gas Permeation Experiments with Polyimide Membranes

Composite membranes were prepared by dip-coating asymmetric, microporous poly(vinylidene fluoride) [PVDF] support membranes in solutions of one of three polyimides: 6FDA-ODA, 6FDA-NDA, or 6FDA-mPDA. Samples of each finished composite membrane were cut into 12.6-cm$^2$ stamps and tested in a permeation test-cell apparatus with pure gases at 23° C. feed temperature, 65 psia feed pressure, and permeate pressure atmospheric. During each test, the feed, permeate, and residue compositions were analyzed by gas chromatography (GC). The gas fluxes of the membranes were measured, and the pressure-normalized fluxes and selectivities were calculated. Table 43 summarizes the fluxes and Table 44 summarizes the selectivities of the composite membranes, calculated as the ratio of the pure gas fluxes.

TABLE 43

| | Pure-Gas Pressure-Normalized Flux (GPU) | | |
|---|---|---|---|
| Gas | 6FDA-ODA | 6FDA-NDA | 6FDA-mPDA |
| Nitrogen | 3.15 | 22.4 | 2.73 |
| Carbon Dioxide | 160 | 321 | 69.1 |
| Methane | 2.07 | 16.2 | 1.17 |

1 GPU = 1 × 10$^{-6}$ cm$^3$(STP)/cm$^2$ · s · cmHg

TABLE 44

| | Selectivity (−) | | |
|---|---|---|---|
| Gas Pair | 6FDA-ODA | 6FDA-NDA | 6FDA-mPDA |
| $N_2/CH_4$ | 1.5 | 1.4 | 2.3 |
| $CO_2/CH_4$ | 77.3 | 19.8 | 59.1 |

Example 43

Pure Gas Permeation Experiments with Perfluoro Membranes

Composite membranes were prepared by dip-coating asymmetric, microporous poly(etherimide) [PEI] support membranes in solutions of one of three perfluoro polymer solutions:

40% tetrafluoroethylene/60% 2,2,4-trifluoro-5-trifluoromethoxy-1,3-dioxole (Hyflon® AD60), (Ausimont, Italy).

20% tetrafluoroethylene/80% 2,2,4-trifluoro-5-trifluoromethoxy-1,3-dioxole (Hyflon® AD80), (Ausimont, Italy).

polyperfluoro (alkenyl vinyl ether) (Cytop®), (Asahi Glass, Japan).

Samples of each finished composite membrane were cut into 12.6-cm$^2$ stamps and tested in a permeation test-cell apparatus with pure gases at 23° C. feed temperature, 65 psia feed pressure, and permeate pressure atmospheric. During each test, the feed, permeate, and residue compositions were analyzed by gas chromatography (GC). The gas fluxes of the membranes were measured, and the pressure-normalized fluxes and selectivities were calculated. Table 45 summarizes the fluxes and Table 46 summarizes the selectivities of the composite membranes, calculated as the ratio of the pure gas fluxes.

TABLE 45

| Gas | Pure-Gas Pressure-Normalized Flux (GPU) | | |
|---|---|---|---|
| | Hyflon ® AD60 | Hyflon ® AD80 | Cytop ® |
| Nitrogen | 35.9 | 52.1 | 17.8 |
| Oxygen | 124 | 170 | 74 |
| Carbon Dioxide | 260 | 426 | 201 |
| Methane | 14.4 | 20.1 | 6.01 |

1 GPU = 1 × 10$^{-6}$ cm$^3$(STP)/cm$^2$ · s · cmHg

TABLE 46

| Gas Pair | Selectivity (-) | | |
|---|---|---|---|
| | Hyflon ® AD60 | Hyflon ® AD80 | Cytop ® |
| $O_2/N_2$ | 3.5 | 3.3 | 4.2 |
| $N_2/CH_4$ | 2.5 | 2.6 | 3.0 |
| $CO_2/CH_4$ | 18.0 | 21.2 | 33.4 |

Set 12

Mixed Gas Permeation Experiments

Several types of composite membranes were prepared using a PEI support membrane and a coating layer of a selective polymer, using a procedure similar to that described above.

Samples of each finished composite membrane were subjected to permeation tests with a gas mixture containing 20% nitrogen, 20% carbon dioxide and 60% methane, by cutting stamps and using the permeation test-cell apparatus as described above. The tests were carried out over a range of temperatures and feed gas pressures. The pressure on the permeate side of the cell was atmospheric in each case.

During each test, the feed, permeate, and residue compositions were analyzed by gas chromatography (GC). The pressure-normalized flux of each gas component and the selectivity for the gas pairs nitrogen/methane and carbon dioxide/methane were calculated.

Several types of composite membranes were prepared using a PEI support membrane and a coating layer of a selective polymer, using a procedure similar to that described above.

Samples of each finished composite membrane were subjected to permeation tests with a gas mixture containing 20% nitrogen, 20% carbon dioxide and 60% methane, by cutting stamps and using the permeation test-cell apparatus as described above. The tests were carried out over a range of temperatures and feed gas pressures. The pressure on the permeate side of the cell was atmospheric in each case.

During each test, the feed, permeate, and residue compositions were analyzed by gas chromatography (GC). The pressure-normalized flux of each gas component and the selectivity for the gas pairs nitrogen/methane and carbon dioxide/methane were calculated.

Example 44

Mixed Gas Permeation Experiments with Hyflon AD60 Membranes

Membranes were prepared and tested according to the methodology above, using Hyflon AD60 as the selective layer material. Two series of experiments were conducted.

In the first series, the temperature of the permeation cell was varied from 22° C. to −20° C. The feed pressure was maintained at 200 psig in this case. The flux and selectivity results for this series are shown in Table 47.

TABLE 47

| Temperature | Mixed-Gas Pressure-Normalized Flux (GPU) | | | Selectivity | |
|---|---|---|---|---|---|
| (° C.) | $N_2$ | $CO_2$ | $CH_4$ | $N_2/CH_4$ | $CO_2/CH_4$ |
| 22 | 71 | 462 | 30 | 2.34 | 15.3 |
| 10.5 | 65 | 467 | 26 | 2.46 | 17.8 |
| 0 | 59 | 457 | 23 | 2.57 | 20.0 |
| −20 | 47 | 458 | 17 | 2.77 | 27.3 |

Figure 9:
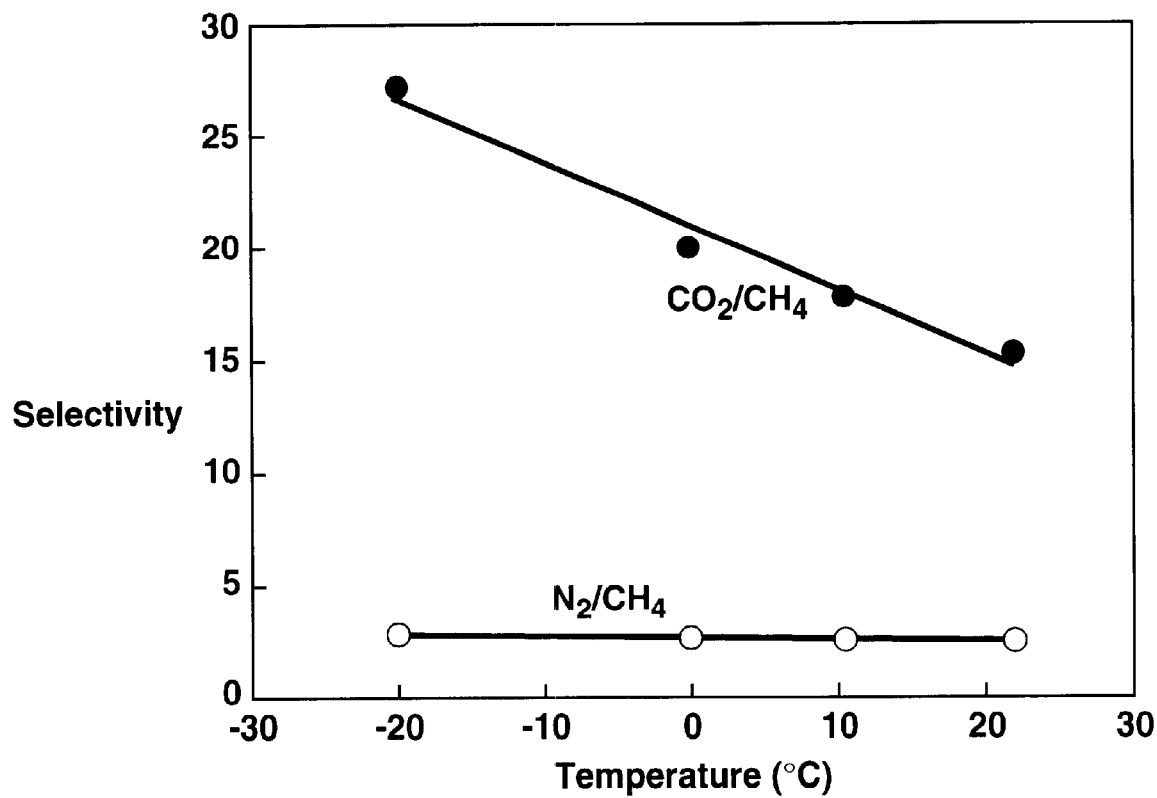
FIG. 9 is a graph of mixed gas selectivity of a Hyflon AD60 membrane as a function of temperature obtained with a mixture of 20% nitrogen, 20% carbon dioxide and 60% methane at 200 psig feed pressure.

As can be seen, the methane flux drops significantly as the temperature drops. The nitrogen flux drops less sharply and the carbon dioxide flux remains essentially constant, resulting in an increase in both carbon dioxide/methane and nitrogen/methane selectivity. At 10° C., the membranes have a nitrogen/methane selectivity of about 2.5. The selectivity results are shown graphically in FIG. 9.

In the Second series, the pressure on the feed side of the membrane was varied from 50 psig to 200 psig. In this case, the temperature was maintained at 22° C. The flux and selectivity results for this series are shown in Table 48.

TABLE 48

| Pressure | Mixed-Gas Pressure-Normalized Flux (GPU) | | | Selectivity | |
|---|---|---|---|---|---|
| (psig) | $N_2$ | $CO_2$ | $CH_4$ | $N_2/CH_4$ | $CO_2/CH_4$ |
| 50 | 70 | 407 | 30 | 2.31 | 13.5 |
| 100 | 75 | 489 | 32 | 2.34 | 15.4 |
| 150 | 72 | 472 | 31 | 2.34 | 15.3 |
| 200 | 71 | 462 | 30 | 2.34 | 15.3 |

Figure 10:
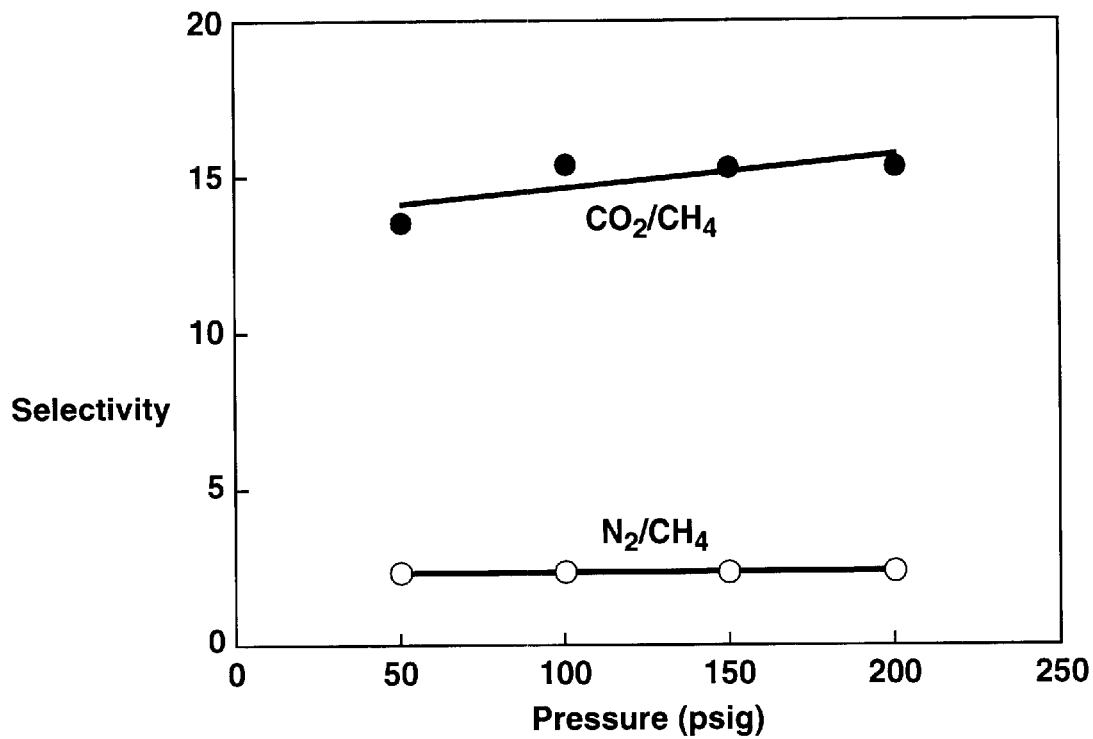
FIG. 10 is a graph of mixed gas selectivity of a Hyflon AD60 membrane as a function of feed gas pressure obtained with a mixture of 20% nitrogen, 20% carbon dioxide and 60% methane at 22° C.

As can be seen, the carbon dioxide flux increases with increasing feed pressure, but the fluxes of nitrogen and methane remain unchanged, indicating that the membrane is resistant to plasticization by carbon dioxide. As a result, the carbon dioxide/methane selectivity increases and the nitrogen/methane selectivity remains constant over this pressure range, as shown graphically in FIG. 10.

Example 45

Mixed Gas Permeation Experiments with Hyflon AD80 Membranes

Figure 11:
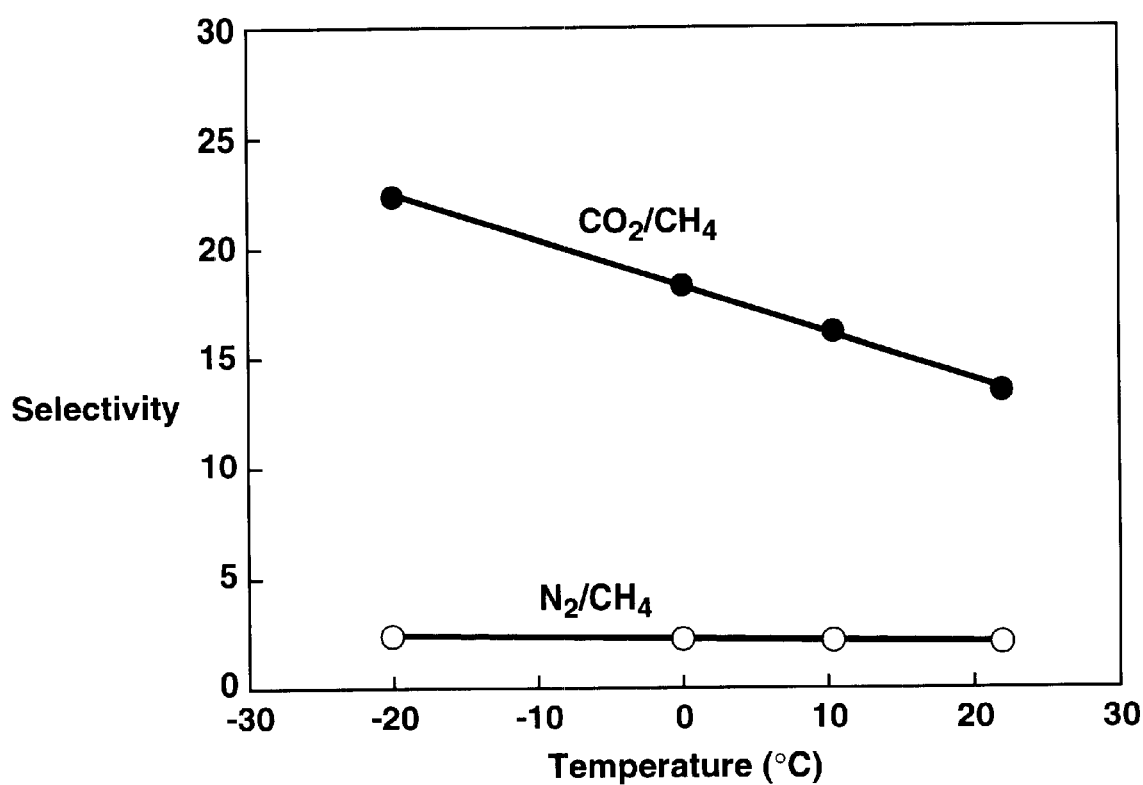
FIG. 11 is a graph of mixed gas selectivity of a Hyflon AD80 membrane as a function of temperature obtained with a mixture of 20% nitrogen, 20% carbon dioxide and 60% methane at 200 psig feed pressure.
Figure 12:
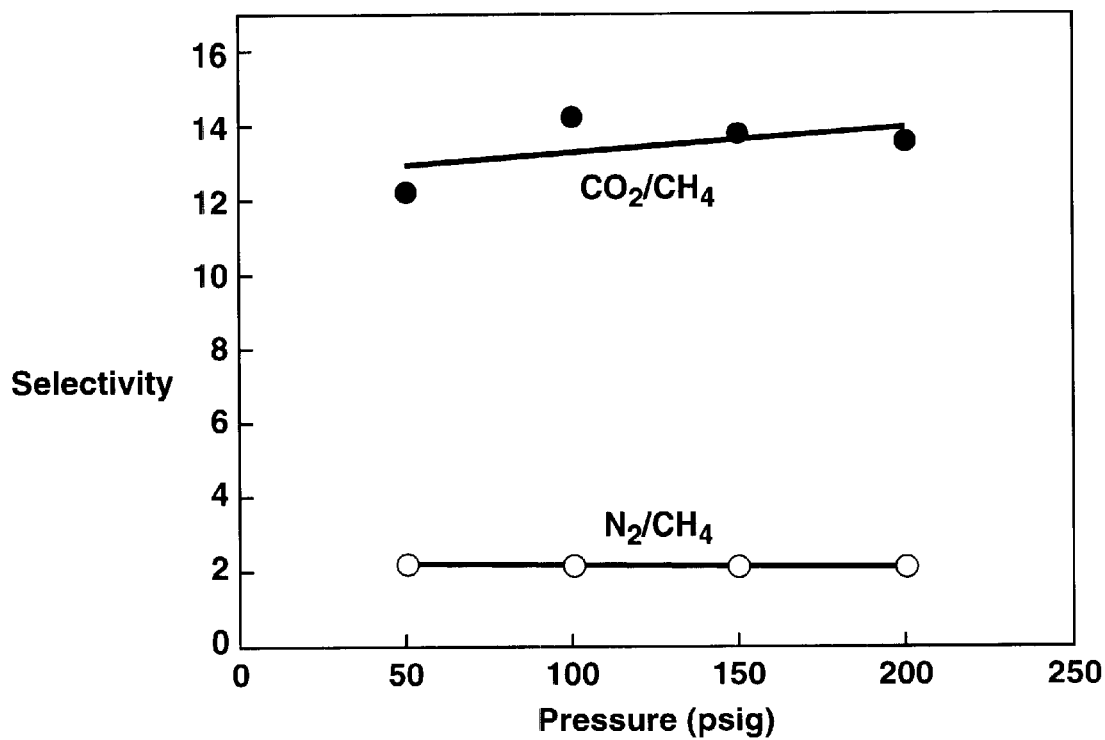
FIG. 12 is a graph of mixed gas selectivity of a Hyflon AD80 membrane as a function of feed gas pressure obtained with a mixture of 20% nitrogen, 20% carbon dioxide and 60% methane at 22° C.

The two series of experiments of Example 44 were repeated, using Hyflon AD80 as the selective layer material. The temperature series results are shown in Table 49 and FIG. 11, and the pressure series results are shown in Table 50 and FIG. 12.

TABLE 49

| Temperature | Mixed-Gas Pressure-Normalized Flux (GPU) | | | Selectivity | |
|---|---|---|---|---|---|
| (° C.) | $N_2$ | $CO_2$ | $CH_4$ | $N_2/CH_4$ | $CO_2/CH_4$ |
| 22 | 80 | 512 | 38 | 2.13 | 13.6 |
| 10.5 | 69 | 496 | 31 | 2.26 | 16.3 |
| 0 | 61 | 484 | 26 | 2.31 | 18.4 |
| −20 | 51 | 472 | 21 | 2.43 | 22.5 |

As can be seen, Hyflon AD80 is a little more permeable and a little less selective than Hyflon AD60. Cooling to 0° C. provides a nitrogen/methane selectivity of about 2.3.

TABLE 50

| Pressure | Mixed-Gas Pressure-Normalized Flux (GPU) | | | Selectivity | |
|---|---|---|---|---|---|
| (psig) | $N_2$ | $CO_2$ | $CH_4$ | $N_2/CH_4$ | $CO_2/CH_4$ |
| 50 | 76 | 421 | 34 | 2.20 | 12.2 |
| 100 | 80 | 525 | 37 | 2.17 | 14.3 |
| 150 | 80 | 514 | 37 | 2.14 | 13.8 |
| 200 | 80 | 512 | 38 | 2.13 | 13.6 |

As can be seen, the membrane again exhibit good resistance to plasticization. In this case the nitrogen/methane selectivity drops very slightly and the carbon dioxide/methane selectivity increases slightly feed pressure.

Example 46

Mixed Gas Permeation Experiments with Cytop Membranes

Figure 13:
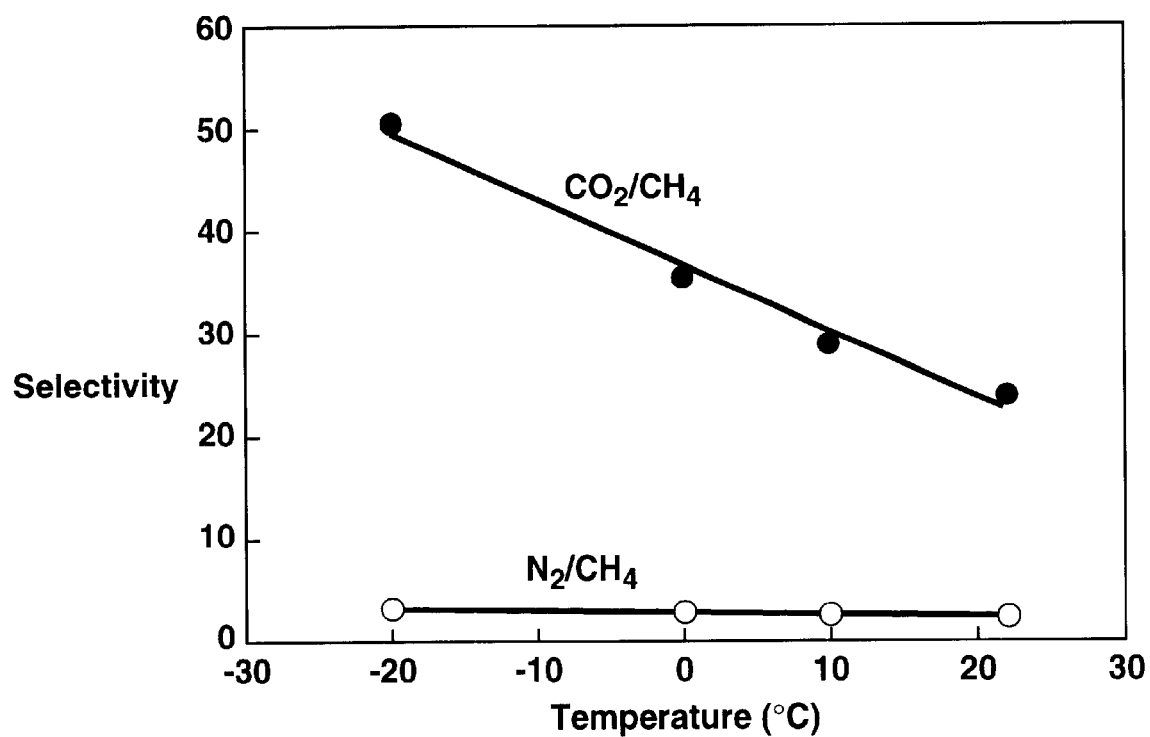
FIG. 13 is a graph of mixed gas selectivity of a Cytop membrane as a function of temperature obtained with a mixture of 20% nitrogen, 20% carbon dioxide and 60% methane at 200 psig feed pressure.
Figure 14:
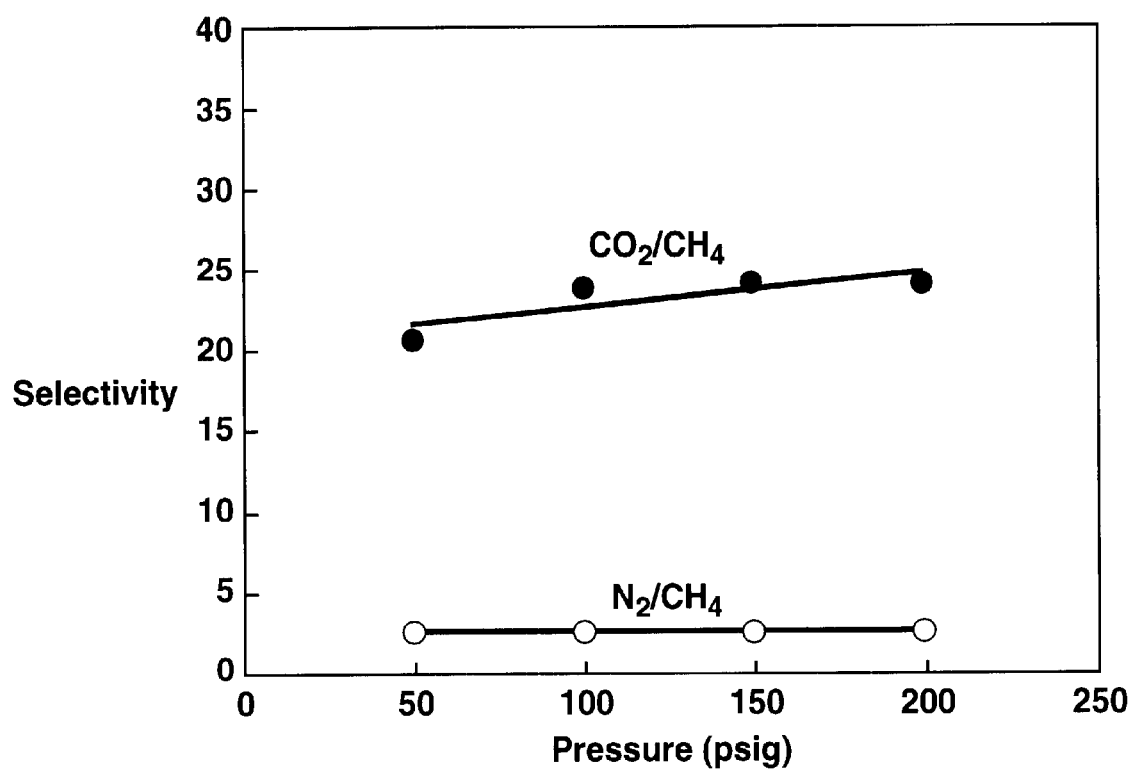
FIG. 14 is a graph of mixed gas selectivity of a Cytop membrane as a function of feed gas pressure obtained with a mixture of 20% nitrogen, 20% carbon dioxide and 60% methane at 22° C.

The two series of experiments of Example 44 were repeated, using Cytop as the selective layer material. The temperature series results are shown in Table 51 and FIG. 13, and the pressure series results are shown in Table 52 and FIG. 14.

TABLE 51

| Temperature | Mixed-Gas Pressure-Normalized Flux (GPU) | | | Selectivity | |
|---|---|---|---|---|---|
| (° C.) | $N_2$ | $CO_2$ | $CH_4$ | $N_2/CH_4$ | $CO_2/CH_4$ |
| 22 | 15 | 137 | 5.7 | 2.70 | 24.2 |
| 10.5 | 12 | 123 | 4.2 | 2.80 | 29.2 |
| 0 | 8.3 | 99 | 2.8 | 3.00 | 35.8 |
| −20 | 5.3 | 79 | 1.6 | 3.40 | 50.5 |

As can be seen, Cytop is less permeable but more selective than Hyflon. Cooling to 0° C. provides a nitrogen/methane selectivity of about 3. This is a very high value for a gas mixture containing substantial quantities of carbon dioxide and at high pressure.

TABLE 52

| Pressure | Mixed-Gas Pressure-Normalized Flux (GPU) | | | Selectivity | |
|---|---|---|---|---|---|
| (psig) | $N_2$ | $CO_2$ | $CH_4$ | $N_2/CH_4$ | $CO_2/CH_4$ |
| 50 | 14 | 108 | 5.2 | 2.67 | 20.8 |
| 100 | 15 | 136 | 5.7 | 2.61 | 24.0 |
| 150 | 14 | 129 | 5.3 | 2.64 | 24.3 |
| 200 | 15 | 137 | 5.6 | 2.67 | 24.2 |

As can be seen, the membranes showed only a modest increase in carbon dioxide flux and no increase in nitrogen or methane flux as the feed pressure was increased. Thus, the selectivity for both gas pairs was constant over the pressure range.

Example 47

Mixed Gas Permeation Experiments with Polyimide Membranes

Membranes were prepared and tested according to the methodology above, using PVDF as the support layer material and three polyimides, 6FDA-ODA, 6FDA-NDA, and 6FDA-mPDA as the selective layer material. It was found difficult to coat a defect-free polyimide selective layer on the support membranes, so the membranes also included gutter layers of poly(1-trimethylsilyl-1-propyne) [PTMSP].

Permeation experiments over a range of temperatures and pressures were conducted as previously described. Representative results for the 6FDA-mPDA membrane are shown in Tables 53 and 54.

TABLE 53

| Temperature | Mixed-Gas Pressure-Normalized Flux (GPU) | | | Selectivity | |
|---|---|---|---|---|---|
| (° C.) | $N_2$ | $CO_2$ | $CH_4$ | $N_2/CH_4$ | $CO_2/CH_4$ |
| 22 | 0.63 | 16.6 | 0.36 | 1.74 | 45.6 |
| 5.5 | 0.36 | 13.9 | 0.22 | 1.65 | 63.4 |
| 0 | 0.28 | 12.3 | 0.18 | 1.58 | 69.6 |
| −20 | 0.12 | 7.8 | 0.09 | 1.35 | 88.3 |

TABLE 54

| Pressure | Mixed-Gas Pressure-Normalized Flux (GPU) | | | Selectivity | |
|---|---|---|---|---|---|
| (psig) | $N_2$ | $CO_2$ | $CH_4$ | $N_2/CH_4$ | $CO_2/CH_4$ |
| 50 | 0.59 | 9.0 | 0.32 | 1.80 | 28.5 |
| 100 | 0.63 | 15.0 | 0.35 | 1.78 | 44.6 |
| 150 | 0.66 | 16.8 | 0.38 | 1.75 | 44.5 |
| 200 | 0.63 | 16.6 | 0.36 | 1.74 | 45.6 |

The membranes were not optimized and, as can be seen, the pressure-normalized fluxes are low compared with the pure gas data reported in Example 42 for membranes on a PEI support. Surprisingly, the nitrogen/methane selectivity seems to decline, rather than increase, as the temperature is lowered. The reason for this was not known. A possible factor may be the temperature behavior of the PTMSP gutter layer. Similar results were obtained with the other polyimides.

We claim:

1. A process for removing nitrogen from a gas stream comprising methane and at least about 4% nitrogen, the process comprising the steps of:
   (a) providing a first membrane unit containing a first membrane having a first feed side and a first permeate side,
   the first membrane being characterized by having the capability to exhibit a first nitrogen/methane selectivity in the range about 2–5 at a first temperature higher than about −25° C.;
   (b) providing a second membrane unit containing a second membrane having a second feed side and a second permeate side,
   the second membrane being characterized by having the capability to exhibit a second nitrogen/methane selectivity in the range about 2–5 at a second temperature higher than about −25° C.,
   the second membrane unit being connected in series with the first membrane unit such that gas leaving the first feed side can enter the second membrane unit on the second feed side;
   (c) passing the gas stream at a feed temperature above about −25° C. into the first membrane unit and across the first feed side;
   (d) withdrawing from the first feed side a first residue stream enriched in methane compared with the gas stream;

(e) withdrawing from the first permeate side a first permeate stream depleted in methane compared with the gas stream;

(f) passing the first residue stream into the second membrane unit and across the second feed side;

(g) withdrawing from the second feed side as a product stream a second residue stream enriched in methane compared with the first residue stream, and containing no more than about 6% nitrogen;

(h) withdrawing from the second permeate side a second permeate stream depleted in methane compared with the first residue stream.

2. The process of claim 1, wherein the gas stream is compressed before step (c).

3. The process of claim 2, further comprising:

(i) passing at least a portion of the first permeate stream as fuel into a combustion zone of a gas engine driving a compressor in which the gas stream is compressed.

4. The process of claim 1, further comprising recompressing the second permeate stream and recirculating it to step (c).

5. The process of claim 4, further comprising:

(i) passing at least a portion of the first permeate stream as fuel into a combustion zone of a gas engine driving a compressor in which the gas stream is compressed.

6. The process of claim 1, wherein the gas stream is cooled by heat exchange against at least one of the first and second permeate streams before step (c).

7. The process of claim 1, wherein the first membrane and the second membrane provide a transmembrane pressure-normalized nitrogen flux during the process of at least about 1 gpu.

8. The process of claim 1, wherein the first membrane and the second membrane provide a transmembrane pressure-normalized nitrogen flux during the process of at least about 10 gpu.

9. The process of claim 1, wherein the gas stream comprises natural gas.

10. The process of claim 1, wherein the gas stream comprises at least about 10% nitrogen.

11. The process of claim 1, wherein the gas stream further comprises at least one component selected from the group consisting of carbon dioxide, hydrogen sulfide and water vapor.

12. The process of claim 1, wherein at least one of the first membrane and the second membrane comprises a polymer characterized by having repeating units of a fluorinated, non-aromatic ring structure, the ring having at least five members, and further characterized by a fractional free volume no greater than about 0.3.

13. The process of claim 1, wherein the product stream contains no more than about 4% nitrogen.

14. The process of claim 1, wherein the product stream contains no more than about 4% nitrogen, no more than about 2% carbon dioxide, no more than about 4 ppm hydrogen sulfide and no more than about 140 ppm water vapor.

15. The process of claim 1, further comprising passing the first permeate stream to an additional membrane separation stage.

16. The process of claim 1, wherein the product stream contains at least about 70% of the methane content of the gas stream.

17. The process of claim 1, wherein at least one of the second permeate stream and the gas stream passes through a compression step upstream of step (c), which compression step is the only compression step in the process.

18. The process of claim 1, wherein the first feed temperature is sufficient to provide a nitrogen/methane selectivity between about 2 and 5 and a transmembrane pressure-normalized nitrogen flux of at least about 1 gpu.

19. A process for removing nitrogen from a gas stream comprising methane and at least about 4% nitrogen, the process comprising the steps of:

(a) providing a first membrane unit containing a first membrane having a first feed side and a first permeate side, the first membrane being characterized by having the capability to exhibit a first nitrogen/methane selectivity in the range about 2–5 at a first temperature higher than about –25° C.;

(b) providing a second membrane unit containing a second membrane having a second feed side and a second permeate side, the second membrane being characterized by having the capability to exhibit a second nitrogen/methane selectivity in the range about 2–5 at a second temperature higher than about –25° C., the second membrane unit being connected in series with the first membrane unit such that gas leaving the first feed side can enter the second membrane unit on the second feed side;

(c) passing the gas stream into the first membrane unit, at a feed temperature sufficient to provide a nitrogen/methane selectivity between about 2 and 5 and a transmembrane pressure-normalized nitrogen flux of at least about 1 gpu., into the first membrane unit and across the first feed side;

(d) withdrawing from the first feed side a first residue stream enriched in methane compared with the gas stream;

(e) withdrawing from the first permeate side a first permeate stream depleted in methane compared with the gas stream;

(f) passing the first residue stream into the second membrane unit and across the second feed side;

(g) withdrawing from the second feed side as a product stream a second residue stream enriched in methane compared with the first residue stream, and containing no more than about 6% nitrogen;

(h) withdrawing from the second permeate side a second permeate stream depleted in methane compared with the first residue stream.

20. The process of claim 19, wherein the gas stream is compressed before step (c).

21. The process of claim 20, further comprising:

(i) passing at least a portion of the first permeate stream as fuel into a combustion zone of a gas engine driving a compressor in which the gas stream is compressed.

22. The process of claim 19, further comprising recompressing the second permeate stream and recirculating it to step (c).

23. The process of claim 22, further comprising:

(i) passing at least a portion of the first permeate stream as fuel into a combustion zone of a gas engine driving a compressor in which the gas stream is compressed.

24. The process of claim 19, wherein the gas stream is cooled by heat exchange against at least one of the first and second permeate streams before step (c).

25. The process of claim 19, wherein the first membrane and the second membrane provide a transmembrane pressure-normalized nitrogen flux during the process of at least about 10 gpu.

26. The process of claim 19, wherein the gas stream comprises natural gas.

27. The process of claim 19, wherein the gas stream comprises at least about 10% nitrogen.

28. The process of claim 19, wherein the gas stream further comprises at least one component selected from the group consisting of carbon dioxide, hydrogen sulfide and water vapor.

29. The process of claim 19, wherein at least one of the first membrane and the second membrane comprises a polymer characterized by having repeating units of a fluorinated, non-aromatic ring structure, the ring having at least five members, and further characterized by a fractional free volume no greater than about 0.3.

30. The process of claim 19, wherein the product stream contains no more than about 4% nitrogen.

31. The process of claim 19, wherein the product stream contains no more than about 4% nitrogen, no more than about 2% carbon dioxide, no more than about 4 ppm hydrogen sulfide and no more than about 140 ppm water vapor.

32. The process of claim 19, further comprising passing the first permeate stream to an additional membrane separation stage.

33. The process of claim 19, wherein the product stream contains at least about 70% of the methane content of the gas stream.

34. The process of claim 19, wherein at least one of the second permeate stream and the gas stream passes through a compression step upstream of step (c), which compression step is the only compression step in the process.

35. The process of claim 19, wherein the feed temperature is between about 10° C. and −10° C.

36. A process for removing nitrogen from a gas stream comprising methane and at least about 4% nitrogen, the process comprising the steps of:
   (a) providing a first membrane unit containing a first membrane having a first feed side and a first permeate side,
      the first membrane being characterized by having the capability to exhibit a first nitrogen/methane selectivity in the range about 2–5 at a first temperature higher than about −25° C.;
   (b) providing a second membrane unit containing a second membrane having a second feed side and a second permeate side,
      the second membrane being characterized by having the capability to exhibit a second nitrogen/methane selectivity in the range about 2–5 at a second temperature higher than about −25° C.,
      the second membrane unit being connected in series with the first membrane unit such that gas leaving the first feed side can enter the second membrane unit on the second feed side;
   (c) providing a third membrane unit containing a third membrane having a third feed side and a third permeate side,
      the third membrane being characterized by having the capability to exhibit a third nitrogen/methane selectivity in the range about 2–5 at a third temperature higher than about −25° C.,
      the third membrane unit being connected in series with the first membrane unit such that gas leaving the first permeate side can enter the third membrane unit on the third feed side;
   (d) passing the gas stream at a first feed temperature into the first membrane unit and across the first feed side;
   (e) withdrawing from the first feed side a first residue stream enriched in methane compared with the gas stream;
   (f) withdrawing from the first permeate side a first permeate stream depleted in methane compared with the gas stream;
   (g) passing the first residue stream into the second membrane unit and across the second feed side;
   (h) withdrawing from the second feed side as a product stream a second residue stream enriched in methane compared with the first residue stream, and containing no more than about 6% nitrogen;
   (i) withdrawing from the second permeate side a second permeate stream depleted in methane compared with the first residue stream;
   (j) passing the first permeate stream into the third membrane unit and across the third feed side;
   (k) withdrawing from the third feed side a third residue stream enriched in methane compared with the first permeate stream;
   (l) withdrawing from the third permeate side a third permeate stream depleted in methane compared with the first permeate stream.

37. The process of claim 36, wherein the gas stream is compressed before step (d).

38. The process of claim 36, further comprising recompressing the second permeate stream and recirculating it to step (d).

39. The process of claim 36, further comprising recompressing the third residue stream and recirculating it to step (d).

40. The process of claim 36, wherein the product stream contains no more than about 4% nitrogen.

41. The process of claim 36, wherein the product stream contains no more than about 4% nitrogen, no more than about 2% carbon dioxide, no more than about 4 ppm hydrogen sulfide and no more than about 140 ppm water vapor.

42. The process of claim 36, further comprising passing the third permeate stream to an additional membrane separation stage.

43. The process of claim 36, wherein the first feed temperature is above about −25° C.

* * * * *